(12) United States Patent
Baba et al.

(10) Patent No.: US 8,924,164 B2
(45) Date of Patent: Dec. 30, 2014

(54) APPARATUS AND METHOD FOR ULTRASONIC TESTING

(71) Applicant: Hitachi, Ltd., Chiyoda-ku, Tokyo (JP)

(72) Inventors: Atsushi Baba, Tokai (JP); So Kitazawa, Mito (JP); Naoyuki Kono, Mito (JP)

(73) Assignee: Mitsubishi Hitachi Power Systems, Ltd., Kanagawa (JP)

( * ) Notice: Subject to any disclaimer, the term of this patent is extended or adjusted under 35 U.S.C. 154(b) by 68 days.

(21) Appl. No.: 13/827,363

(22) Filed: Mar. 14, 2013

(65) Prior Publication Data

US 2013/0197824 A1    Aug. 1, 2013

Related U.S. Application Data

(62) Division of application No. 12/606,608, filed on Oct. 27, 2009, now abandoned.

(30) Foreign Application Priority Data

Oct. 29, 2008  (JP) ................................ 2008-278038
Oct. 29, 2008  (JP) ................................ 2008-278053
Feb. 26, 2009  (JP) ................................ 2009-043586

(51) Int. Cl.

| | |
|---|---|
| *G01B 5/28* | (2006.01) |
| *G01S 15/89* | (2006.01) |
| *G01N 29/04* | (2006.01) |
| *G01N 29/26* | (2006.01) |
| *G01N 29/07* | (2006.01) |
| *G01N 29/24* | (2006.01) |

(52) U.S. Cl.

CPC ............ *G01N 29/04* (2013.01); *G01S 15/8993* (2013.01); *G01N 2291/106* (2013.01); *G01N 29/262* (2013.01); *G01S 15/8918* (2013.01); *G01N 29/07* (2013.01); *G01N 29/2468* (2013.01); *G01S 15/8997* (2013.01); *G01S 15/8925* (2013.01); *G01S 15/8927* (2013.01)

USPC ........................................................... 702/39

(58) Field of Classification Search

CPC ...................................................... A61B 8/483
USPC ........................................................... 702/39
See application file for complete search history.

(56) References Cited

U.S. PATENT DOCUMENTS

| 6,135,956 A | 10/2000 | Schmiesing et al. |
| 6,503,199 B1 | 1/2003 | Lennon |

(Continued)

FOREIGN PATENT DOCUMENTS

| JP | 03-122563 A | 5/1991 |
| JP | 05-244691 A | 9/1993 |

(Continued)

OTHER PUBLICATIONS

European Search Report received in European Application No. 11010055 dated Mar. 28, 2012.

(Continued)

*Primary Examiner* — Stephen Cherry
(74) *Attorney, Agent, or Firm* — Mattingly & Malur, PC

(57) ABSTRACT

An apparatus and a method for ultrasonic testing obtains high-resolution and high-S/N ratio testing results by driving a number of piezoelectric elements using fewer pulsers and receivers in comparison with the number of elements composing an array transducer. A sensor information setter sets a plurality of piezoelectric element groups used for transmission and a plurality of piezoelectric element groups used for reception among the plurality of piezoelectric elements composing an ultrasonic array transducer. A computer transmits an ultrasonic wave from the element cluster set for transmission, and stores an ultrasonic wave received by the element cluster set for reception. The procedure is repeated including different element cluster sets for transmission and reception to obtain first receive signals. The first receive signals are summed to obtain a second receive signal; and the second receive signal is displayed with reference to the sensor center position on a display unit.

1 Claim, 37 Drawing Sheets

(56) References Cited

U.S. PATENT DOCUMENTS

| | | | |
|---|---|---|---|
| 2002/0173721 | A1 | 11/2002 | Grunwald et al. |
| 2005/0101867 | A1 | 5/2005 | Johnson et al. |
| 2005/0228277 | A1 | 10/2005 | Barnes et al. |
| 2006/0173334 | A1* | 8/2006 | Azuma et al. .................. 600/447 |
| 2006/0195273 | A1 | 8/2006 | Maurer et al. |
| 2006/0219013 | A1* | 10/2006 | Baba et al. ...................... 73/618 |
| 2009/0293621 | A1 | 12/2009 | Kitazawa et al. |

FOREIGN PATENT DOCUMENTS

| | | | |
|---|---|---|---|
| JP | 2003-093382 | A | 4/2003 |
| JP | 2005-106654 | A | 4/2005 |
| JP | 2005-315582 | A | 11/2005 |
| JP | 2005-351718 | A | 12/2005 |
| JP | 2006-006490 | A | 1/2006 |
| JP | 2006-308566 | A | 11/2006 |
| JP | 2006-317417 | A | 11/2006 |

OTHER PUBLICATIONS

M. Kondo et al., Digital Signal Processing Series vol. 12, Digital Signal Processing in Measurement and Sensors, Shokodo Co. Ltd., May 20, 1993, pp. 143-186. (partial translation attached).

Y. Yokono, Global Trend of Phased Array Ultrasonic Testing: Its Practical Application and Standardization, The Japanese Society for Non-destructive Inspection, vol. 56, No. 10, 2007, pp. 510-515. (partial translation attached).

A. Baba et al., Development of Three-dimensional Ultrasonic Testing System 3D Focus-UT, Japan Society of Maintenology, 5th Academic Lecture, Collection of Summaries, pp. 155-157. (English Abstract attached.).

The Japanese Society for Non-destructive Inspection NDIS 2418:2005, pp. 17-23, 43-45. (Partial translation attached.).

A. Potts et al., Presentation and Analysis Enhancements of the NDT Workbench a Software Package for Ultrasonic NDT Data, Review of Progress in Quantitative Nondestructive Evaluation: vol. 19. AIP Conference Proceedings, vol. 509, pp. 741-748 (2000).

J. A. Johnson et al., Coherent-Array Imaging Using Phased Subarrays. Part I: Basic Principles, IEEE Transactions on Ultrasonics, Ferroelectrics, and Frequency Control, XP55000971, Jan. 2005, 14 pp., vol. 52, No. 1.

I. Wygant et al., Volumetric Imaging Using Fan-Beam Scanning with Reduced Redundancy 2D Arrays, IEEE Ultrasonics Symposium, XP31076756, Oct. 1, 2006, 4 pp.

Kitazawa et al.; "3-Dimensional Phased Array Ultrasonic Probing System"; Inspection Technology, Feb. 2009; vol. 14, No. 2 pp. 23-27 with English Translation.

G. Toullelan et al., Application of a 3D Smart Flexible Phased-Array to Piping Inspection, AIP Conference Proceedings, American Institute of Physics, New York, US, Feb. 28, 2008, pp. 794-800, vol. 975, XP007918186.

\* cited by examiner

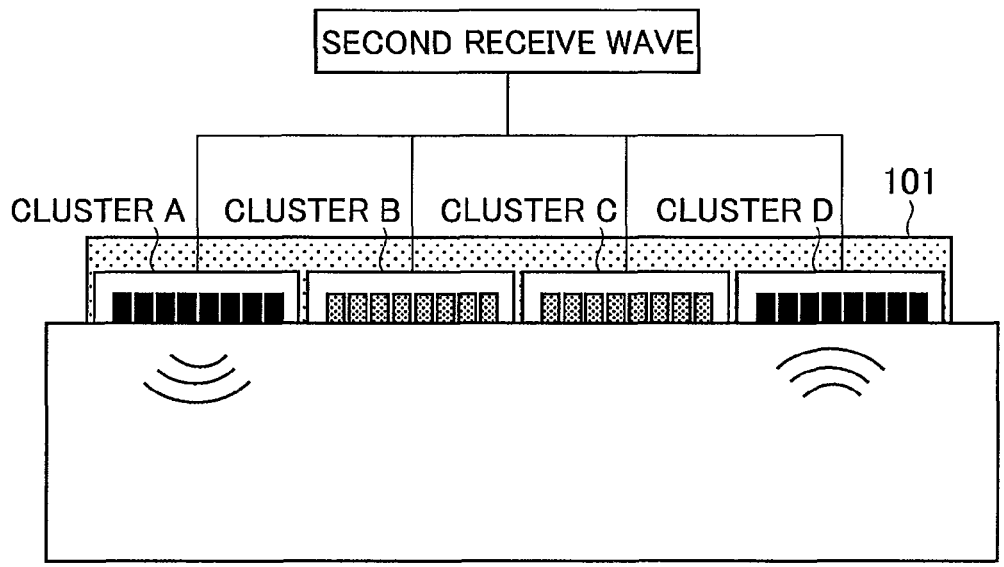

| TRANSMISSION \ RECEPTION | A | B | C | D |
|---|---|---|---|---|
| A | ○ | ○ | ○ | ○ |
| B | ○ | ○ | ○ | ○ |
| C | ○ | ○ | ○ | ○ |
| D | ○ | ○ | ○ | ○ |

| TRANSMISSION \ RECEPTION | A | B | C | D |
|---|---|---|---|---|
| A | × | ○ | ○ | ○ |
| B | ○ | × | ○ | ○ |
| C | ○ | ○ | × | ○ |
| D | ○ | ○ | ○ | × |

APPARATUS AND METHOD FOR ULTRASONIC TESTING

This application is a divisional of U.S. patent application Ser. No. 12/606,608, filed Oct. 27, 2009.

BACKGROUND OF THE INVENTION

1. Field of the Invention

The present invention relates to an apparatus and a method for ultrasonic testing which is one of non-destructive testing methods. More particularly, the present invention is related to an apparatus and a method for ultrasonic testing by using an array ultrasonic sensor.

2. Description of the Related Art

Conventional ultrasonic testing methods targeting various kinds of structural materials utilize an ultrasonic sensor composed of a single element for transmission and reception of an ultrasonic wave. The ultrasonic sensor receives an ultrasonic signal reflected by a defect or the like inside an object under test to detect a defect based on the propagation time of the ultrasonic signal and the position of the ultrasonic sensor.

Specifically, conventional methods comprises the steps of: appropriately selecting an angle and vibration mode (longitudinal wave, transversal wave, etc.) of an ultrasonic wave to be applied to the object under test; moving the ultrasonic sensor to obtain a position at which a sufficiently strong reflected wave (echo) can be obtained from a defect; and identifying the size of the defect based on a difference between reception times of reflected waves from the bottom surface (far-side boundary surface) and the top face (near-side boundary surface) of the object under test, multiplied by the sonic velocity of the material of the object under test.

These methods are commonly used for ordinary defect inspections because of their simple operating principle and relatively simple instrumentation. However, since it is necessary to measure a reflected ultrasonic wave and evaluate the existence and position of a defect only from reception time of the reflected wave, high-accuracy testing requires experienced inspector and is time-consuming.

In recent years, new ultrasonic testing methods have been developed. As represented by the phased array method, these new techniques image the inside of an object under test with high accuracy (refer to, for example, Nonpatent Document 1).

The phased array method utilizes a so-called ultrasonic array transducer composed of an array of several tens of piezoelectric elements and operates on a principle that wave fronts of ultrasonic waves transmitted from the piezoelectric elements mutually interfere to form one combined wave front in the course of propagation. Therefore, controlling the timing of ultrasonic wave transmission from each piezoelectric element with a time delay (on a time-shift basis) makes it possible to control the ultrasonic beam angle and allow the ultrasonic wave to focus.

When receiving reflected ultrasonic waves, summing up these waves received by the piezoelectric elements on a time-shift basis makes it possible to control the receive beam angle of one combined ultrasonic wave as well as receive ultrasonic waves at one focal position in a similar way to transmission.

Generally known processes for the phased array method include the linear scanning process which linearly feeds piezoelectric elements and the sectorial scanning process which changes ultrasonic-wave transmit and receive directions in a fan-like form. Both processes can apply ultrasonic waves at high speed without moving the ultrasonic sensor and control the beam angle and focal depth position of the ultrasonic wave without replacing the ultrasonic sensor. Therefore, it can be said that both techniques enable high-speed and high-accuracy testing.

Of the above-mentioned conventional techniques, the phased array method has the advantage of controlling the beam angle and focal position of the combined ultrasonic wave by using a plurality of piezoelectric elements, and allowing high-speed and high-accuracy testing.

On the other hand, the focal depth is determined by an aperture of the array transducer (nearly equals the size of a piezoelectric element composing the array transducer multiplied by the number of elements). Therefore, testing an object having a long propagation path therein or a thick plate requires a large-sized array transducer (an array transducer composed of a number of elements) having a focal depth suitable for its size.

For example, suppose a case where a steel material (with a sonic velocity of longitudinal ultrasonic wave of 6000 m/s and a wavelength of 3 mm) is tested by using an array transducer with a frequency of 2 MHz. Generally, with an ultrasonic transducer having an aperture size of A (mm), the ultrasonic wave is strong in the vicinity of the near-sound-field limit distance (NF) represented by the formula (1) below. Therefore, an ultrasonic transducer having a larger aperture is required to test a thicker material. When using an array transducer normally having a constant frequency and a constant interval between piezoelectric elements, it is necessary to use a multi-element array transducer having increased number of piezoelectric elements for testing.

[Formula 1]

$$NF = A^2/4\lambda \qquad (1)$$

An ultrasonic testing apparatus employing a multi-element array transducer needs to have pulser, receiver, and wiring circuits corresponding to the total number of elements in order to drive the multi-element array transducer. Accordingly, there has been a problem that a remarkable increase in size and complexity in internal structure and wiring causes degradation in portability, installability, and maintainability.

In order to solve this problem, an imaging method using a small number of pulsers and receivers corresponding to the number of some elements of the ultrasonic array transducer, for example, the synthetic aperture method is used (Nonpatent Document 2).

With the synthetic aperture method, a single ultrasonic transducer having a small sensor aperture transmits an ultrasonic wave so that it widely spreads out into an object under test, and the same or different ultrasonic transducer receives a reflected ultrasonic wave signal (echo) from the inside of the object.

The operating principle of the synthetic aperture method is that, since the propagation path of ultrasonic wave is known, a defect serving as a sound source of a received reflected ultrasonic wave exists on a circular arc having the position of a piezoelectric element which transmitted and received an ultrasonic wave as a center and the propagation distance of the reflected ultrasonic wave as a radius. (When different piezoelectric elements are used for transmission and reception, a defect exists on an ellipse arc having each of the piezoelectric element for transmission and the piezoelectric element for reception as a focal position.)

Based on this operating principle, the ultrasonic sensor transmits and receives ultrasonic waves while sequentially changing the position of an active ultrasonic transducer for transmission and reception. At each transducer position, a receive signal is spread out in a circular arc form (or in an ellipse arc form) through computer operations. Then, intersections of these circular arcs focus at one position where a defect exists (a true reflection source position) thus allowing the defect position to be located and imaged.

[Nonpatent Document 1]

Yoshikazu Yokono, Global Trend of Phased Array Ultrasonic Testing Its Practical Application and Standardization, The Japanese Society for Non-destructive Inspection, Vol. 56, No. 10, 2007.

[Nonpatent Document 2]

Michimasa Kondo, Yoshimasa Ohashi, and Akio Jitsumori, Digital Signal Processing Series Vol. 12, Digital Signal Processing in Measurement and Sensors, pp. 143-186, May 20, 1993, SHOKODO CO., LTD.

A conventional method for testing a defect of an object under test such as a structural material transmits an ultrasonic wave by using a single ultrasonic sensor and receives echoes reflected by a defect or the like inside the object under test by using a single ultrasonic sensor to detect a defect based on the propagation time of the ultrasonic wave and the position of the ultrasonic sensor. The conventional method also moves the ultrasonic sensor to obtain a position where a reflected echo from a defect is obtained, and identifies the size of the defect based on a difference between reception times of reflected echoes from the bottom and surface, multiplied by the sonic velocity of the material of the object under test. This method is commonly used for ordinary defect inspections because of its simple operating principle and relatively simple instrumentation. However, since it is necessary to measure reflected ultrasonic echoes and evaluate existence and position of a defect from the reception time of the reflected echoes, high-accuracy testing requires experienced inspector and is time-consuming.

In recent years, new ultrasonic testing methods have been developed. As represented by well-known phased array method and synthetic aperture focusing method, these new techniques image the inside of an object under test with high accuracy. The phased array method utilizes an array of a plurality of piezoelectric elements and operates on a principle that wave fronts of ultrasonic signals transmitted from the piezoelectric elements mutually interfere to form one combined wave front in the course of propagation. Therefore, controlling the timing of ultrasonic wave transmission from each piezoelectric element with a time delay (on a time-shift basis) makes it possible to control the ultrasonic beam angle and allow ultrasonic wave to focus. When receiving reflected ultrasonic waves, summing up these waves received by the piezoelectric elements on a time-shift basis on the time axis makes it possible to receive ultrasonic waves at one focal position in a similar way to transmission. The phased array method makes it possible to apply ultrasonic waves at high speed without moving the ultrasonic sensor and control the beam angle and focus depth position of the ultrasonic wave without replacing the ultrasonic sensor. Therefore, it can be said that the phased array method enables high-speed and high-accuracy testing. Generally known processes for the phased array method include the linear scanning process which linearly feeds piezoelectric elements and the sectorial scanning process which changes ultrasonic-wave transmit and receive directions in a fan-like form.

On the other hand, the synthetic aperture method transmits an ultrasonic wave so that it widely spreads out into an object under test, and receives a reflected ultrasonic signal from the inside of the object. The operating principle of the synthetic aperture method is that a defect serving as a sound source of the received reflected ultrasonic wave exists on a circular arc having the position of a piezoelectric element which transmitted and received an ultrasonic wave as a center and the propagation distance of the reflected ultrasonic wave as a radius. Based on this operating principle, the ultrasonic sensor transmits and receives ultrasonic waves while sequentially changing the position of a piezoelectric element. At each vibrator position, a received waveform is spread out in a circular arc form through computer operations. Then, intersections of these circular arcs focus at one position where a defect exists (an ultrasonic wave reflection source) thus allowing the defect position to be located and imaged. Actually, the synthetic aperture method performs high-resolution imaging through computer operations using the position of the ultrasonic sensor and the ultrasonic waveform signal at that position. Details of computer operations are discussed in Nonpatent Document 2.

In recent years, new sensors such as a matrix array transducer and a ring array transducer have been developed. The matrix array transducer is composed of an array of piezoelectric elements arranged in a matrix pattern inside an array ultrasonic sensor, and the ring array transducer is composed of an array of coaxially arranged piezoelectric elements (including arrangements in the circumferential direction). Further, apparatuses that can transmit and receive ultrasonic waves by using a number of piezoelectric elements have come into practical use. Thus, the inside of an object under test directly under the ultrasonic sensor can be three-dimensionally imaged without moving the ultrasonic sensor. With a known method for three-dimensionally imaging the inside of an object under test, a two-dimensional array ultrasonic sensor transmits an ultrasonic wave sequentially from each element and then receives a reflected ultrasonic wave with all elements and, at the same time, three-dimensional aperture synthetic processing is performed so as to superimpose received echoes (refer to, for example, Patent Document 1).

[Patent Document 1]

JP-2005-315582-A

[Nonpatent Document 2]

Michimasa Kondo, Yoshimasa Ohashi, and Akio Jitsumori, Digital Signal Processing Series Vol. 12, Digital Signal Processing in Measurement and Sensors, pp. 143-186, May 20, 1993, SHOKODO CO., LTD.

In recent years, new ultrasonic testing methods targeting various kinds of structural materials have been developed. As represented by the phased array method, these new techniques image and test the inside of an object under test with high accuracy in a short time (refer to, for example, Nonpatent Document 3).

The phased array method utilizes an array of a plurality of piezoelectric elements (also referred to as ultrasonic array transducer) and operates on a principle that wave fronts of ultrasonic waves transmitted from the piezoelectric elements mutually interfere to form one combined wave front in the course of propagation. Therefore, controlling the timing of ultrasonic wave transmission from each piezoelectric element with a time delay (on a time-shift basis) makes it possible to control the ultrasonic beam angle and allow the ultrasonic wave to focus.

When receiving reflected ultrasonic waves, summing up these waves received by the piezoelectric elements on a time-shift basis in accordance with the delay time makes it possible to control the receive beam angle of one combined ultrasonic wave as well as receive ultrasonic waves at one focal position in a similar way to transmission.

Generally known processes for the phased array method using a one-dimensional array transducer having linearly arranged piezoelectric elements include the linear scanning process which scans in ultrasonic-wave transmit and receive directions together, and the sectorial scanning process which changes ultrasonic-wave transmit and receive directions in a fan-like form centering on an incident point. Further, the use of a two-dimensional array transducer having piezoelectric elements arranged in a lattice pattern makes it possible to three-dimensionally focus on a desired spatial position, allowing selection of a scanning process which best suits the shape of the object under test. In particular, the three-dimensional scanning technique makes it possible to apply ultrasonic waves at high speed without moving the sensor, and control the beam angle and focal depth position of the ultrasonic wave, allowing high-speed and high-accuracy testing.

At present, in order to locate a spatial position of a reflection source from reflected ultrasonic wave signals, a method for presuming a spatial position from a plurality of two-dimensional images of reflection strength distributions at different cutting positions is commonly used (hereinafter this method is referred to as two-dimensional phased array method). For example, since the linear and sectorial scanning processes can obtain a plurality of two-dimensional images corresponding to a scanning range and interval, the direction in which a reflected wave appears can be located by sequentially changing the images on the display screen.

Recently, a new three-dimensional display method (hereinafter referred to as three-dimensional ultrasonic testing method) has been reported. This method performs interpolation processing to reflected ultrasonic wave signals from a plurality of directions to create three-dimensional lattice-like data and then performs volume rendering and surface rendering techniques to the created data. Although there are more than one method for creating three-dimensional lattice-like data, for example, the synthetic aperture method and phased array method, a method based on the phased array method is particularly referred to as three-dimensional phased array method (refer to, for example, Nonpatent Document 2). As three-dimensional lattice-like data, a data structure composed of a plurality of three-dimensionally arranged cubic elements (referred to as voxels) is most widely used because of ease of handling. This structure is also referred to as structural lattice. Although a lattice having irregular spatial lattice arrangements may be used in addition to voxels, such a lattice is slightly more difficult to display than a voxel. This kind of lattice is referred to as non-structural lattice as represented by a six-face lattice, a four-face lattice, a triangular pyramidal (prism) lattice, and a quadrangular pyramidal (pyramid) lattice. Further, there is another method for displaying data as three-dimensional point groups without conversion to lattice-like data. Since these pieces of data are saved in computer memory as three-dimensional testing data, they can be checked from any desired direction by an inspector after measurement.

In recent years, flaw size measurement (sizing) using the phased array method has attracted attention in industrial fields. Particularly in the field of nuclear power, the phased array method has been specified as a method for sizing a fatigue crack of carbon steel and stainless steel and a crack height of a stress corrosion crack (SCC) of stainless steel by technical guidance JEAC 4207-2004 of the Japan Electric Association which serves as an evaluation criterion for the soundness of domestic light-water nuclear reactors. At present, this guidance is taken over to technical regulation JEAG4207-2008 of the Japan Electric Association. The scope of the phased array method has been expanded not only as a method for sizing crack height but also as a method for checking the existence of a crack (refer to, for example, Nonpatent Document 4).

When measuring a flaw height (crack height), the two-dimensional phased array method utilizes sectorial-scanned or linear-scanned images including echoes at ends of a flaw. In this case, measurement must be performed according to defined measurement and analysis procedures, and it is recommended to validate the procedures by using a test piece having a flaw. These procedures are prescribed as flaw height measurement method based on the tip echo technique by NDIS 2418 standard of the Japanese Society for Non-destructive Inspection (refer to, for example, Nonpatent Document 5).

However, with the two-dimensional phased array method, echoes corresponding to upper and lower ends of a crack (hereinafter referred respectively to as upper- and lower-end echoes) need to be included in the same screen. Therefore, it is necessary to finely adjust the sensor position and the ultrasonic beam angle depending on the orientation of a flaw. This method is time-consuming and requires experience to a certain extent. If the shape of the flaw is included in the same plane, it is preferable to find and measure an image in which upper- and lower-end echoes are clearly displayed in this way. However, if the shape of the flaw is complicated with many branches, such as scc, the shape of the flaw is not necessarily included in the same plane. In this case, two or more images are needed to measure the flaw height accuracy with the two-dimensional phased array method.

In this case, the use of the three-dimensional ultrasonic testing method is very effective. Although there are not many cases reported, a sizing method based on the three-dimensional ultrasonic testing method has been devised. A method discussed in Nonpatent Document 6 displays measurement data points obtained by a plurality of tests on a screen as point groups. With a desired cross section displayed, for example, when two points corresponding to upper- and lower-end echoes are specified by using a mouse or keyboard of a computer, the distance between the two points is output. With the two-dimensional phased array method, it is necessary to find a screen in which upper- and lower-end echoes are simultaneously included at the time of data storage. With the three-dimensional ultrasonic testing method, on the other hand, it is only necessary to perform a series of data storage for a predetermined testing range and then find a target cross section. The latter method makes testing procedures very efficient and is advantageous.

[Nonpatent Document 3]

Yoshikazu Yokono, Global Trend of Phased Array Ultrasonic Testing Its Practical Application and Standardization, The Japanese Society for Non-destructive Inspection, Vol. 56, No. 10, (2007)

[Nonpatent Document 4]

Atsushi Baba, Satoshi Kitazawa, Naoyuki Kono, Yuji Adachi, Mitsuru Odakura, and Osamu Kikuchi, Development of Three-dimensional Ultrasonic Testing System 3D Focus-UT, JAPAN SOCIETY OF MAINTENOLOGY, 5th Academic Lecture, Collection of Summaries, 155 (2008)

[Nonpatent Document 5]

The Japanese Society for Non-destructive Inspection NDIS 2418:2005, pp. 21

[Nonpatent Document 6]

Potts, A.; McNab, A.; Reilly, D.; Toft, M., "Presentation and analysis enhancements of the NDT Workbench a software package for ultrasonic NDT data", REVIEW OF PROGRESS IN QUANTITATIVE NONDESTRUCTIVE EVALUATION: Volume 19. AIP Conference Proceedings, Volume 509, pp. 741-748 (2000).

SUMMARY OF THE INVENTION

However, the synthetic aperture method described in the first background art has a problem that it is difficult to obtain a receive signal having a sufficient S/N ratio. Since this method uses a single ultrasonic transducer having a small sensor aperture, applying it to a case with a long propagation distance of ultrasonic wave disperses or attenuates the ultrasonic wave signal resulting in a decrease in signal intensity.

A first object of the present invention is to provide an apparatus and a method for ultrasonic testing which make it possible to obtain high-resolution and high-S/N ratio testing results through imaging by driving a number of piezoelectric elements, the apparatus and method comprising less number of pulsers and receivers in comparison with the number of elements composing an array transducer.

With the second background art, it is necessary to store a data processing table (focal law, delay time) corresponding to the number of coordinate positions of three-dimensional testing data in order to obtain focused three-dimensional testing data over the entire three-dimensional space. Since the number of coordinate positions is physically limited, there is a trade-off relation between the size of a target region and the spatial resolution of three-dimensional imaging. Therefore, in order to three-dimensionally image a wide testing range with high resolution, it is necessary to divide the testing range into a plurality of test regions and repeat a sequence comprising reading a data processing table, reconfiguring the table, and measurement.

Although the second background art provides favorable accuracy and sensitivity in imaging directly under a two-dimensional array ultrasonic sensor, there has been a problem that both accuracy and sensitivity fall in imaging at a position not directly under the ultrasonic sensor. Therefore, for a wide testing range, testing needs to be performed separately in a plurality of steps to cover the entire testing range.

With the second background art, the two-dimensional array ultrasonic sensor is composed of small-sized piezoelectric elements, each providing weak ultrasonic transmission energy, and the sensor transmits an ultrasonic wave with one element during transmission. Therefore, the spatial energy of the ultrasonic wave is weak. Also during reception, since the receive energy per element is weak, the sensor is susceptible to noise including electrical noise. This causes a problem that, with a thick object and a high attenuation material, the echo intensity of the ultrasonic wave decreases to degrade the S/N ratio of the received echo.

A second object of the present invention is to provide an apparatus and a method for ultrasonic imaging which enable collective three-dimensional imaging over a wide testing range based on high resolution and high S/N ratio three-dimensional testing data and allow images to be handled as one piece of three-dimensional testing data by using a two-dimensional array ultrasonic sensor. The present embodiment only utilizes one set of data processing table (focal law) and is also applicable to thick objects and high-attenuation materials.

Further, with the defect sizing method based on conventional three-dimensional ultrasonic testing methods described in the third background art, it is difficult and time-consuming to a certain extent to find and specify a cross section including upper- and lower-end echoes on the screen. Further, in order to grasp which cross section is currently being observed, it is necessary to constantly monitor the three-dimensional display screen and the cross-section screen for comparison. Further, in order to perform a plurality of measurements in combination with echoes at different positions, it is necessary to find a plurality of cross sections corresponding to each combination. This causes a problem of complicated procedures.

A third object of the present invention is to provide an apparatus and a method for ultrasonic testing which enable three-dimensional measurement of the distance between echoes in a simple way in sizing a defect such as a crack.

In order to attain the above-mentioned first object, the present invention provides an ultrasonic testing apparatus for testing the inside of an object under test by transmitting an ultrasonic wave to the object under test and receiving reflected waves (echoes) from the surface or inside thereof by using an ultrasonic array transducer composed of a plurality of one- or two-dimensionally arranged piezoelectric elements. The ultrasonic testing apparatus includes: a sensor information setting unit configured to set a plurality of element groups (element clusters) to be used for transmission and reception out of a plurality of piezoelectric elements composing the ultrasonic array transducer; a transmission selection unit configured to select an element cluster for transmission out of the set plurality of element clusters; a reception selection unit configured to select an element cluster for reception out of the set plurality of element clusters; a delay time control unit configured to give a delay time to each of the piezoelectric elements for transmission and/or piezoelectric elements for reception with reference to a sensor center position serving as a reference for the delay time; a computer configured to obtain a second receive signal by performing the steps of: transmitting an ultrasonic wave from the element cluster set for transmission, storing an ultrasonic wave received by the element cluster set for reception as a first receive signal; repeating a procedure for changing the element cluster set for transmission and the element cluster set for reception and storing another first receive signal; and summing up the plurality of first receive signals obtained by repeating the same procedure; and a display unit configured to display the second receive signal with reference to the sensor center position.

The above-mentioned configuration makes it possible to obtain high-resolution and high-S/N ratio testing results through imaging by driving a number of piezoelectric elements, the ultrasonic testing apparatus comprising less number of pulsers and receivers in comparison with the number of elements composing the array transducer.

In order to attain the above-mentioned first object, the present invention provides an ultrasonic testing method for testing the inside of an object under test and receiving reflected waves (echoes) from the surface or inside thereof by using an ultrasonic array transducer composed of a plurality of one- or two-dimensionally arranged piezoelectric elements. The ultrasonic testing method comprises the steps of: setting a plurality of element groups (element clusters) to be used for transmission and reception out of a plurality of piezoelectric elements composing the ultrasonic array transducer; selecting an element cluster for transmission out of the set plurality of element clusters, and selecting an element cluster for reception out of the set plurality of element clusters; giving a delay time to each of the piezoelectric elements for transmission and/or the piezoelectric elements for reception with reference to a sensor center position serving as a reference for the delay time; transmitting an ultrasonic wave from the element cluster set for transmission, and storing an ultrasonic wave received by the element cluster set for reception as a first receive signal; repeating a procedure for changing the element cluster set for transmission and the element cluster set for reception and storing another first receive signal; summing up the plurality of first receive signals obtained by repeating the same procedure to obtain a second receive signal; and displaying the second receive signal with reference to the sensor center position.

The above-mentioned method makes it possible to obtain high-resolution and high-S/N ratio testing results through imaging by driving a number of piezoelectric elements, the ultrasonic testing apparatus comprising less number of pulsers and receivers in comparison with the number of elements composing the array transducer.

In order to attain the above-mentioned second object, the present invention provides a method for three-dimensional ultrasonic imaging comprising the steps of: transmitting an ultrasonic wave from a two-dimensional array ultrasonic sensor to focus at a desired depth; three-dimensionally scanning the inside of an object under test while varying the ultrasonic beam angle, and storing waveform data; converting the obtained waveform data to three-dimensional testing data; storing the three-dimensional testing data by sequentially changing the set position of the array ultrasonic sensor; and combining the three-dimensional testing data obtained at each testing position while making a shift by the displacement of the array ultrasonic sensor to attain three-dimensional imaging.

The above-mentioned method enables collective three-dimensional imaging over a wide testing range based on high resolution and high S/N ratio three-dimensional testing data and allows images to be handled as one piece of three-dimensional testing data by using a two-dimensional array ultrasonic sensor. The present embodiment only utilizes one set of data processing table (focal law) and is also applicable to thick objects and high-attenuation materials.

In order to attain the above-mentioned second object, the present invention provides an apparatus comprising: a two-dimensional array ultrasonic sensor composed of a plurality of piezoelectric elements; pulsers configured to transmit a transmit signal to each piezoelectric element of the array ultrasonic sensor; receivers configured to receive a receive signal; a delay control unit configured to perform time control for the transmit and receive signals by varying a delay time for each piezoelectric element; a data storage unit configured to store ultrasonic waveforms transmitted and received by the array ultrasonic sensor; a sensor moving unit configured to move the array ultrasonic sensor, and a scanning control unit configured to control the sensor moving unit; a displacement detection unit configured to measure the displacement of the array ultrasonic sensor; a computer configured to convert the stored waveform data to three-dimensional testing data, and combine the plurality of pieces of three-dimensional testing data while making a shift by the displacement of the array ultrasonic sensor measured by the displacement detection unit; and a display unit configured to display the combined testing data.

The above-mentioned configuration enables collective three-dimensional imaging over a wide testing range based on high resolution and high S/N ratio three-dimensional testing data and allows images to be handled as one piece of three-dimensional testing data by using a two-dimensional array ultrasonic sensor. The present embodiment only utilizes one set of data processing table (focal law) and is also applicable to thick objects and high-attenuation materials.

Further, in order to attain the above-mentioned third object, the present invention provides an apparatus comprising: an ultrasonic sensor composed of a plurality of piezoelectric elements; pulsers configured to supply a transmit signal to each piezoelectric element of the ultrasonic sensor; receivers configured to input a receive signal from each piezoelectric element of the ultrasonic sensor; data storage unit configured to store ultrasonic waveforms received by the ultrasonic sensor; a computer for image processing configured to generate three-dimensional testing data from the waveforms stored in the data storage unit; and a three-dimensional display unit configured to display the three-dimensional testing data generated by the computer, wherein the computer outputs the distance between two points specified on the three-dimensional display unit.

The above-mentioned configuration enables three-dimensional measurement of the distance between echoes in a simple way in sizing a defect such as a crack.

In order to attain the above-mentioned third object, the present invention provides a three-dimensional ultrasonic testing method for testing the inside of an object under test by transmitting an ultrasonic wave to the object under test; and receiving reflected waves therefrom by using an ultrasonic sensor composed of a plurality of piezoelectric elements, wherein the distance between two echoes caused by reflected ultrasonic wave signals is measured based on the distance between two points specified on the three-dimensional display unit.

The above-mentioned method enables three-dimensional measurement of the distance between echoes in a simple way in sizing a defect such as a crack.

BRIEF DESCRIPTION OF THE DRAWINGS

FIG. 6 illustrates a receive signal obtained by a combination of a plurality of element clusters in the ultrasonic testing apparatus according to the first embodiment of the present invention.

FIG. 7 illustrates receive signals obtained by a combination of a plurality of element clusters in the ultrasonic testing apparatus according to the first embodiment of the present invention.

DESCRIPTION OF THE PREFERRED EMBODIMENTS

Configuration and operation of an ultrasonic testing apparatus according to a first embodiment of the present invention will be described below with reference to FIGS. 1 to 14.

First of all, the configuration of the ultrasonic testing apparatus according to the present embodiment will be described below with reference to FIG. 1.

Figure 1:
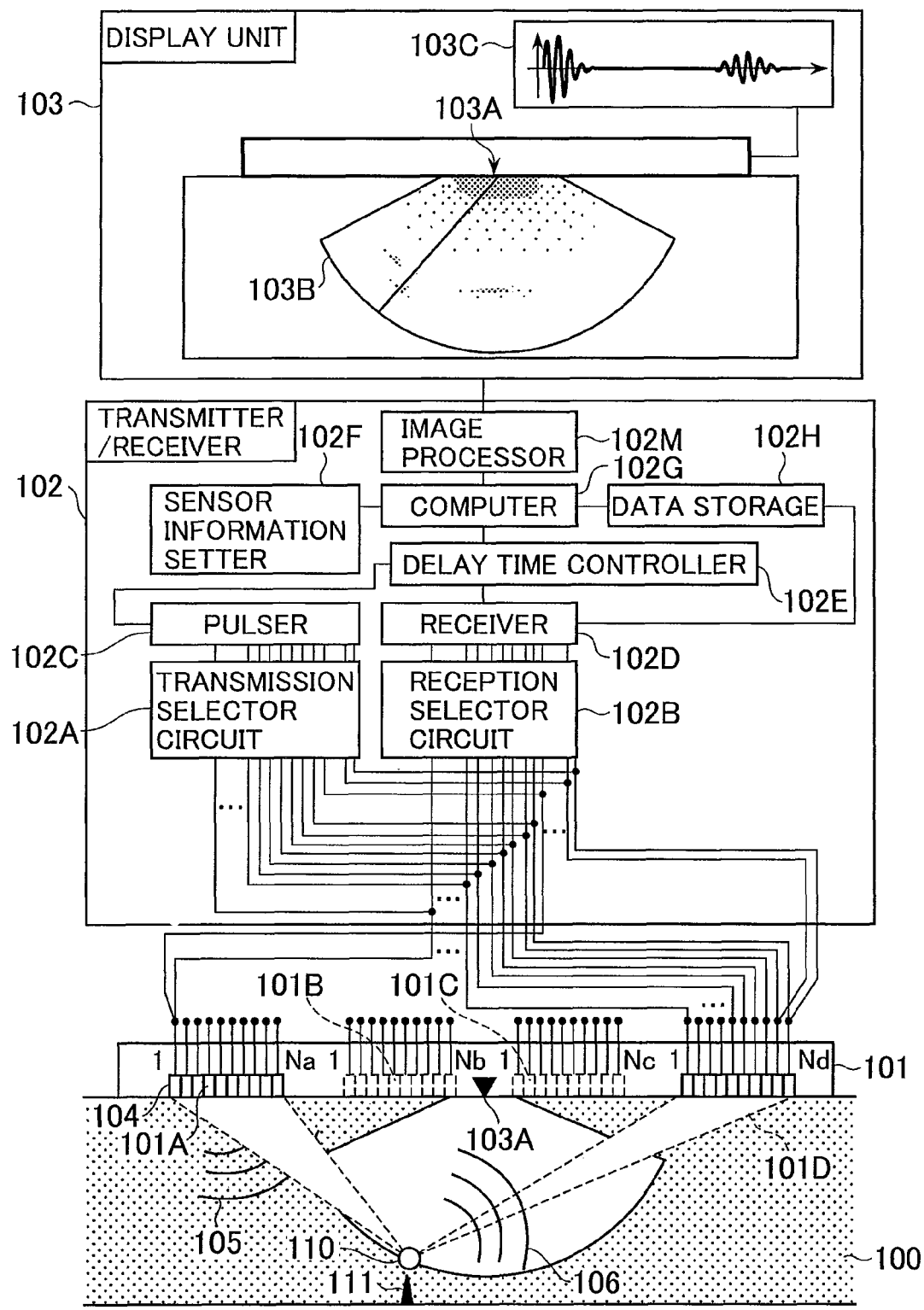
FIG. 1 is a block diagram illustrating a configuration of an ultrasonic testing apparatus according to a first embodiment of the present invention.

FIG. 1 is a block diagram illustrating a configuration of the ultrasonic testing apparatus according to the first embodiment of the present invention.

The ultrasonic testing apparatus according to the present embodiment includes an ultrasonic array transducer 101 which transmits ultrasonic waves to an object under test 100, a transmitter/receiver 102, and a display unit 103 which displays testing images. The present embodiment tests a reflection source 111 such as a defect and a crack in the inside or on the surface of the object under test 100 by imaging.

The ultrasonic array transducer 101 is basically composed of a plurality of one- or two-dimensionally arranged piezoelectric elements 104, each being able to transmit and receive an ultrasonic wave. The ultrasonic array transducer 101 is disposed on a testing surface of the object under test 100 through a coupling medium (such as water, glycerin, or other liquids) or a shoe (made of a synthetic resin such as acrylics). The ultrasonic array transducer 101 transmits an ultrasonic wave 105 by using a drive signal supplied from the transmitter/receiver 102, propagates the ultrasonic wave 105 in the object under test 100, detects a reflected wave (echo) 106, and sends a receive signal to the transmitter/receiver 102.

The array transducer 101 of FIG. 1 is composed of N piezoelectric elements (N=Na+Nb+Nc+Nd) and connected to the transmitter/receiver 102 through connectors and cables. Suppose that numbers Na, Nb, Nc, and Nd are all the same, for example, 64, and therefore N is 256. However, the numbers Na, Nb, Nc, and Nd may not necessarily be the same.

With the present embodiment, N piezoelectric elements are grouped into four different groups of piezoelectric elements, i.e., an element cluster 101A composed of piezoelectric element #1 to #Na, an element cluster 101B composed of element #1 to #Nb, an element cluster 101C composed of element #1 to #Nc, and an element cluster 101D composed of element #1 to #Nd. The ultrasonic array transducer 101 transmits and receives ultrasonic waves on an element cluster basis.

The transmitter/receiver 102 transmits and receives ultrasonic waves by using the ultrasonic array transducer 101. The transmitter/receiver 102 includes a transmission selector circuit 102A, a reception selector circuit 102B, a pulser 102C, a receiver 102D, a delay time controller 102E, a sensor information setter 102F, a computer 102G, data storage 102H, and an image processor 102M. The sensor information setter 102F determines an element group (the element cluster 101A) to be used for transmission, and based on the determination, the transmission selector circuit 102A electrically connects the element cluster 101A and the pulser 102C. Then, the pulser 102C supplies a drive signal to the ultrasonic array transducer 101, and the element cluster 101A for transmission in the ultrasonic array transducer transmits the ultrasonic wave 105. When the ultrasonic wave 105 transmitted to the inside of the object under test 100 is reflected, for example, by the reflection source 111, a reflected ultrasonic wave 106 (echo) is generated. Then, in a similar way to transmission, the sensor information setter 102F determines an element cluster (the element cluster 101D) to be used for reception, and the reception selector circuit 102B electrically connects the element cluster 101D and the receiver 102D. The receiver 102D processes a receive signal.

Therefore, when the ultrasonic array transducer 101 is composed of 256 piezoelectric elements and each of the four element clusters is composed of 64 piezoelectric elements, for example, the transmitter/receiver 102 requires pulser, receiver, and wiring circuits accommodating 64 piezoelectric elements. With the present embodiment, however, the near-sound-field limit distance (NF) can be deeper than that in a case where each element cluster is composed of 64 piezoelectric elements, that is, the NF can be equivalent to that in a case where each element cluster is composed of 256 piezoelectric elements, as described in detail below.

The computer 102G controls the transmission selector circuit 102A, the reception selector circuit 102B, the pulser 102C, the receiver 102D, the delay time controller 102E, the data storage 102H, and the image processor M to perform required operations, as well as combines signals stored in the data storage 102H to perform imaging.

The sensor information setter 102F groups N piezoelectric elements composing the ultrasonic array transducer 101 into a plurality of piezoelectric element groups (element clusters). Then, the sensor information setter 102F sets a sensor center position 103A to be used as a reference for delay time and display, and calculates a delay time to be given to the array transducer 101 by using the computer 102G or stores precalculated data. Based on this delay time, the delay time controller 102E gives a delay pattern to the array transducer 101. When the sensor information setter 102F sets element clusters, it may be possible that the computer 102G sets the center position of the set piezoelectric element groups as the sensor center position 103A.

The transmission selector circuit 102A and the reception selector circuit 102B) respectively selects an element cluster used for transmission and an element cluster used for reception. For example, when the ultrasonic array transducer 101 is composed of N piezoelectric elements and four element clusters 101A to 101D, the ultrasonic array transducer 101 repeats the following operations: (1) transmission by the element cluster 101A and reception by the element cluster 101A, (2) transmission by the element cluster 101A and reception by the element cluster 101B, . . . based on a pattern determined by the sensor information setter 102F. For example, when the array transducer 101 is grouped into four element clusters 101A to 101D, as shown in FIG. 1, four different element clusters are available for both transmission and reception. Therefore, a combination of element clusters for transmission and reception is selected from a total of 16 (4×4) different combinations.

Signals received by piezoelectric elements of an element cluster for reception are subjected to A/D conversion, given a delay time based on a delay time pattern, and combined into (summed up to) one receive signal (first receive signal). Therefore, for example, when there are four different element clusters for transmission and four different element clusters for reception, i.e., 16 (4×4) different combinations of element clusters are available, a total of 16 first receive signals is stored in the data storage 102H.

The computer 102A combines (sums up) the first receive signals stored in the data storage 102H to derive a second receive signal. This second receive signal is displayed on the display unit 103 as an ultrasonic image. In this case, the sensor center position 103A which is a reference for delay time is also used as a reference position for image display.

Operations of the ultrasonic testing apparatus according to the present embodiment will be described below with reference to FIGS. 2 to 9.

Hereinafter, a first receive signal obtained by transmission by the i-th element cluster and reception by the j-th element cluster is referred to as Φij.

First of all, a focal position set by the ultrasonic testing apparatus according to the present embodiment will be described below with reference to FIG. 2.

Figure 2:
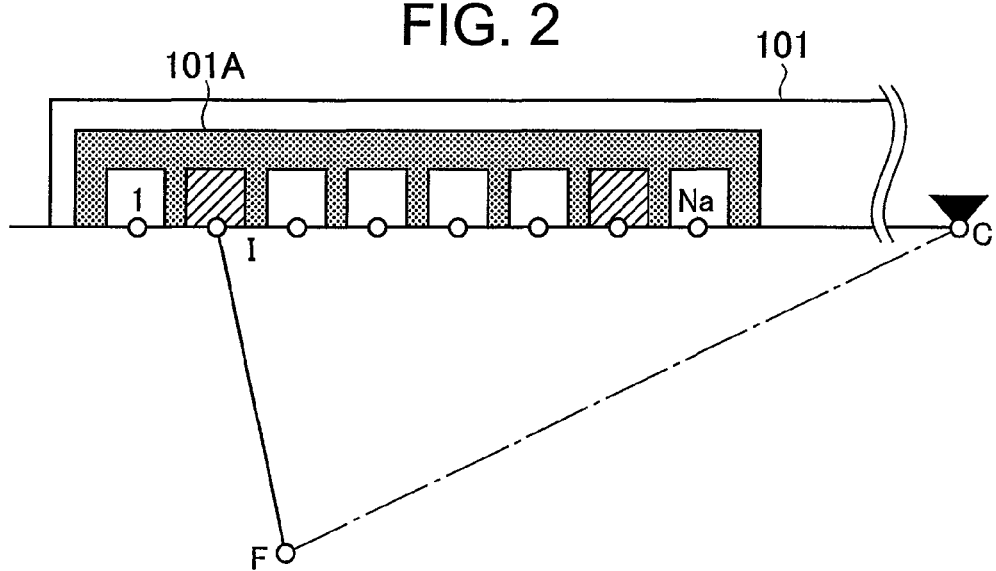
FIG. 2 illustrates a focal position setup in the ultrasonic testing apparatus according to the first embodiment of the present invention.

FIG. 2 illustrates the focal position set by the ultrasonic testing apparatus according to the first embodiment of the present invention.

The following description will be made on the premise that, in order to test the object under test 100, the sensor information setter 102F sets a focal position F as a position at which ultrasonic beams are focused (namely, focal point).

Of N piezoelectric elements composing the ultrasonic array transducer 101, Na piezoelectric elements constitute the element cluster 101A. Further, the sensor information setter 102F sets a point C as a sensor center position. For example, a delay time for the i-th element of the element cluster A is obtained with the following procedures:

A round-trip propagation time T between the sensor center position C and the focal position F is obtained by dividing two times a line CF by the ultrasonic velocity in the object under test. Similarly, a round-trip propagation time T between a piezoelectric element I and the focal point F is obtained by dividing two times a line IF by the sonic velocity therein.

In order to allow the ultrasonic wave to focus at the focal point F, it is necessary that ultrasonic beams from the piezoelectric elements reach the focal point F at the same time and be in phase thereat. Further, since the reference position for a final ultrasonic image is set to the point C, the distance of ultrasonic propagation needs to coincide with the line CF when the focal point F is measured by the ultrasonic array transducer 101. As mentioned above, it is preferable to apply delay processing to each element so that the propagation time from each element to the focal point coincide with the propagation time from the sensor center position to the focal point.

Propagation time and delay time in the ultrasonic testing apparatus according to the present embodiment will be described below with reference to FIGS. 3 to 5.

Figure 3:
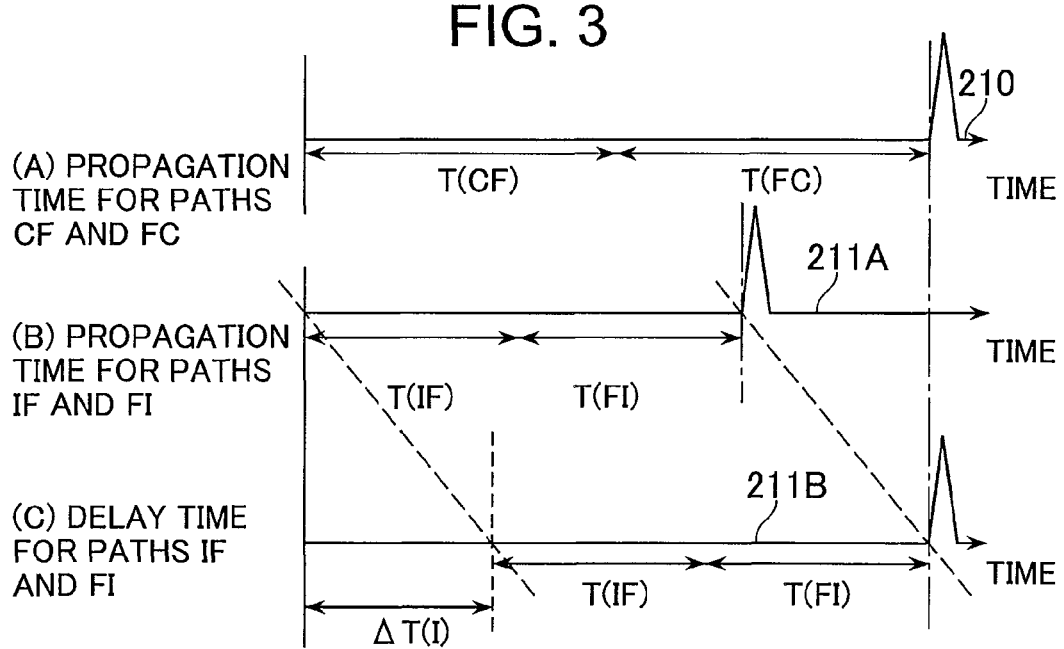
FIGS. 3 to 3 illustrates propagation times in the ultrasonic testing apparatus according to the first embodiment of the present invention.

FIG. 3 illustrates propagation times in the ultrasonic testing apparatus according to the first embodiment of the present invention. FIG. 4 illustrates a relation between the propagation time and the piezoelectric element number in the ultrasonic testing apparatus according to the first embodiment of the present invention. FIG. 5 illustrates a relation between the delay time and the piezoelectric element number in the ultrasonic testing apparatus according to the first embodiment of the present invention.

FIG. 3 (A) illustrates a round-trip propagation time T between the sensor center position C and the focal position F, i.e., the propagation time for paths CF and FC. FIG. 3 (B) illustrates a round-trip propagation time T between the piezoelectric element I and the focal position F, i.e., the propagation time for paths IF and FI. FIG. 3 (C) illustrates a delay time for paths IF and FI.

A difference $\Delta T(I)$ between the above-mentioned two propagation times is represented by formula (2).

[Formula 2]

$$\Delta T(I) = T(IF) + T(FI) - (T(CF) + T(FC)) \quad (2)$$

where $T(IF)+T(FI)$ is the propagation time for the paths IF and FI, and $T(CF)+T(FC)$ is the propagation time for the paths CF and FC.

When delay processing by the difference $\Delta T(I)$ between $T(CF)+T(FC)$ and $T(IF)+T(FI)$ is applied to the propagation time, the propagation time for the element I, $(\Delta T(I)+T(IF)+T(FI))$, coincides with the propagation time for the sensor center position, $(T(CF)+T(FC))$.

A delay time pattern for the ultrasonic array transducer 101 can be obtained by applying such delay processing to all the piezoelectric elements.

Figure 4:
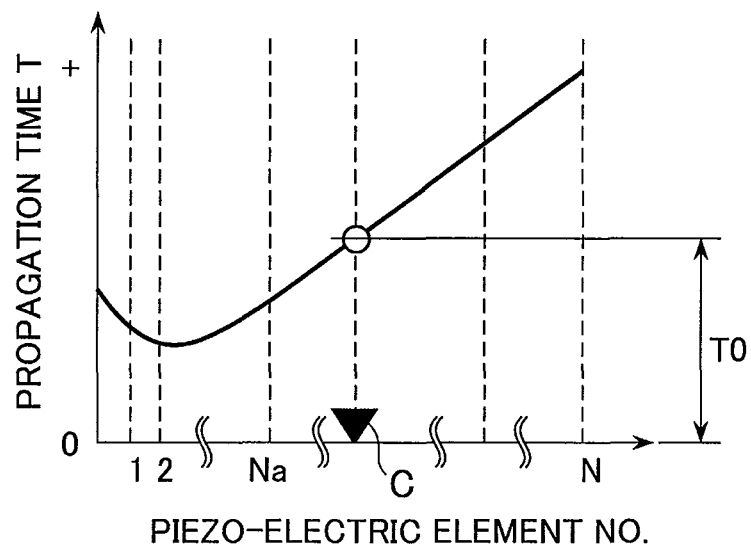
FIG. 4 illustrates a relation between the propagation time and the piezoelectric element number in the ultrasonic testing apparatus according to the first embodiment of the present invention.

FIG. 4 illustrates a relation between the piezoelectric element number and the propagation time T to the focal point.

With reference to a propagation time T0 from the sensor center position 103A to the focal point, the propagation time T0 is subtracted from the propagation time T for each piezoelectric element.

Figure 5:
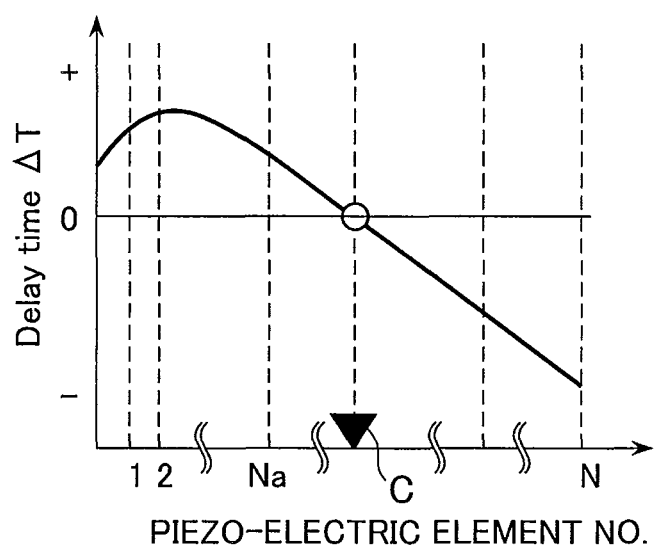
FIG. 5 illustrates a relation between the delay time and the piezoelectric element number in the ultrasonic testing apparatus according to the first embodiment of the present invention.

Then, as shown in FIG. 5, a delay time $\Delta T$ for each piezoelectric element can be obtained.

Thus, after giving a delay time $\Delta T$ (I) to each piezoelectric element, a first receive signal for each element is stored one by one.

A receive signal obtained by the combination of a plurality of element clusters in the ultrasonic testing apparatus according to the present embodiment will be described below with reference to FIGS. 6 and 7.

FIGS. 6 and 7 illustrates a receive signal obtained by the combination of a plurality of element clusters in the ultrasonic testing apparatus according to the first embodiment of the present invention.

FIG. 6 is a schematic view of the ultrasonic array transducer 101 composed of four element clusters A to D. A delay time calculated by formula (2) is set for each piezoelectric element of the element clusters A to D. When the element cluster A transmits an ultrasonic wave and the element cluster D receives a reflected wave, it is stored in the data storage 102H as a first receive signal $\Phi AD$.

When there are four element clusters, first receive signals $\Phi ij$ are sequentially stored while selecting one of 16 combinations of transmission and reception, as shown in FIG. 7.

[Formula 3]

$$\Psi(F) = \sum_{i=1}^{M} \sum_{j=1}^{M} \Phi ij \quad (3)$$

Finally, as shown by formula (3), all the first receive signals $\Phi ij$ are combined (summed up) to derive a second receive signal $\Psi(F)$ for the focal point F.

Image display in the ultrasonic testing apparatus according to the present embodiment will be described below with reference to FIGS. 8 to 10.

Figure 8:
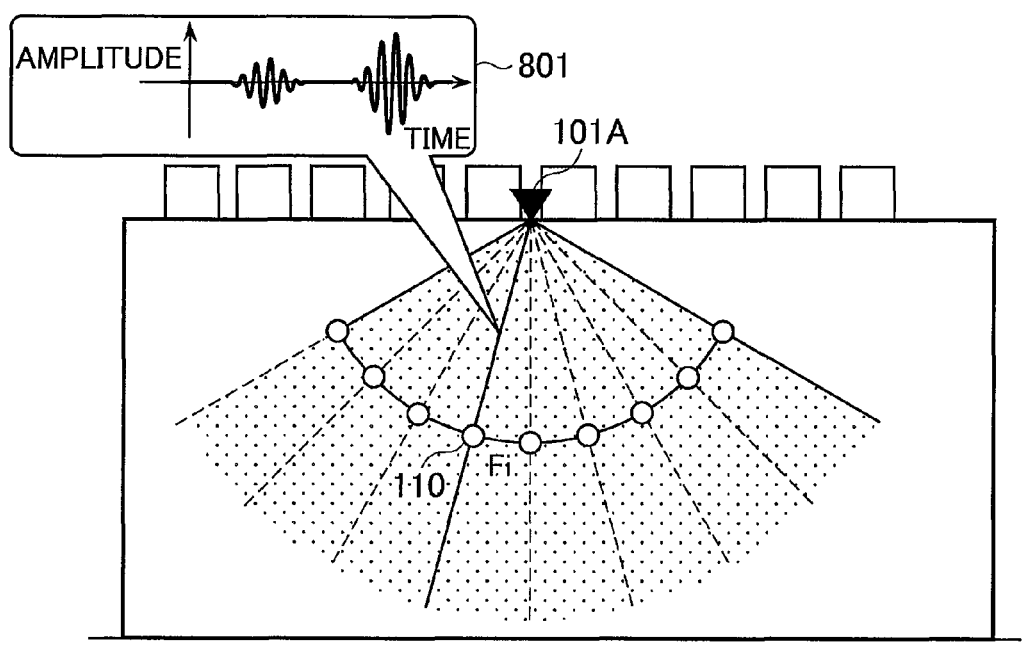
FIG. 8 illustrates image display in the ultrasonic testing apparatus according to the first embodiment of the present invention.
Figure 9:
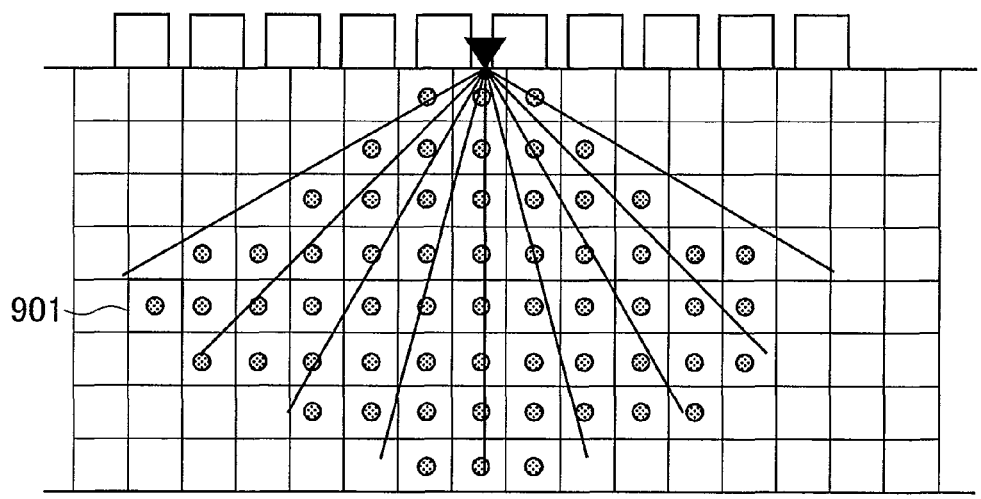
FIG. 9 illustrates image display in the ultrasonic testing apparatus according to the first embodiment of the present invention.
Figure 10:
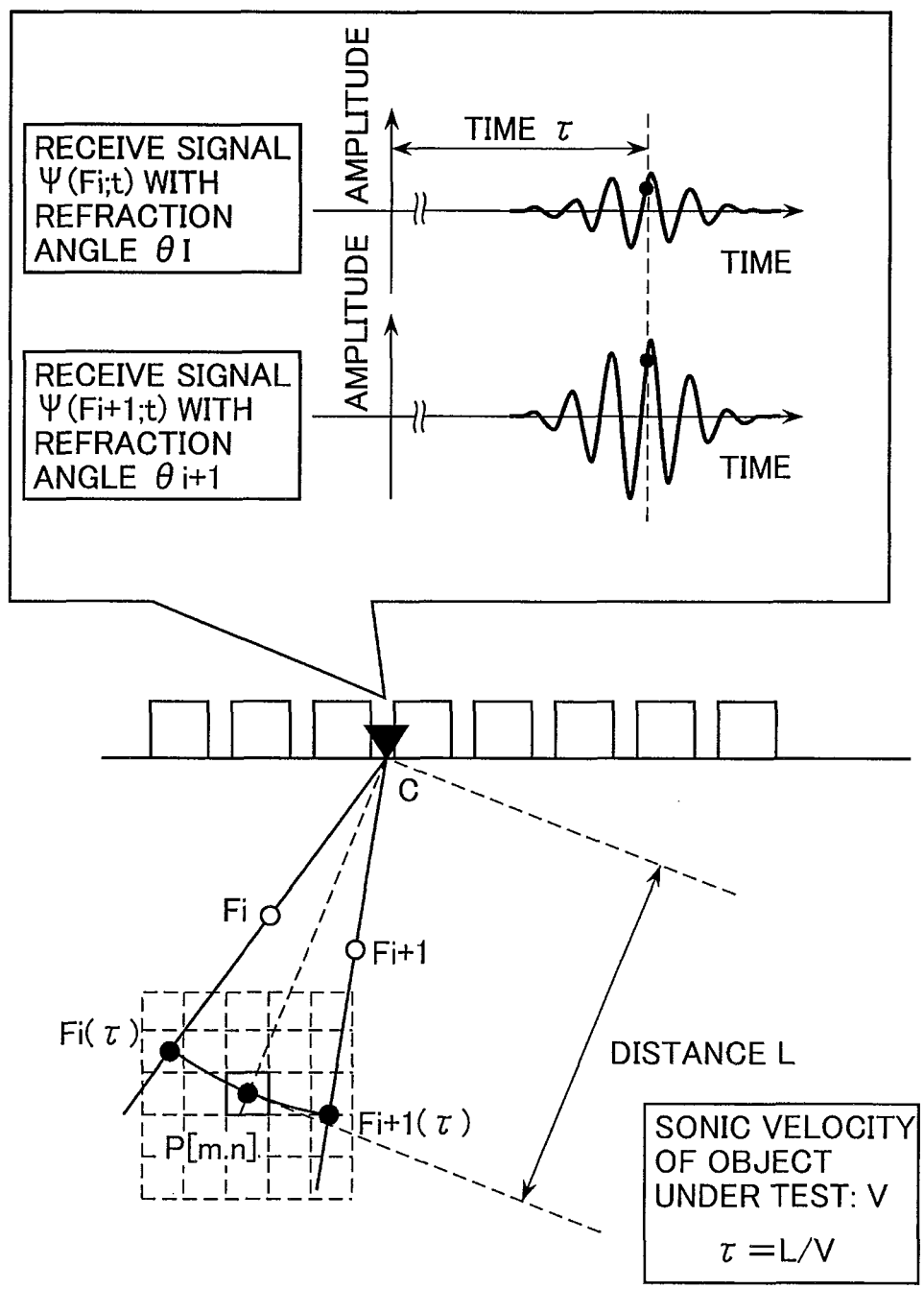
FIG. 10 illustrates image display in the ultrasonic testing apparatus according to the first embodiment of the present invention.

FIGS. 8 to 10 illustrate image display in the ultrasonic testing apparatus according to the first embodiment of the present invention.

In actual testing, since a plurality of focal positions are two- or three-dimensionally scanned, a plurality of second receive signals $\Psi(F)$ are combined for each focal position, as shown in FIG. 8. The second receive signal $\Psi(F)$ can be represented as a graph 801 when the vertical axis is assigned amplitude and the horizontal axis is assigned time. Hereinafter, a value of a second receive signal $\Psi(Fi)$ set at an i-th focal point Fi at a time t is represented by $\Psi(Fi;t)$.

The display unit 103 displays the second receive signal $\Psi(Fi;t)$ as a two- or three-dimensional image.

In order to constitute a two- or three-dimensional image from the second receive signal $\Psi(F)$, a pixel value for a pixel 901 is obtained and then pixel values between second receive signals $\Psi$ are interpolated, as shown in FIG. 9.

An exemplary method for calculating a pixel value will be described below with reference to FIG. 10 and formula (4).

The first receive signals $\Phi ij$ are combined (summed up) to derive a second receive signal for the focal point F, $\Psi(F)$. Since each pixel is sandwiched by two receive signals ($\Psi(Fi;t)$ and $\Psi(Fi+1;t)$) corresponding to a certain focus point (Fi and Fi+1, respectively) as shown in FIG. 9, a pixel value can be obtained by using the second receive signals $\Psi$. Specifically, as shown in FIG. 10, a distance L between a reference position C and a certain pixel P [m,n] is divided by the sonic velocity V in an object under test to obtain a propagation time τ=L/V. Then, signals Ψ(Fi;τ) and Ψ(Fi+1;τ) corresponding to time τ, as well as a point Fi(τ) corresponding to the distance L from the reference position C through a respective focal point Fi are obtained. A weight W(i) is obtained from the ratio of the length of a line FiFi+1 defined by the point Fi(τ) and a point Fi+1(τ) to the length of a line PFi+1 defined by a pixel point P[m,n] and the point Fi+1(τ) (Formula (4)).

[Formula 4]

$$\Psi(P[m, n]; \tau) = W(i) \times \Psi(Fi; \tau) + W(i + 1) \times \Psi(Fi + 1; \tau) \quad (4)$$

where $$W(i) = \frac{\overline{PFi + 1(\tau)}}{\overline{Fi(\tau)Fi + 1(\tau)}}$$

The weight W(i) is multiplied by Ψ and then subjected to weighted averaging to obtain Ψ(P[m,n];τ). The testing process repeats this processing for each pixel to obtain two- or three-dimensional pixel values. Then, testing results are displayed, for example, as monochrome or color images according to the size of the pixel values. Resultant images are displayed, for example, as a sectional view 103B in the direction of plate thickness of FIG. 1 and a graph 103C illustrating a relation between time and amplitude.

The ultrasonic testing method in the ultrasonic testing apparatus according to the present embodiment will be described below with reference to FIGS. 11 to 13.

Figure 11:
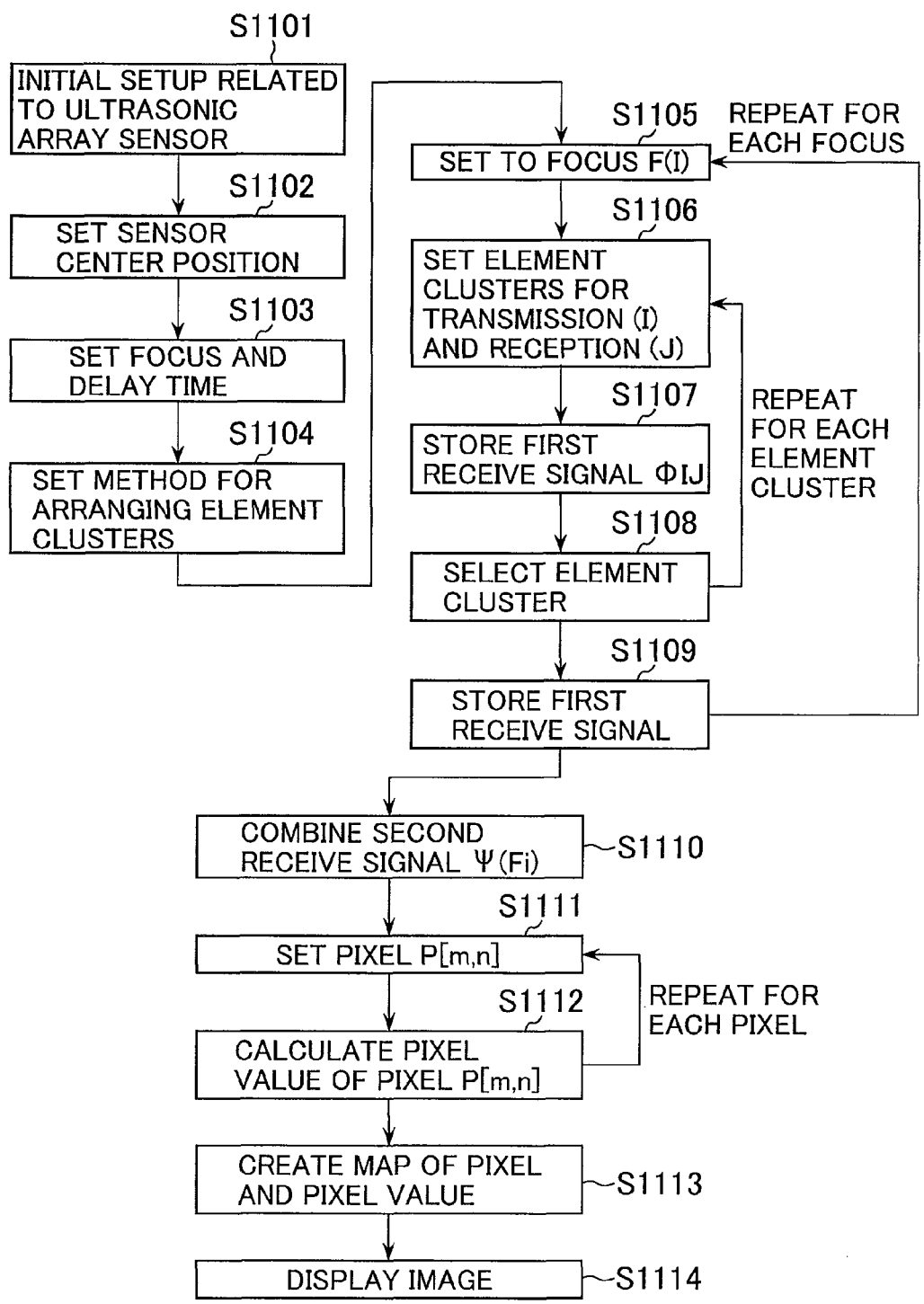
FIG. 11 is a flow chart illustrating detailed processing of an ultrasonic testing method in the ultrasonic testing apparatus according to the first embodiment of the present invention.

FIG. 11 is a flow chart illustrating detailed processing of the ultrasonic testing method in the ultrasonic testing apparatus according to the first embodiment of the present invention. FIGS. 12 and 13 illustrate array transducers used for the ultrasonic testing apparatus according to the first embodiment of the present invention.

Detailed processing of the ultrasonic testing method according to the present embodiment in FIG. 11 is roughly divided into three blocks.

The ultrasonic array transducer 101 composed of N piezoelectric elements is disposed on the object under test 100. A first block (steps S1101 to S1104) relates to initial setup for the ultrasonic array transducer 101. In Step S1101 (initial setup), the testing process sets the ultrasonic velocity of the object under test, the number of piezoelectric elements (N), and arrangements and interval of piezoelectric elements 104 composing the array transducer 101.

Figure 12:
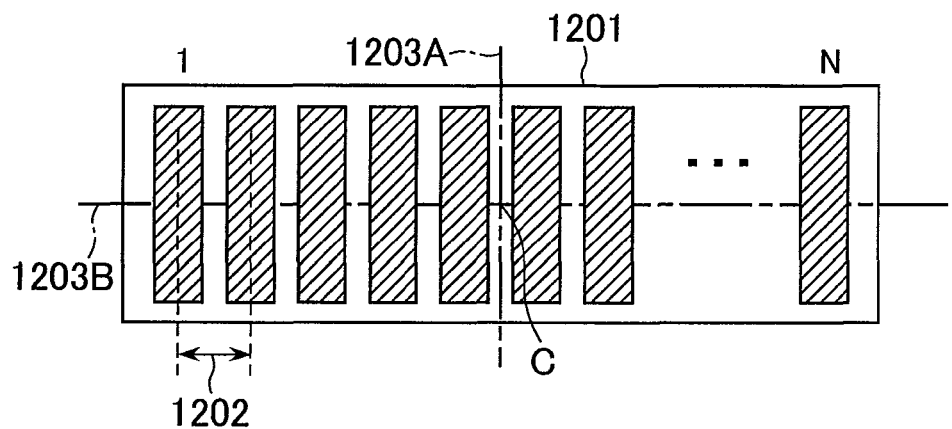
FIG. 12 illustrates an array transducer used in the ultrasonic testing apparatus according to the first embodiment of the present invention.

In the case of an array transducer 1201 composed of one-dimensionally arranged piezoelectric elements, the position of piezoelectric elements distributed in the array transducer 1201 can be grasped by setting an interval 1202 and arrangements of N piezoelectric elements, as shown in FIG. 12.

Figure 13:
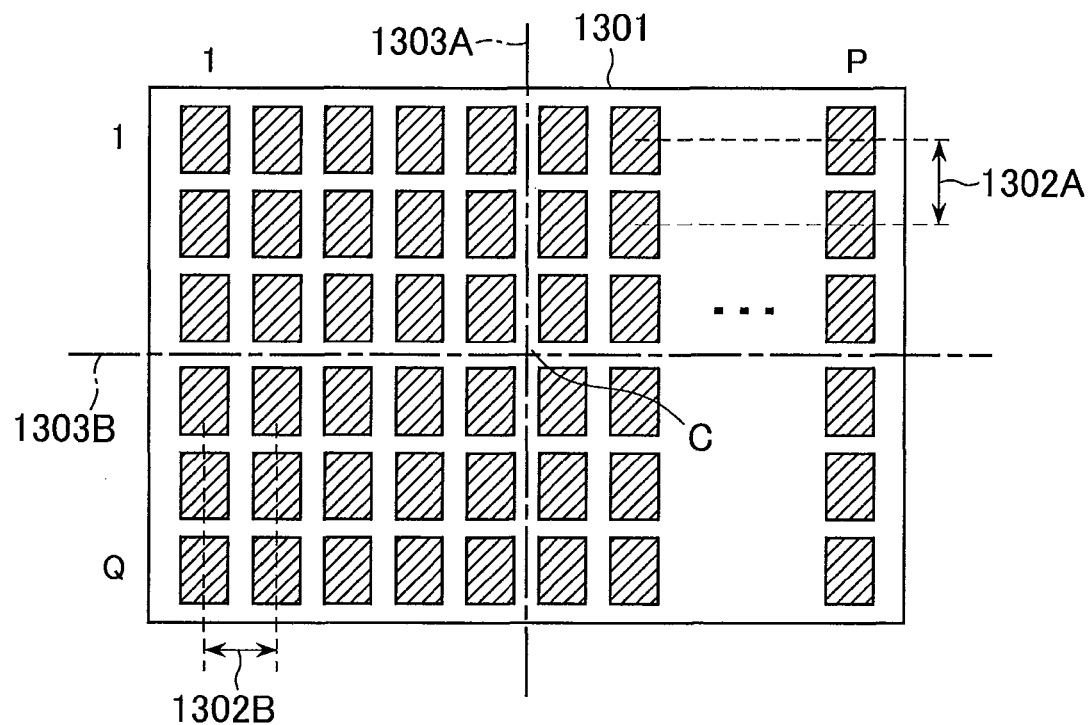
FIG. 13 illustrates an array transducer used in the ultrasonic testing apparatus according to the first embodiment of the present invention.

In the case of an array transducer 1301 composed of two-dimensionally arranged piezoelectric elements, the position of piezoelectric elements distributed in the array transducer 1301 can be grasped by setting intervals 1302 and 1303 and arrangements of N piezoelectric elements (N=P columns×Q rows), as shown in FIG. 13.

The testing process sets a delay time and a sensor center position to be used as a reference for image display to these N piezoelectric elements (step S1102 of FIG. 11). Generally, as shown in FIGS. 12 and 13, the testing process sets a center (an intersection of center lines 1203A and 1203B of FIG. 12 or an intersection of center lines 1303A and 1303B of FIG. 13) of piezoelectric elements as a sensor center position C.

Then, as described with reference to FIGS. 2 to 5, the testing process calculates a delay time pattern for each element of the array transducer with respect to a single or a plurality of focal points F (step S1103).

The testing process sets an element or element group (element cluster) to be used for transmission and reception when storing a first receive signal (step S1104). For example, as shown in FIG. 6, suppose a case where N piezoelectric elements are grouped into four different element groups (A to D). For example, with the one-dimensionally arranged array transducer 1201 of FIG. 12 composed of N(=256) elements, element #1 to #64 are grouped as the cluster A, element #65 to #128 are grouped as the cluster B, element #129 to #196 are grouped as the cluster C, and element #197 to #256 are grouped as the cluster D. With a two-dimensionally arranged array transducer 1301 of FIG. 13 composed of N(=256) elements (N=P columns×Q rows, P=Q=16), column #1 to #8 (P=1-8) and row #1 to #8 (Q=1-8) are grouped as the cluster A, column #1 to #8 (P=1-8) and row #9 to #16 (Q=9-16) are grouped as the cluster B, column #9 to #16 (P=9-16) and row #1 to #8 (Q=1-8) are grouped as the cluster C, and column #9 to #16 (P=9-16) and row #9 to #16 (Q=9-16) are grouped as the cluster D.

A second block (steps S1105 to S1109) relates to processing of first receive signals.

The testing process stores the first receive signal for the focal point F used for delay time setup. First of all, the testing process sets a delay time at a certain focal point F(i) (step S1105). Then, the testing process sets an element cluster for transmission and an element cluster for reception. For example, when there are four different element clusters A to D, the testing process sets the cluster A for transmission and the cluster A for reception (step S1106). Then, the testing process stores a receive signal by using the element cluster for transmission and the element cluster for reception (step S1107), and changes the element clusters for transmission and reception (step S1108). The testing process repeats steps S1106 to S1108 for each element cluster, and stores the first receive signal for a certain focal position F (step S1109). For example, when there are four element clusters, the testing process stores 16(4×4) first receive signals Φij, as shown in FIG. 7. When there is a plurality of focal points, the testing process repeats steps S1105 to S1109 for each focal point to store first receive signals corresponding to the number of focal points.

A third block (steps S1110 to S1114) relates to processing of second receive signals and display.

First of all, the testing process combines (sums up) first receive signals Φ based on formula (3) to derive a second receive signal Ψ (step S1110). Then, the testing process sets a range (a pixel) for image display (step S1111). Then, as mentioned above with reference to FIGS. 8 to 10 and formula (4), the testing process calculates a pixel value for a pixel P through interpolation based on second receive signals Ψ corresponding to the number of focal points (step S1112). The testing process maps a pixel value corresponding to the pixel P (step S1113), and displays it on the image display unit 103 (step S1114).

Then, an effective range of a focal beam obtained by the ultrasonic testing apparatus according to the present embodiment will be described below with reference to FIG. 14.

Figure 14:
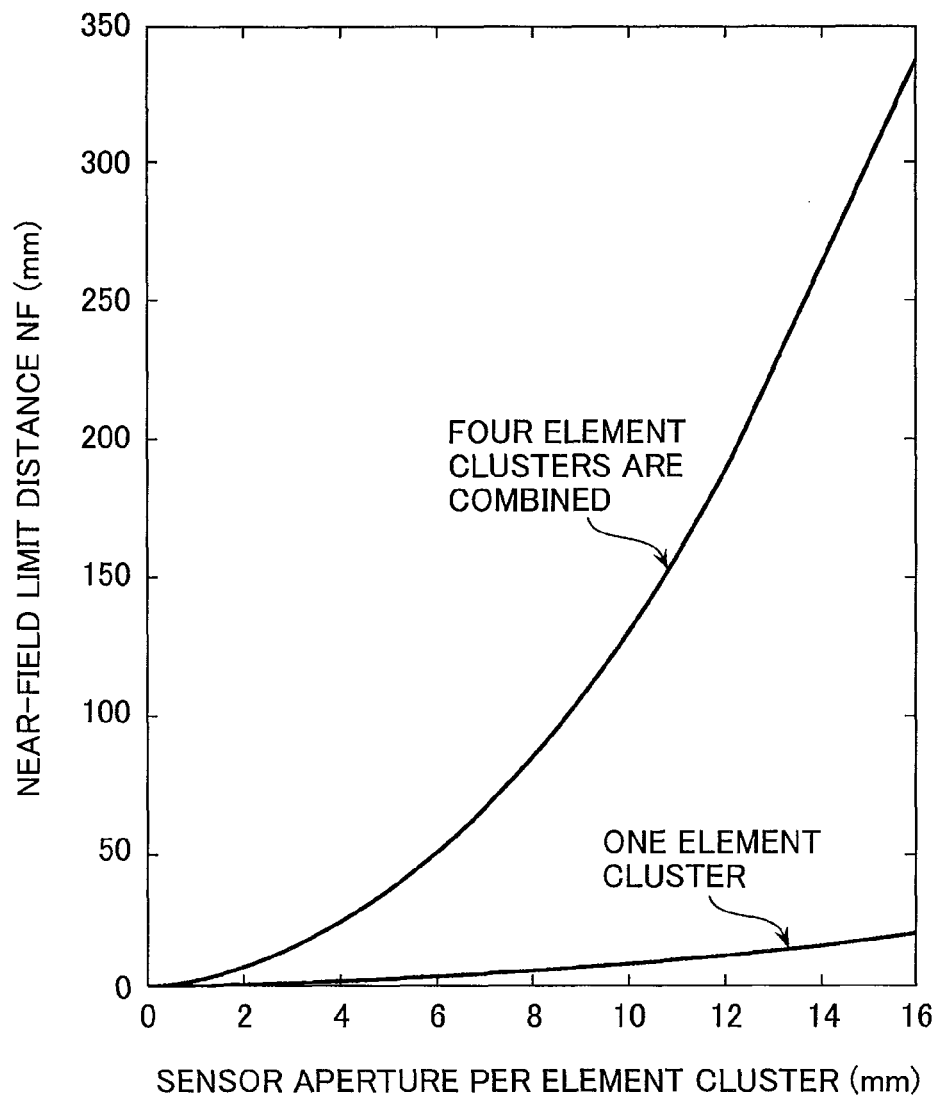
FIG. 14 illustrates an effective range of a focal beam obtained in the ultrasonic testing apparatus according to the first embodiment of the present invention.

FIG. 14 illustrates the effective range of the focal beam obtained by the ultrasonic testing apparatus according to the first embodiment of the present invention.

FIG. 14 illustrates the effective range (near-sound-field limit distance NF) of the focal beam obtained by the present embodiment. The testing process performs calculation with a frequency of 2 MHz and a sonic velocity of steel material of 6000 m/s.

When there is one element cluster, the effective focused beam is obtained at a depth less than 50 mm even if the element cluster is 16 mm wide.

According to the present embodiment having four element clusters, when the aperture of one element cluster is 16 mm wide (sensor width), the substantial sensor aperture becomes 64 mm wide by combining a plurality of receive signals. Therefore, an ultrasonic beam is sufficiently effective at a depth of 300 mm or more.

As mentioned above, the present embodiment combines the pulser and receiver circuit configuration suitable for element clusters for first receive signals with signal combination processing for second receive signals. This enables imaging by driving a number of piezoelectric elements while maintaining the apparatus compact as well as use the focal beam with a large substantial sensor aperture, thus obtaining testing images with high resolution and high S/N ratio.

Configuration and operation of an ultrasonic testing apparatus according to a second embodiment of the present invention will be described below with reference to FIGS. 15 to 17. The configuration of the ultrasonic testing apparatus according to the present embodiment is the same as that shown in FIG. 1.

First of all, a sensor center position setup in the ultrasonic testing apparatus according to the present embodiment will be described below with reference to FIGS. 15 and 16.

Figure 15:
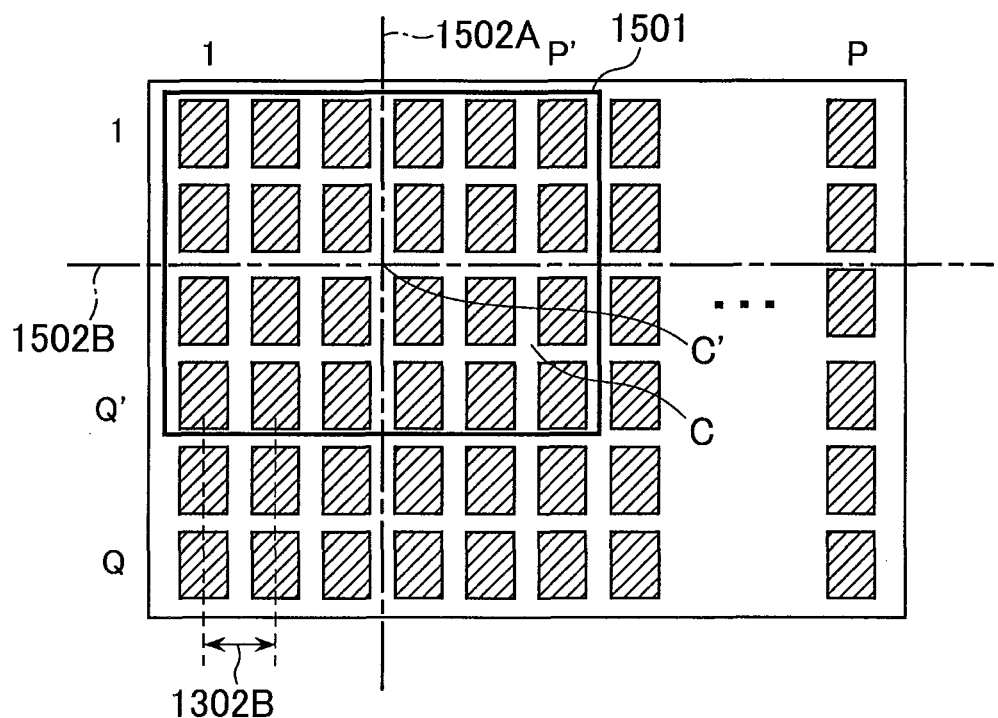
FIG. 15 illustrates a sensor center position setup in an ultrasonic testing apparatus according to a second embodiment of the present invention.
Figure 16:
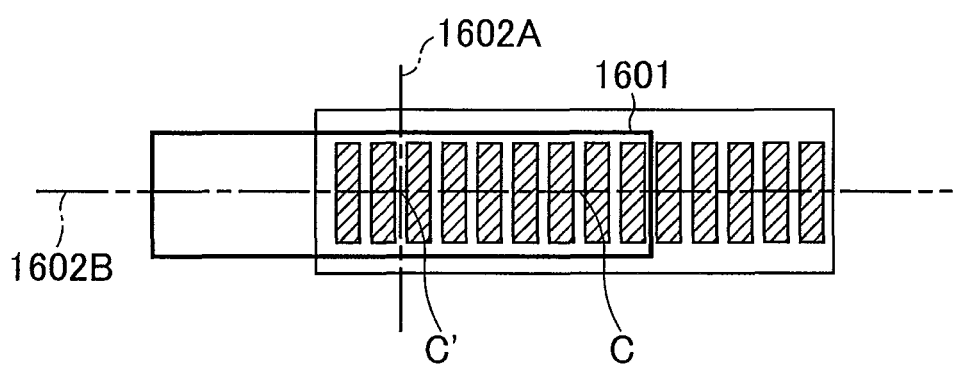
FIG. 16 illustrates a sensor center position setup in the ultrasonic testing apparatus according to the second embodiment of the present invention.

FIGS. 15 and 16 illustrate a sensor center position setup in the ultrasonic testing apparatus according to the second embodiment of the present invention.

With the present embodiment, although processing flow is the same as that of the first embodiment, the sensor center position setup (step S1102 of the flow chart in FIG. 11) is extended.

Although all the piezoelectric elements composing an ultrasonic array transducer are grouped into a plurality of element clusters in the first embodiment, FIG. 15 shows a case where a part of piezoelectric elements composing the array transducer are partially used for element cluster setup. With an array transducer composed of two-dimensionally arranged N(=P×Q) piezoelectric elements, for example, only column #1 to #P' and row #1 to #Q' are used for testing, and an intersection of two center lines 1502A and 1502B for a region of P'×Q' piezoelectric elements is set as a sensor center position C'. In this case, it can be considered that the region of P'×Q' piezoelectric elements serves as a virtual array transducer. This also applies to a one-dimensional array although an exemplary two-dimensionally array is shown in FIG. 15.

Further, as shown in FIG. 16, a virtual array transducer may be set to the outside of a real ultrasonic array transducer. In this case, a portion shown as a region 1601 serves as a virtual array transducer, and an intersection of two center lines 1602A and 1602B is set as a sensor center position C'.

If flexibility is given to a setup of sensor center position (a reference for delay time and image display) in this way, desired piezoelectric elements can be used to constitute a virtual array transducer depending on the thickness of an object under test. Specifically, when imaging a shallow (thin) region of the object under test, the number of piezoelectric elements is decreased. When imaging a deep (thick) region of the object under test, the number of piezoelectric elements is increased. This makes it possible, for example, to maintain a constant resolution of images in the depth direction.

Another exemplary sensor center position setup in the ultrasonic testing apparatus according to the present embodiment will be described below with reference to FIG. 17.

Figure 17:
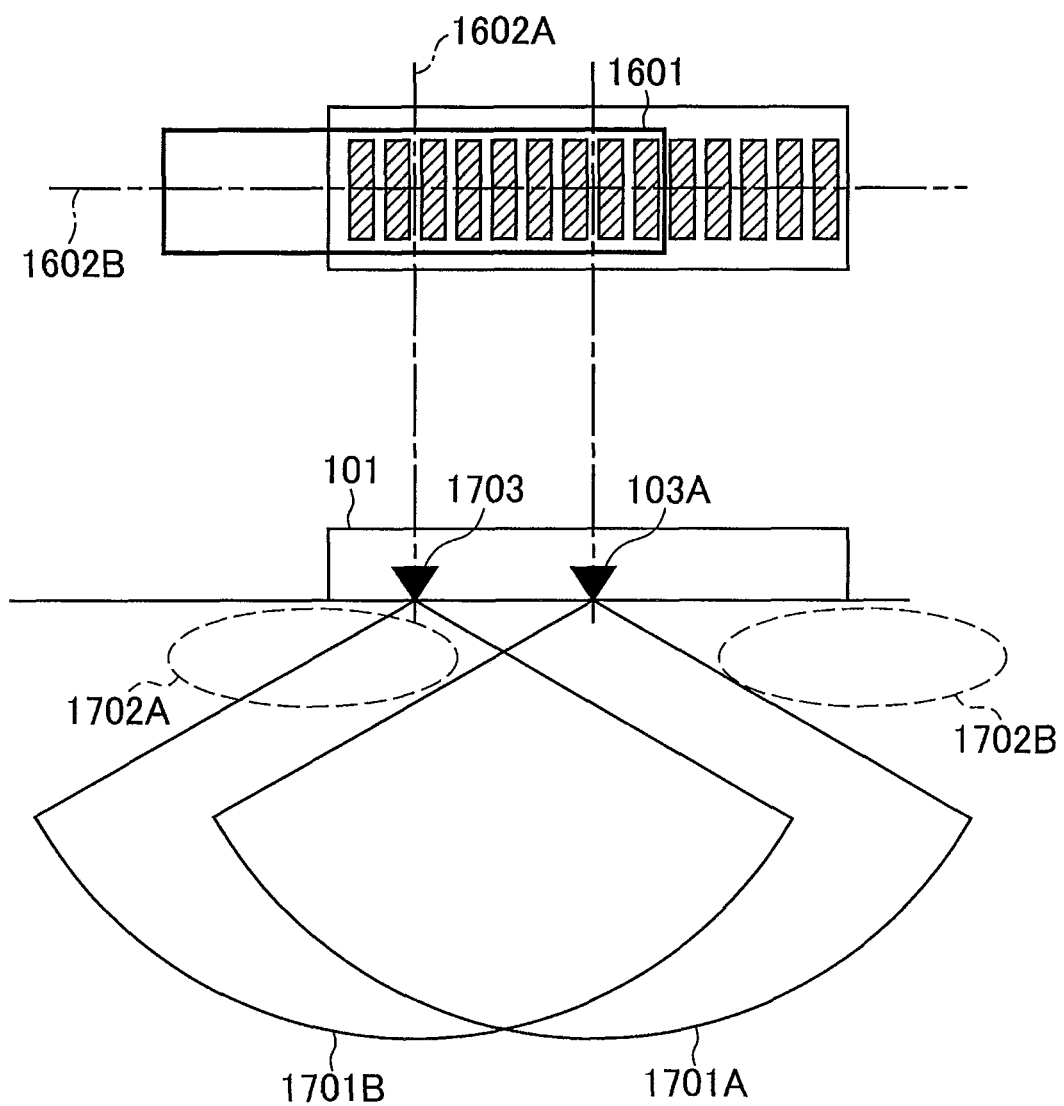
FIG. 17 illustrates a sensor center position setup in the ultrasonic testing apparatus according to the second embodiment of the present invention.

FIG. 17 illustrates a sensor center position setup in the ultrasonic testing apparatus according to the second embodiment of the present invention.

An image over a wider range can be obtained by setting a virtual array transducer to the outside of a real array transducer. An image over a wide range will be schematically described below with reference to FIG. 17.

When the array transducer 101 performs imaging at the sensor center position 103A thereof according to the first embodiment, images can be obtained within a range of a fan 1701A but pixel values cannot be obtained in regions 1702A and 1702B. When the virtual array transducer is set in the region 1601, the sensor center position can be set to a point 1703, allowing images to be obtained within a range of a fan 1701B. Thus, imaging can be performed over a wider range. For example, suppose a case where an array transducer is disposed on the outer circumference of a bent pipe. If the sensor cannot be brought any closer to the bent portion on the pipe, setting a virtual array transducer as shown in FIG. 17 makes it possible to test portions closer to the bent portion. This effect of obtaining images over a wider range is also applicable to a case where the elements of the array transducer are partially used as a virtual array transducer, as shown in FIG. 15.

As mentioned above, according to the present embodiment, setting a virtual array transducer as well as a relevant sensor center position makes it possible to adjust resolution in the depth direction, allowing imaging over a wider range.

Configuration and operation of an ultrasonic testing apparatus according to a third embodiment of the present invention will be described below with reference to FIGS. 18 to 21. The configuration of the ultrasonic testing apparatus according to the present embodiment is the same as that shown in FIG. 1.

Figures 18, 19:
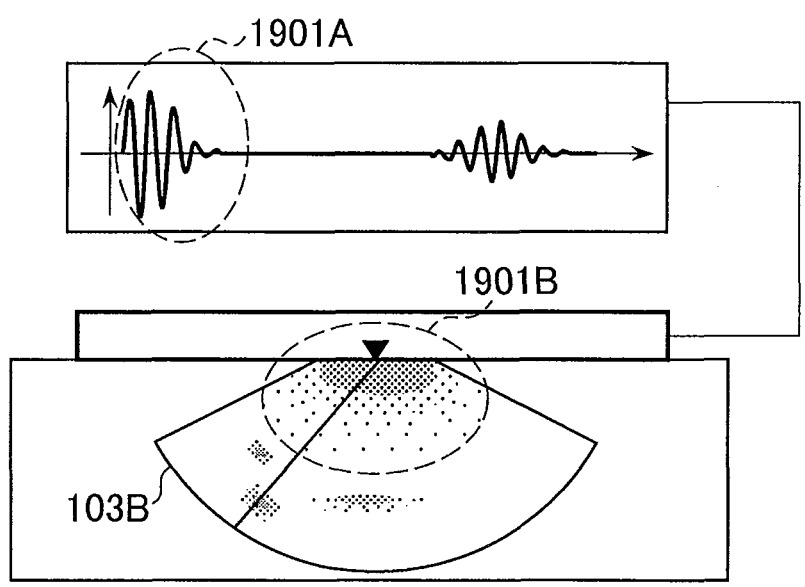
FIG. 18 illustrates element cluster combination setups in an ultrasonic testing apparatus according to a third embodiment of the present invention.
FIG. 19 illustrates a display screen in the ultrasonic testing apparatus according to the third embodiment of the present invention.
Figures 20, 21:
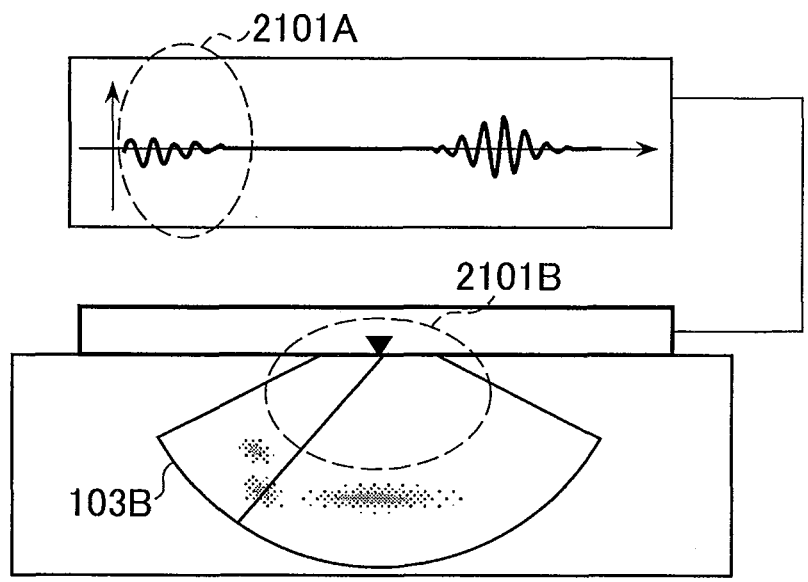
FIG. 20 illustrates element cluster combination setups in the ultrasonic testing apparatus according to the third embodiment of the present invention.
FIG. 21 illustrates the display screen in the ultrasonic testing apparatus according to the third embodiment of the present invention.

FIGS. 18 and 20 illustrate element cluster combination setups in the ultrasonic testing apparatus according to the third embodiment of the present invention. FIGS. 19 and 21 illustrate display screens in the ultrasonic testing apparatus according to the third embodiment of the present invention.

With the present embodiment, the array transducer 101 is composed of four element clusters.

FIGS. 18 and 20 illustrate exemplary element cluster combination setups used for transmission and reception. FIG. 18 illustrates a case where a second receive signal Ψ is derived from all the 16 first receive signals Φ obtained by the four element clusters. These combinations of element clusters are the same as those shown in FIG. 7.

FIG. 20 illustrates a case where a second receive signal Ψ is derived from 12 first receive signals Φ obtained by combinations of different element clusters for transmission and reception. Combinations marked ○ are used but combinations marked X are not.

When the same element cluster is used both for transmission and reception, a transmission signal drifting into the same element (or the same element cluster) causes signals (1901A and 1901B of FIG. 19) which serve as noise forming a dead zone in the vicinity of the array transducer. When different elements or element clusters are used for transmission and reception, signals (2101A and 2101B of FIG. 21) accompanying transmission can be reduced, resulting in a reduced dead zone.

On the other hand, when the element cluster combinations of FIG. 18 are used, the sensitivity can be increased allowing deeper portions to be tested.

Therefore, for example, deep portions are initially tested by using the element cluster combinations of FIG. 18, and if a detected defect (a crack or the like) extends to a shallower portion, the element cluster combinations are changed to those of FIG. 20 to enable shallower portions to be subsequently tested.

According to the present embodiment, selecting a combination of different element clusters for transmission and/or reception, each element cluster being composed of a single or a plurality of elements, makes it possible to separate element(s) (element clusters) for transmission from element(s) (element clusters) for reception, thus reducing noise signals (such as a transmitting pulse, an echo in a shoe, etc.) accompanying ultrasonic transmission.

Configuration and operation of a three-dimensional ultrasonic imaging apparatus according to a fourth embodiment of the present invention will be described below with reference to FIGS. 22 to 30.

First of all, the configuration of the three-dimensional ultrasonic imaging apparatus according to the present embodiment will be described below with reference to FIG. 22.

Figure 22:
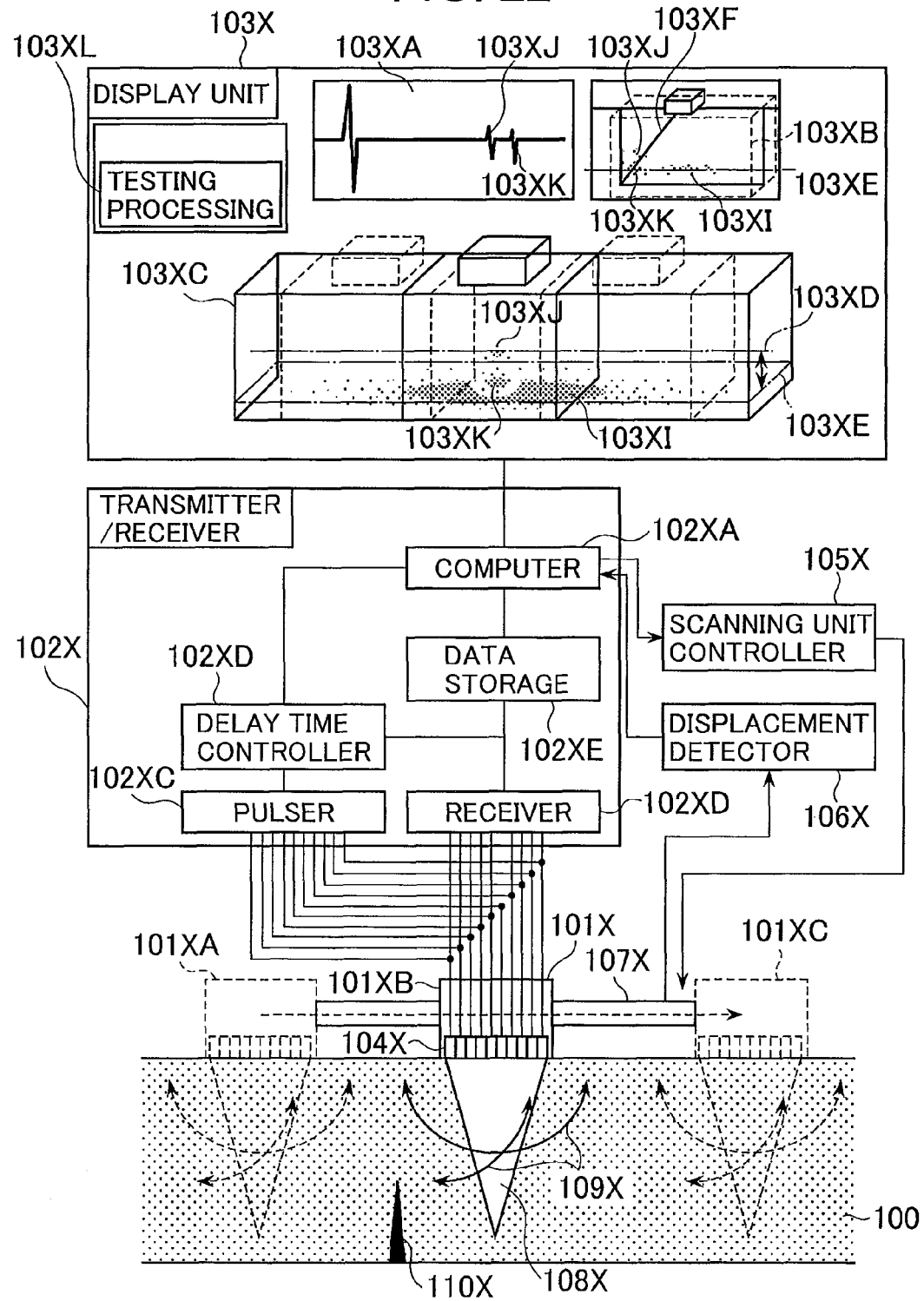
FIG. 22 is a block diagram illustrating a configuration of a three-dimensional ultrasonic imaging apparatus according to a fourth embodiment of the present invention.

FIG. 22 is a block diagram illustrating the configuration of the three-dimensional ultrasonic imaging apparatus according to the fourth embodiment of the present invention.

The three-dimensional ultrasonic imaging apparatus according to the present embodiment includes: a two-dimensional array ultrasonic sensor 101X configured to transmit an ultrasonic wave to an object under test 100; a transmitter/receiver 102X; a display unit 103X configured to display a receive signal and three-dimensional testing data; a scanning unit controller 105X configured to feed the two-dimensional array ultrasonic sensor 101X; a displacement detector 106X configured to detect a displacement of the ultrasonic sensor 101X; and a sensor scanning unit 107 configured to feed the two-dimensional array ultrasonic sensor 101X.

The array ultrasonic sensor 101X is composed of piezoelectric elements 104X each transmitting an ultrasonic wave as shown in FIG. 22. The array ultrasonic sensor 101X is set on a testing surface of an object under test 100, transmits an ultrasonic wave 108X by a drive signal supplied from the transmitter/receiver 102X, propagates the ultrasonic wave 108X in the object under test 100, measures a reflected echo therefrom, and supplies a receive signal to the transmitter/receiver 102.

The transmitter/receiver 102X includes a computer 102XA, a delay time controller 102XB, a pulser 102XC, a receiver 102XD, and data storage 102XE. The pulser 102XC supplies a drive signal to an array transducer 101X, and the receiver 102XD processes the receive signal received from the array ultrasonic sensor 101X. The computer 102XA controls the delay time controller 102XB, the pulser 102XC, the receiver 102XD, and the data storage 102XE to perform necessary operations.

The delay time controller 102XB controls the timing of drive signal output from the pulser 102XC as well as the timing of receive signal input to the receiver 102XD to attain operations of the two-dimensional array ultrasonic sensor 101 employing the phased array method. The two-dimensional array ultrasonic sensor 101X employing the phased array method controls a focal depth of the ultrasonic wave 108X and at the same time three-dimensionally controls its beam angle 109X in the object under test 100 during transmission and reception of the ultrasonic wave 108X.

The data storage 102XE processes the receive signal supplied from the receiver 102XD and then supplies it to the computer 102XA. The computer 102XA processes the stored testing data and then displays the data on the display unit 103.

Processing in the computer 102XA and operation of the display unit 103X will be described in detail later. The computer 102XA combines waveforms obtained by the piezoelectric elements in relation to a delay time, converts a waveform for each beam angle of each ultrasonic wave to three-dimensional testing data, and displays three-dimensional testing data 103XB on the display unit 103X.

Further, the computer 102XA combines (sums up or averages) a plurality of pieces of three-dimensional testing data 103XB obtained at each position according to operations of the scanning unit controller 105X and the displacement detector 106X to be mentioned later, and displays the combined three-dimensional testing data as a three-dimensional processing image 103XC on the display unit 103X. The display unit 103X displays three-dimensional testing data as mentioned above, and is provided with a function to display a receive waveform 103XA corresponding to a position at a desired ultrasonic beam angle 103X F in testing data.

FIG. 22 illustrates a case where a defect 110X exists on the bottom surface of the object under test 100. In this case, a defect corner echo 103XK, a defect tip echo 103XJ, and a bottom echo 103XI of the object under test are observed at a bottom position 103XE in the three-dimensional testing data 103XB and the three-dimensional processing image 103XC. When sizing the depth of the defect on the bottom surface, the distance between the bottom position 103XE and a defect tip echo position 103XD obtained in the three-dimensional processing data 103XC is used. Also in a combined waveform 103XA at a desired ultrasonic beam angle, reflected echoes 103XJ and 103XK corresponding to these echoes are observed.

A position controller of the scanning unit controller 105X receives a movement signal, including moving speed and displacement, from the computer 102XA, and drives a sensor moving unit 107X based on this signal to move the set position of the two-dimensional array ultrasonic sensor 101X. The sensor moving unit 107X is connected to the displacement detector 106X to measure an actual displacement of the array ultrasonic sensor 101X. FIG. 22 illustrates a case where the array ultrasonic sensor 101X moves a testing start position 101XA (a set position of the array ultrasonic sensor 101X at the start of testing) to a testing end position 101XC (a set position of the array ultrasonic sensor 101X at the end of testing).

A measured displacement is sent to the computer 102XA and then used to process testing data. A displacement at each testing position of the ultrasonic sensor 101X is measured by the displacement detector 106X, and the displacement is used in the computer 102XA to make a shift in the three-dimensional testing data during data combination (summation (or averaging)) (details will be described later).

Since the ultrasonic imaging apparatus according to the present embodiment can also perform conventional testing operations based on a two-dimensional array ultrasonic sensor, it is necessary to switch between this operation mode and an operation mode for the above-mentioned three-dimensional testing data combination (summation (or averaging)) processing. The conventional operation mode does not perform the combination processing. In the conventional operation mode, as the two-dimensional array ultrasonic sensor moves, testing data for the same defect is obtained at each testing position. A maximum value of the obtained testing data is displayed as testing data. With the ultrasonic imaging apparatus according to the present embodiment, therefore, the display unit 103X is provided with a processing switching unit as means for selecting processing in the computer 102XA. This processing switching unit selects software processing, and therefore is provided as a switch or button 103XL in the display unit 103X. The processing switching unit 103XL switches between the conventional testing mode and the summation (averaging) processing mode.

Operation of the two-dimensional array ultrasonic sensor used for the three-dimensional ultrasonic imaging apparatus according to the present embodiment will be described below with reference to FIG. 23.

Figure 23:
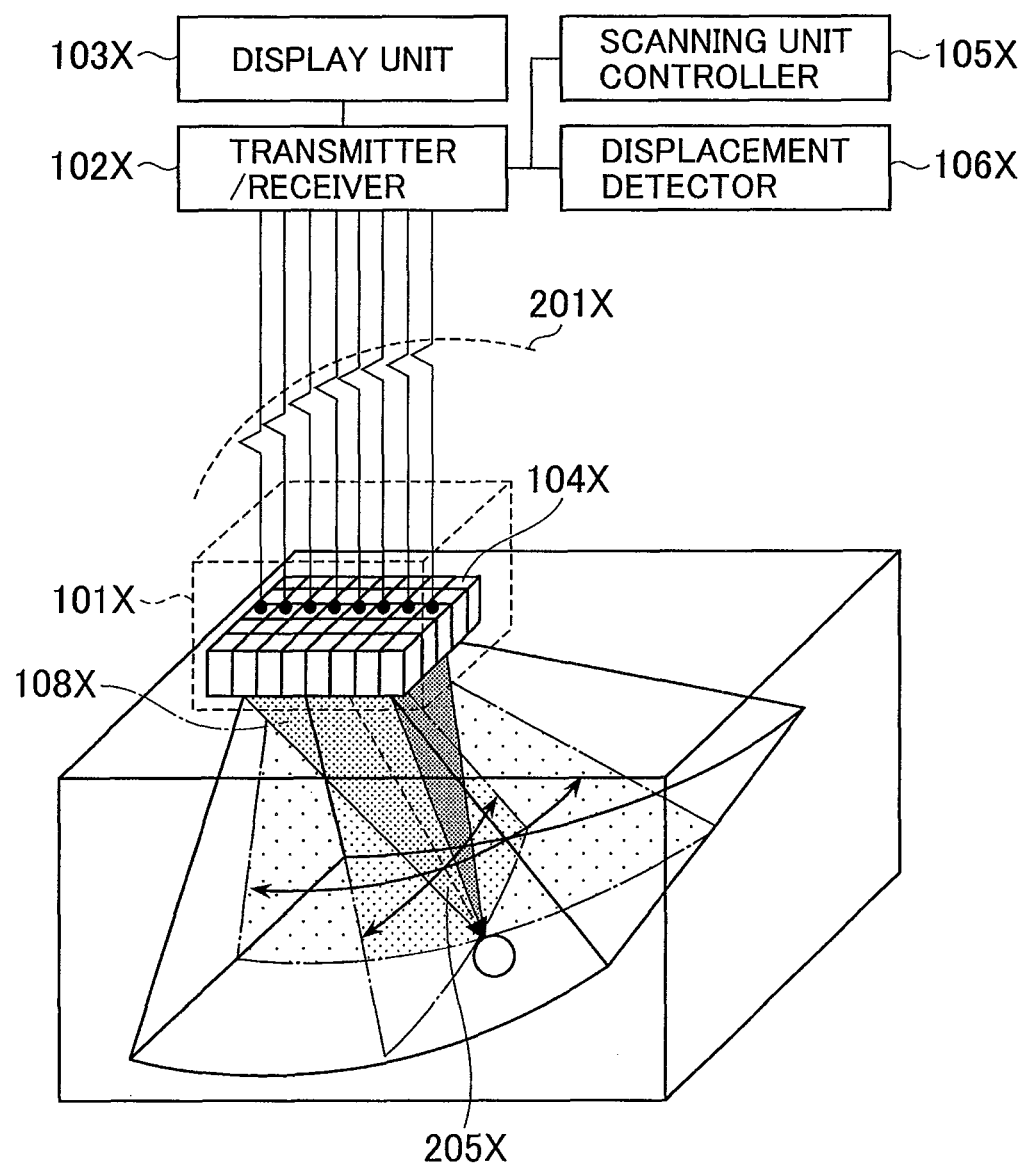
FIG. 23 illustrates an operation of a two-dimensional array ultrasonic sensor used in the three-dimensional ultrasonic imaging apparatus according to the fourth embodiment of the present invention.

FIG. 23 illustrates operation of the two-dimensional array ultrasonic sensor used for the three-dimensional ultrasonic imaging apparatus according to the fourth embodiment of the present invention.

As mentioned above, the array ultrasonic sensor 101X is composed of a plurality of piezoelectric elements 104X. When each of the piezoelectric elements 104X is vibrated due to piezoelectric effect by an electric signal 201X received from the transmitter/receiver 102X, the array ultrasonic sensor 101X transmits an ultrasonic wave 108X. The electric signal 201X supplied to each piezoelectric element drives it in relation to a time delay given from the delay time controller. Wave fronts of the ultrasonic waves transmitted by the piezoelectric elements mutually interfere to form one combined wave front in the course of propagation. The ultrasonic sensor 101X can focus the ultrasonic waves at a desired depth position as well as control a beam angle 205X of the focused ultrasonic wave.

FIG. 23 illustrates operation of the two-dimensional array ultrasonic sensor. FIG. 23 illustrates connections between one row of a plurality of piezoelectric elements 104X and the transmitter/receiver 102X in consideration of the legibility. Actually, all the piezoelectric elements 104X are connected to the transmitter/receiver 102X. Although FIG. 23 illustrates a matrix array transducer composed of piezoelectric elements arranged in a matrix form, any type of two-dimensional array ultrasonic sensor can be used so long as it can three-dimensionally focus the ultrasonic waves inside an object under test and three-dimensionally control the ultrasonic beam angle $\bigcirc$.

With the present embodiment, the focal depth is set in consideration of plate thickness of the object under test. This makes it possible to reduce ultrasonic diffusing attenuation which can be a problem when the synthetic aperture method is applied, thus enabling testing with high S/N ratio even with a long propagation distance of the ultrasonic wave. Further, an ultrasonic beam angle range used for testing is set as a solid angle range within which the ultrasonic wave can be transmitted and received with high sensitivity. A step of the ultrasonic beam angle is set in consideration of a tolerance of the number of delay times that can be set by the delay time controller 102XB.

Operation of three-dimensional ultrasonic scanning (volume scan) by the two-dimensional array in the three-dimensional ultrasonic imaging apparatus according to the present embodiment will be described below with reference to FIGS. 24 to 26

Figure 24:
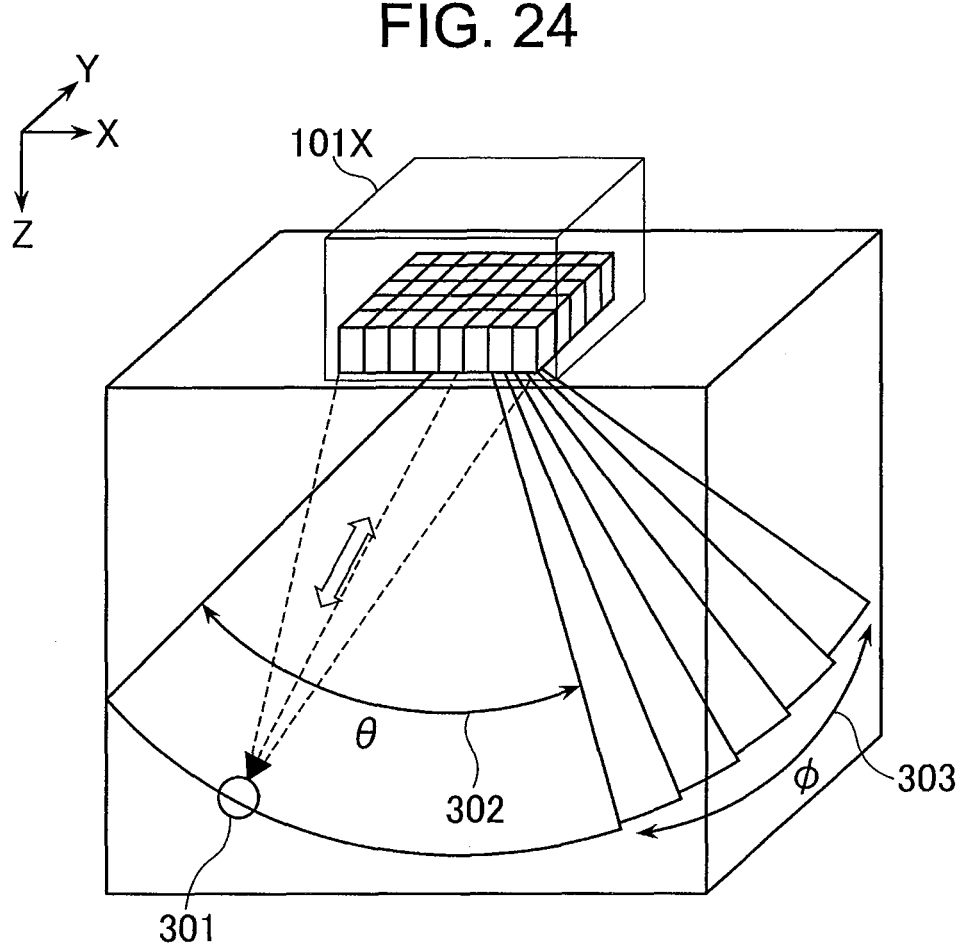
FIG. 24 illustrates an operation of three-dimensional ultrasonic scanning (volume scan) by the two-dimensional array in the three-dimensional ultrasonic imaging apparatus according to the fourth embodiment of the present invention.
Figure 25:
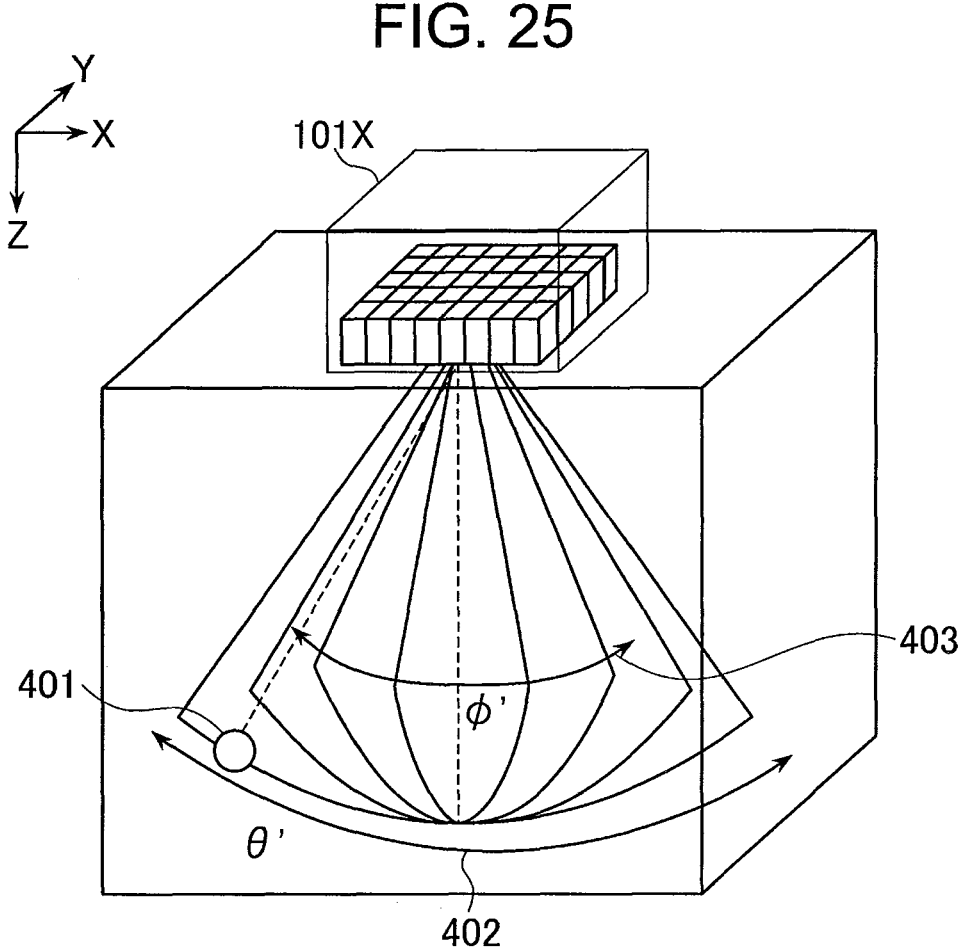
FIG. 25 illustrates an operation of three-dimensional ultrasonic scanning n (volume scan) by the two-dimensional array in the three-dimensional ultrasonic imaging apparatus according to the fourth embodiment of the present invention.
Figure 26:
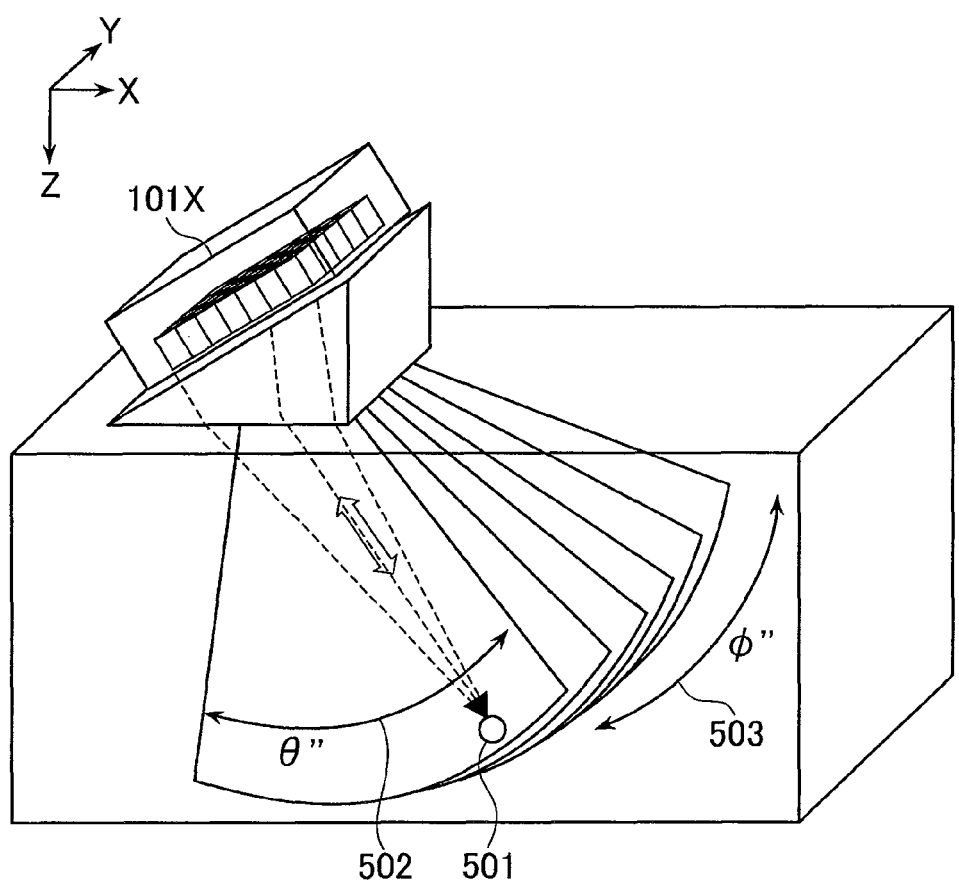
FIG. 26 illustrates an operation of three-dimensional ultrasonic scanning (volume scan) by the two-dimensional array in the three-dimensional ultrasonic imaging apparatus according to the fourth embodiment of the present invention.

FIGS. 24 to 26 illustrate operation of three-dimensional ultrasonic scanning (volume scan) by the two-dimensional array in the three-dimensional ultrasonic imaging apparatus according to the fourth embodiment of the present invention.

The two-dimensional array ultrasonic sensor 101X, while maintaining a constant distance between a reference point (direct under the center thereof) and a focal point, transmits and receives ultrasonic waves so as to focus them within the ultrasonic beam angle range used for testing.

FIG. 24 illustrates swing scanning. While maintaining a constant distance to an ultrasonic focal point 301, the ultrasonic sensor 101X continuously changes an angle θ (in angular steps of Δθ) within an angle range 302 in a certain plane in the three-dimensional space. This process is referred to as sectorial scanning process. Further, the ultrasonic sensor 101X performs the sectorial scanning process for an angle φ (in angular steps of Δφ) within an angle range 303 such that a plane is continuously drawn, thus enabling three-dimensional ultrasonic scanning.

FIG. 25 illustrates rotation scanning. While maintaining a constant distance to an ultrasonic focal point 401, the ultrasonic sensor 101X continuously changes an angle θ' (in angular steps of Δθ') within an angle range 402 in a certain plane in the three-dimensional space. This process is referred to as sectorial scanning process. Further, the ultrasonic sensor 101X performs the sectorial scanning process for a rotating angle φ' (at a rotating angular step Δφ') within a rotating angle range 403. The ultrasonic sensor 101X changes the rotating angle range 403 of φ' from 0 to 180 degrees to enable three-dimensional ultrasonic scanning.

FIG. 26 illustrates wedged swing scanning. Although a wedge (shoe) is used by conventional methods to unify the directivity of ultrasonic waves to a direction in which a defect is easily detected, the two-dimensional array ultrasonic sensor can also use a wedge for testing. Similar to swing scanning shown in FIG. 24, while maintaining a constant distance to an ultrasonic focal point 501, the ultrasonic sensor 101X continuously changes an angle θ" (in angular steps of Δθ") within an angle range 502 in a certain plane in the three-dimensional space (sectorial scanning process). Further, the ultrasonic sensor 101X performs the sectorial scanning process for an angle φ" (in angular steps of Δφ") within an angle range 503 such that a plane is continuously drawn. An optimum three-dimensional ultrasonic scanning method is selected depending on the characteristics and size of a defect.

Processing of three-dimensional testing data in the three-dimensional ultrasonic imaging apparatus according to the present embodiment will be described below with reference to FIGS. 27 and 28.

Figure 27:
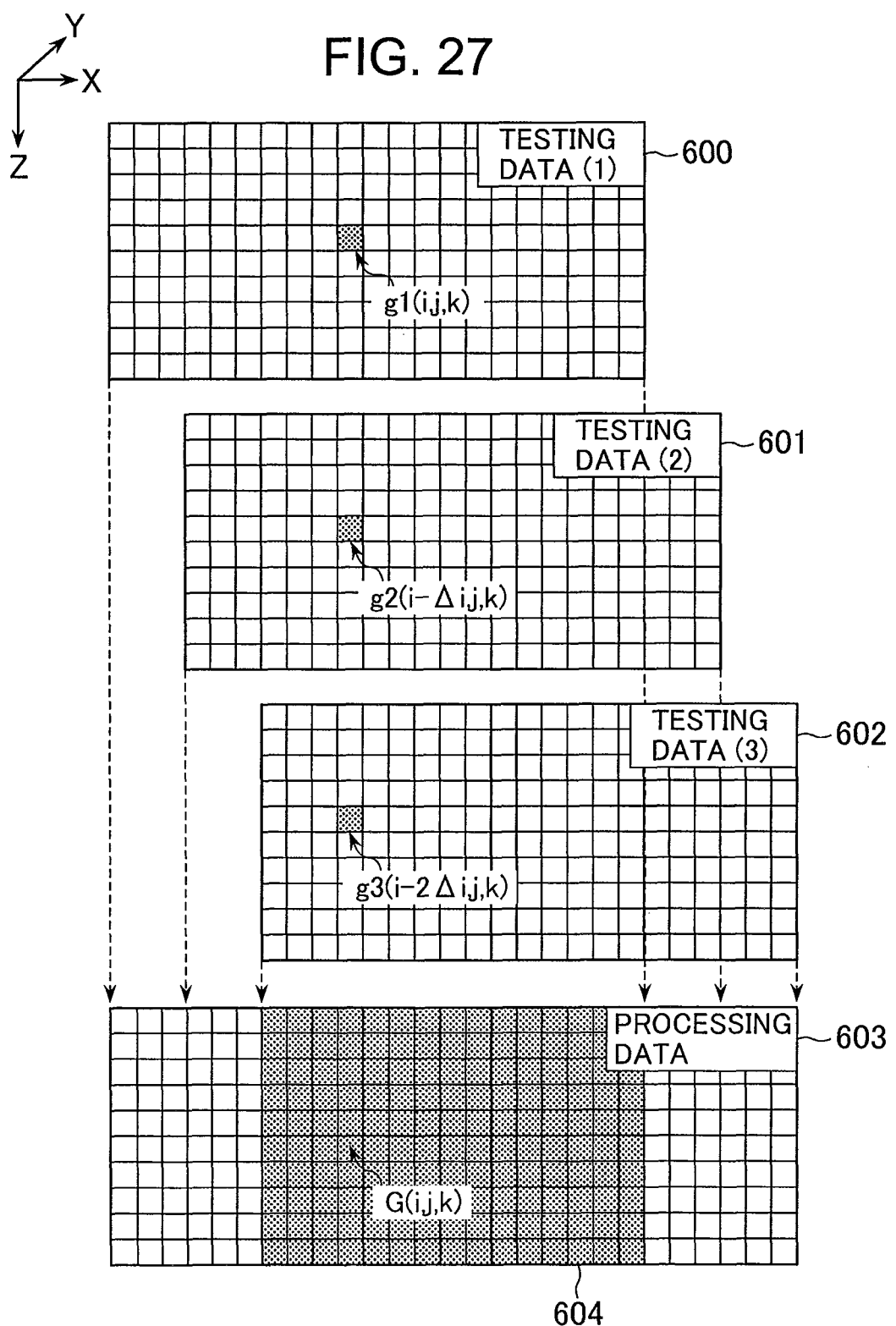
FIG. 27 illustrates processing of three-dimensional testing data in the three-dimensional ultrasonic imaging apparatus according to the fourth embodiment of the present invention of operation.
Figure 28:
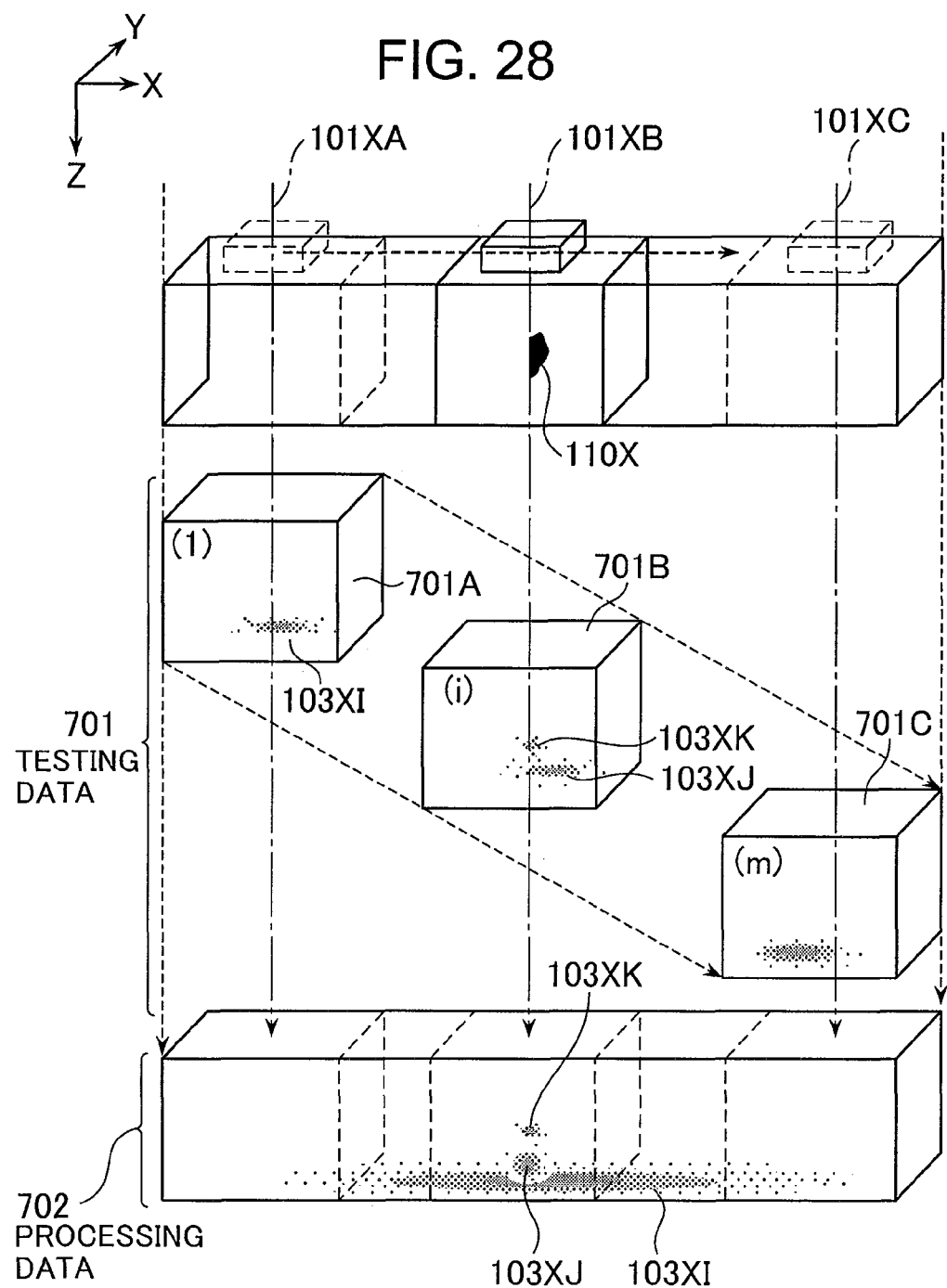
FIG. 28 illustrates processing of three-dimensional testing data in the three-dimensional ultrasonic imaging apparatus according to the fourth embodiment of the present invention of operation.

FIGS. 27 and 28 illustrate processing of three-dimensional testing data in the three-dimensional ultrasonic imaging apparatus according to the fourth embodiment of the present invention.

Three-dimensional testing data shown in FIG. 27 is processed by the computer 102A. FIG. 27 schematically illustrates detailed processing of the three-dimensional testing data in the computer 102XA.

For convenience, FIG. 27 illustrates only testing data on a desired y-axis cross section in the xyz coordinate system. The computer 102XA shown in FIG. 22 performs the steps of: combining waveforms obtained by the piezoelectric elements 104X in relation to a delay time; performing appropriate interpolation processing of waveforms for each beam angle of each ultrasonic wave to convert the waveforms to three-dimensional testing data having voxel format (a voxel means a three-dimensionally arranged cubic element); and processing the three-dimensional testing data. However, the three-dimensional testing data used here represents RF waveforms.

If the array ultrasonic sensor 101X is horizontally displaced by a displacement X from a position of three-dimensional testing data 600 obtained at the testing start position 101XA, a positional shift occurs if the storage range of the three-dimensional testing data remains same. Measurement values by the displacement detector 106X are used to correct the positional shift. The three-dimensional testing data is subjected to a deviation Δ in the X-axis direction, and therefore summation is performed after shifting by the deviation Δ, as shown by formula (5), where X denotes the displacement of the sensor. G denotes a voxel address value of three-dimensional processing data 603 and gm denotes a voxel address value of the m-th three-dimensional testing data. The following formula (5) shows the voxel address value at the time of summation.

[Formula 5]

$$G(i, j, k) = \sum_{m=1}^{m} g_m(i - (m-1)\Delta, j, k) \quad (5)$$

When $i < (m-1)\Delta$, $g_n(i, j, k) = 0$.

In order to schematically illustrate detailed processing, the example of FIG. 27 sums up three different sets of three-dimensional testing data 600, 601, and 602 to obtain the three-dimensional processing data 603.

FIG. 28 illustrates processing described in FIG. 27 together with actual testing conditions.

First three-dimensional testing data (1) 701A denotes three-dimensional testing data obtained at the testing start position 101XA. Similarly, i-th three-dimensional testing data (i) 701B and m-th three-dimensional testing data (m) 701C are obtained at testing positions 101XB and 101XC, respectively. A total of m sets of three-dimensional testing data 701 is obtained.

With the present embodiment, the two-dimensional array ultrasonic sensor 101X is disposed in parallel with the bottom surface, that is, an axial direction of a parallel flat plate or pipe. With these pieces of three-dimensional testing data, a reflected echo 103XI from the bottom surface is obtained directly under the set position of the two-dimensional array ultrasonic sensor. If a defect originates from the bottom side, a defect corner echo 103XK and a defect tip echo 103XJ are observed.

When summation (or averaging) of these pieces of three-dimensional testing data is performed while making a shift by the number of voxels corresponding to the displacement of the array ultrasonic sensor, as shown in FIG. 27, three-dimensional processing data 702 is obtained. At the defect tip echo 103XK and the defect corner echo 103XJ, only the signal of the defect 110X selectively remains by the superposition of wave fronts of ultrasonic waves transmitted from various angles. This process is based on the same principle as the synthetic aperture method. The three-dimensional processing data 702 is displayed on the display unit 103X, and used to check a defect position and evaluate a defect depth.

Three-dimensional ultrasonic imaging in the three-dimensional ultrasonic imaging apparatus according to the present embodiment will be described below with reference to FIGS. 29 and 30.

Figure 29:
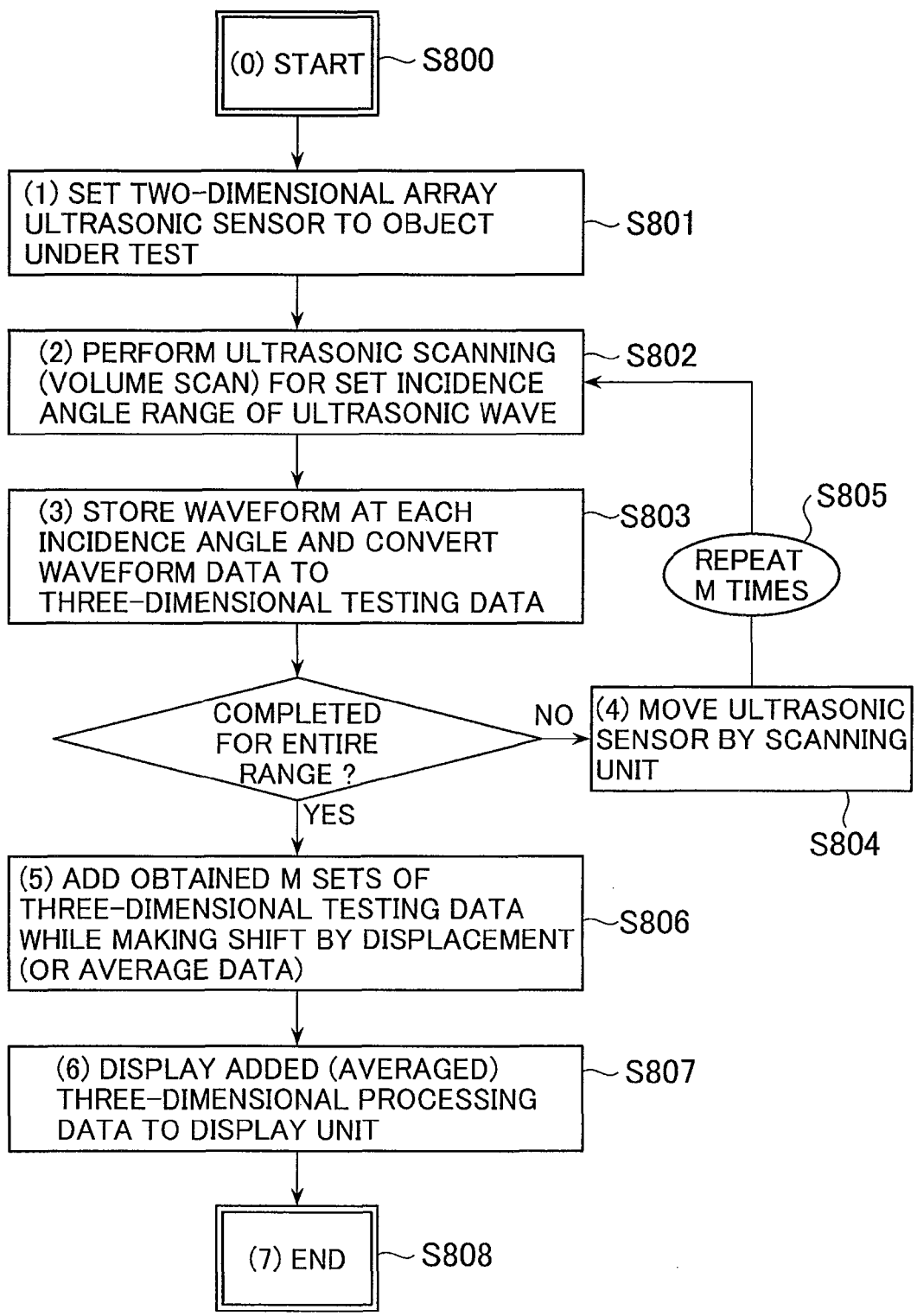
FIG. 29 is a flow chart illustrating detailed processing of three-dimensional ultrasonic imaging in the three-dimensional ultrasonic imaging apparatus according to the fourth embodiment of the present invention.
Figure 30:
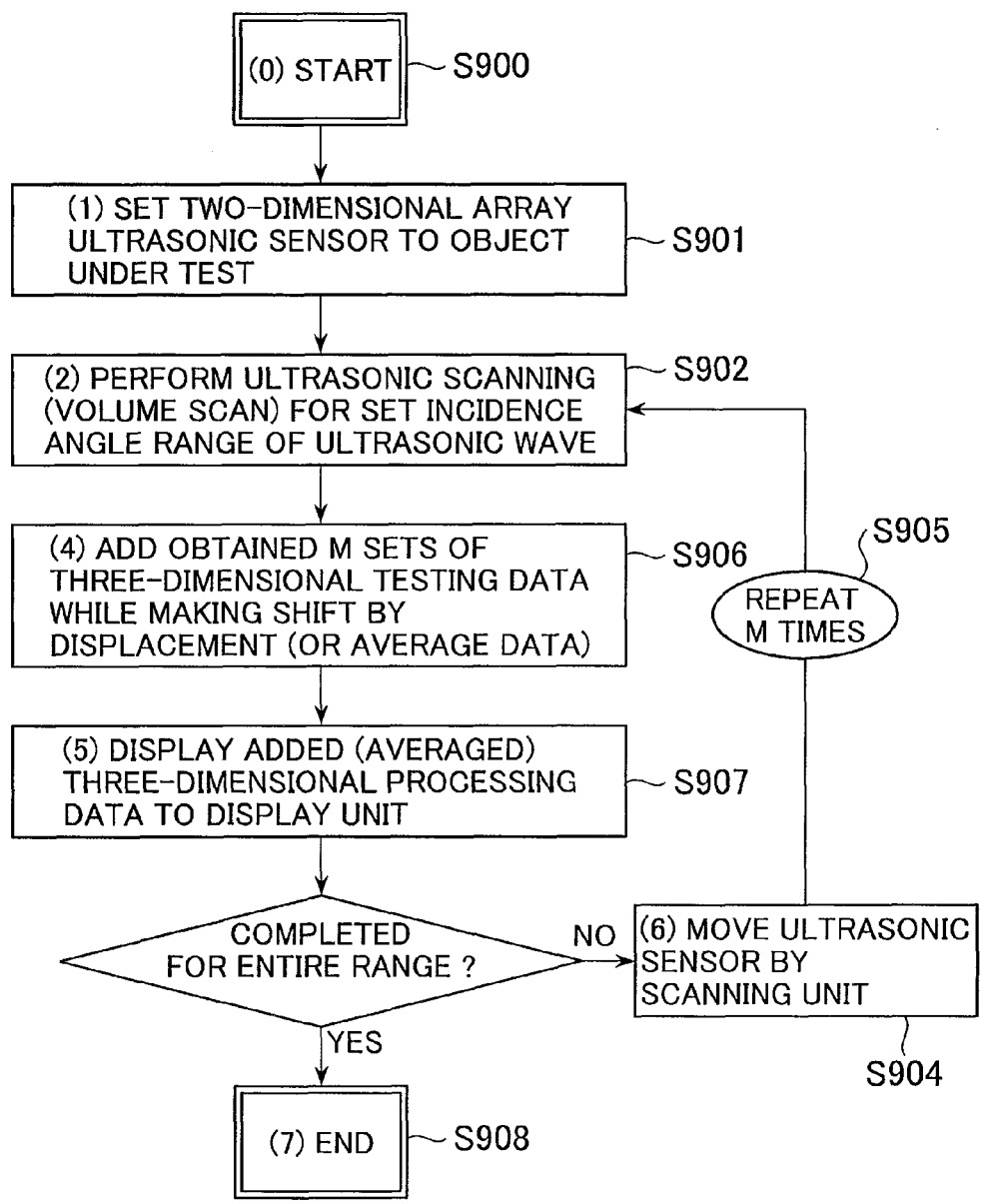
FIG. 30 is a flow chart illustrating detailed processing of three-dimensional ultrasonic imaging in the three-dimensional ultrasonic imaging apparatus according to the fourth embodiment of the present invention.

FIGS. 29 and 30 are flow charts illustrating detailed processing of three-dimensional ultrasonic imaging in the three-dimensional ultrasonic imaging apparatus according to the fourth embodiment of the present invention.

Referring to FIG. 29, the testing process performs the steps of: setting a testing range, and a focal depth and an ultrasonic beam angle range of the two-dimensional array ultrasonic sensor in the transmitter/receiver 102X, and starting testing (step S800); setting the ultrasonic sensor 101X on an object under test (step S801); performing three-dimensional ultrasonic scanning (volume scan) swinging the ultrasonic beam angle (step S802); storing a waveform obtained at each ultrasonic beam angle in the transmitter/receiver 102X, and converting the obtained waveforms to three-dimensional testing data in the computer 102XA (step S803); and displaying the data on the display unit 103X as three-dimensional testing data. If testing is not completed for the entire testing range, the testing process moves the two-dimensional array ultrasonic sensor by the scanning unit 107X (step S804), and repeats m times three-dimensional ultrasonic scanning and conversion to three-dimensional testing data until testing is completed for the entire testing range (step S805).

When testing is completed for the entire testing range (from the testing start position 101XA to the testing end position 101XC), the testing process performs the steps of: summing up (or averaging) the stored three-dimensional testing data while making a shift by the displacement of the ultrasonic sensor 101X in the computer 102XA (step S806); displaying on the display unit 103X the thus obtained (summed up or averaged) three-dimensional processing data (processing data 702) (step S807); and terminating testing (step S808).

FIG. 30 illustrates a second processing flow of three-dimensional ultrasonic imaging. The second processing flow subsequently sums up (or averages) three-dimensional testing data and displays the data each time three-dimensional testing data is stored.

The testing process performs the steps of: setting a testing range, and a focal depth and an ultrasonic beam angle range of the two-dimensional array ultrasonic sensor in the transmitter/receiver 102X, and starting testing (step S900); setting the ultrasonic sensor 101X on an object under test (step S901); performing three-dimensional ultrasonic scanning (volume scan) swinging the ultrasonic beam angle (step S902); and storing a waveform obtained at each ultrasonic beam angle, and converting the obtained waveforms to three-dimensional testing data in the computer 102XA (step S903).

When there are two or more sets of three-dimensional testing data, the testing process sums up (or averages) the stored three-dimensional testing data while making a shift by the displacement of the ultrasonic sensor 101X in the computer 102XA (step S906), and then displays data on the display unit 103X. If testing is not completed for the entire testing range, the testing process moves the array ultrasonic sensor by the scanning unit 107X (step S904), and repeats m times three-dimensional ultrasonic scanning (volume scan) and conversion to three-dimensional testing data until testing is completed for the entire testing range (step S905).

When testing is completed for the entire testing range (from the testing start position 101XA to the testing end position 101XC), the testing process terminates testing (step S908).

As mentioned above, three-dimensional ultrasonic imaging according to the present embodiment comprises the steps of: three-dimensionally scanning the inside of an object under test while varying the beam angle of the ultrasonic wave transmitted from the two-dimensional array ultrasonic sensor; sequentially moving the set position of the two-dimensional array ultrasonic sensor or changing the transmission/reception position of ultrasonic waves; and summing up (or averaging) three-dimensional testing data obtained at each testing position while making a shift by the displacement of the two-dimensional array ultrasonic sensor or by the transmission/reception position to attain three-dimensional imaging. Since three-dimensional processing data can be configured by superimposing ultrasonic waves transmitted from various angles, the effect of ultrasonic focus can be obtained without preparing a number of data processing tables (focal law, delay time). The present embodiment allows high-resolution three-dimensional processing data to be obtained at almost all positions, thus attaining high-accuracy non-destructive testing.

Further, the present embodiment restricts ultrasonic diffusing attenuation which has been a problem of the synthetic aperture method. Specifically, when an object under test is scanned by converging ultrasonic waves from the array ultrasonic sensor, ultrasonic diffusing attenuation can be restricted even with a thick object under test or a long ultrasonic propagation distance. Accordingly, the S/N ratio of three-dimensional testing data can be improved. Similarly, the process of summation (or averaging) of three-dimensional testing data can reduce electrical noise and other random noise. This process also improves the S/N ratio of three-dimensional testing data. The present embodiment enables collective three-dimensional imaging over a wide testing range based on high resolution and high S/N ratio three-dimensional testing data and allows images to be handled as one piece of three-dimensional testing data by using a two-dimensional array ultrasonic sensor. The present embodiment only utilizes one set of data processing table (focal law) and is also applicable to thick objects and high-attenuation materials.

Configuration and operation of a three-dimensional ultrasonic imaging apparatus according to a fifth embodiment of the present invention will be described below with reference to FIGS. 31 and 32. The three-dimensional ultrasonic imaging apparatus according to the present embodiment is the same as that shown in FIG. 22.

Figure 31:
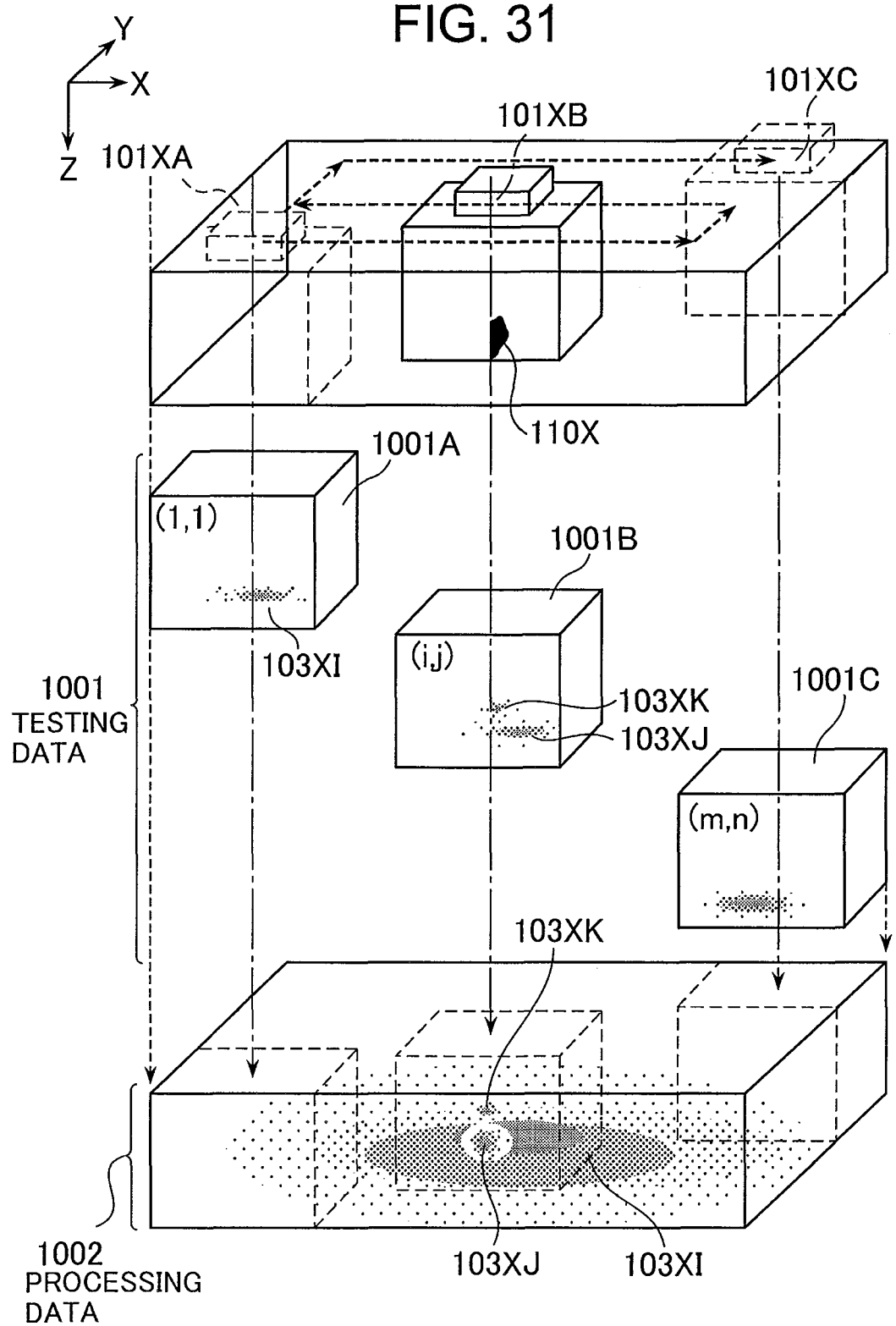
FIG. 31 illustrates processing of three-dimensional testing data in a three-dimensional ultrasonic imaging apparatus according to a fifth embodiment of the present invention of operation.
Figure 32:
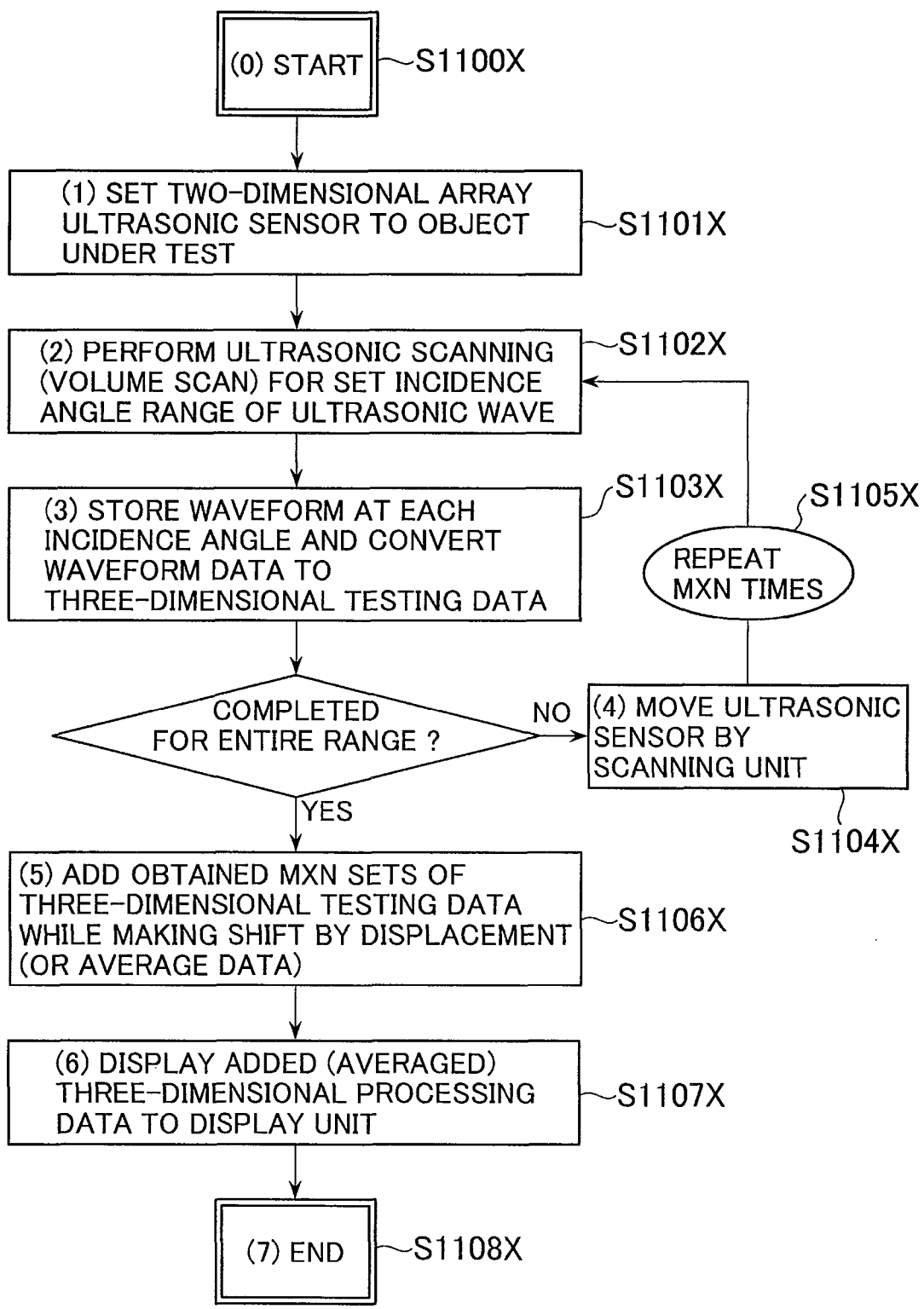
FIG. 32 is a flow chart illustrating detailed processing of three-dimensional ultrasonic imaging in the three-dimensional ultrasonic imaging apparatus according to the fifth embodiment of the present invention.

FIG. 31 illustrates processing of three-dimensional testing data in the three-dimensional ultrasonic imaging apparatus according to the fifth embodiment of the present invention. FIG. 32 is a flow chart illustrating detailed processing of three-dimensional ultrasonic imaging in the three-dimensional ultrasonic imaging apparatus according to the fifth embodiment of the present invention.

The present embodiment shown in FIG. 31 differs from the fourth embodiment of FIG. 28 in that the present embodiment feeds the two-dimensional array ultrasonic sensor also in the y-axis direction, i.e., in a posterior direction of the paper, and therefore is used for a wider testing range. Two-dimensional scanning methods employing a mechanical scanning unit include zigzag scanning and comb scanning. With comb scanning, the array is fed in one axial direction, returned to home position, moved in another axial direction by a scanning pitch, and fed again in the one axial direction.

First three-dimensional testing data (1,1) 1001A denotes three-dimensional testing data obtained at the testing start position 101XA. Similarly, i×j-th three-dimensional testing data (i,j) 1001B and m×n-th three-dimensional testing data (m×n) 1001C are obtained at testing positions 101XB and 101XC, respectively. A total of m×n sets of three-dimensional testing data 1001 is obtained.

With these pieces of three-dimensional testing data, a reflected echo 103XI from the bottom surface is obtained directly under the set position of the two-dimensional array ultrasonic sensor. If a defect originates from the bottom side, a defect corner echo 103XK and a defect tip echo 103XJ are observed.

When summation (or averaging) of these pieces of three-dimensional testing data is performed while making a shift by the number of voxels corresponding to the displacement and direction of the array ultrasonic sensor, three-dimensional processing data 1002 is obtained. At the defect tip echo 103XK and the defect corner echo 103XJ, only the signal of the defect 110X selectively remains by the superposition of wave fronts of ultrasonic waves three-dimensionally transmitted from various angles. This process is based on the same principle as the synthetic aperture method. The three-dimensional processing data 1002 is displayed on the display unit 103X, and used to check a defect position and evaluate a defect depth.

Detailed processing of three-dimensional ultrasonic imaging will be described below with reference to FIG. 32.

The testing process performs the steps of: setting a testing range, and a focal depth and an ultrasonic beam angle range of the two-dimensional array ultrasonic sensor in the transmitter/receiver 102X, and starting testing (step S1100X); setting the ultrasonic sensor 101X on an object under test (step S1101X); performing three-dimensional ultrasonic scanning (volume scan) swinging the ultrasonic beam angle (step S1102X); storing a waveform obtained at each ultrasonic beam angle in the transmitter/receiver 102X, and converting the obtained waveforms to three-dimensional testing data in the computer 102XA (step S1103X); and displaying the data on the display unit 103X as three-dimensional testing data.

If testing is not completed for the entire testing range, the testing process moves the array ultrasonic sensor by the scanning unit 107X (step S1104X), and repeats m×n times three-dimensional ultrasonic scanning and conversion to three-dimensional testing data until testing is completed for the entire testing range (step S1105X).

When testing is completed for the entire testing range (from the testing start position 101XA to the testing end position 101XC), the testing process sums up (or averages) the stored three-dimensional testing data while making a shift by the displacement of the ultrasonic sensor 101X in the computer 102XA (step S1106X).

The testing process displays on the display unit 103X the thus obtained (summed up or averaged) three-dimensional processing data (processing data 1002) (step S1107X), and terminates testing (step S1108X).

As mentioned above, three-dimensional ultrasonic imaging according to the present embodiment also comprises the steps of: three-dimensionally scanning the inside of an object under test while varying the beam angle of the ultrasonic wave transmitted from the two-dimensional array ultrasonic sensor; sequentially moving the set position of the two-dimensional array ultrasonic sensor or changing the transmission/reception position of ultrasonic waves; and summing up (or averaging) three-dimensional testing data obtained at each testing position while making a shift by the displacement of the two-dimensional array ultrasonic sensor or by the transmission/reception position to attain three-dimensional imaging. Since three-dimensional processing data can be configured by superimposing ultrasonic waves transmitted from various angles, the effect of ultrasonic focus can be obtained without preparing a number of data processing tables (focal law, delay time). The present embodiment allows high-resolution three-dimensional processing data to be obtained at almost all positions, thus attaining high-accuracy non-destructive testing.

Further, the present embodiment restricts ultrasonic diffusing attenuation which has been a problem of the synthetic aperture method. Specifically, when an object under test is scanned by converging ultrasonic waves from the array ultrasonic sensor, ultrasonic diffusing attenuation can be restricted even with a thick object under test or a long ultrasonic propagation distance. Accordingly, the S/N ratio of three-dimensional testing data can be improved. Similarly, the process of summation (or averaging) of three-dimensional testing data can reduce electrical noise and other random noise. This process also improves the S/N ratio of three-dimensional testing data. The present embodiment enables collective three-dimensional imaging over a wide testing range based on high resolution and high S/N ratio three-dimensional testing data and allows images to be handled as one piece of three-dimensional testing data by using a two-dimensional array ultrasonic sensor. The present embodiment only utilizes one set of data processing table (focal law) and is also applicable to thick objects and high-attenuation materials.

Configuration and operation of a three-dimensional ultrasonic imaging apparatus according to a sixth embodiment of the present invention will be described below with reference to FIGS. 33 and 34. The three-dimensional ultrasonic imaging apparatus according to the present embodiment is the same as that shown in FIG. 22.

Figure 33:
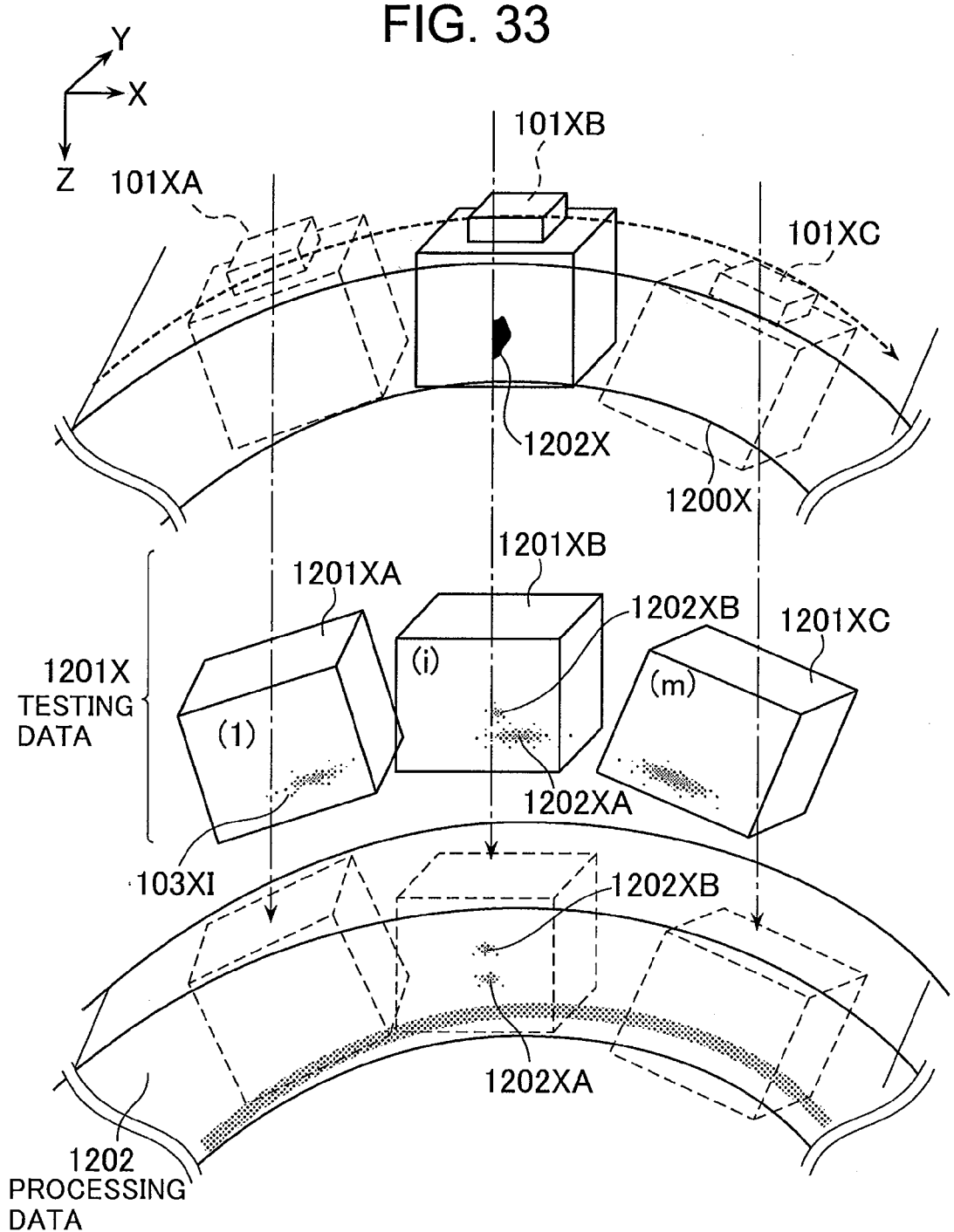
FIG. 33 illustrates processing of three-dimensional testing data in a three-dimensional ultrasonic imaging apparatus according to a sixth embodiment of the present invention of operation.
Figure 34:
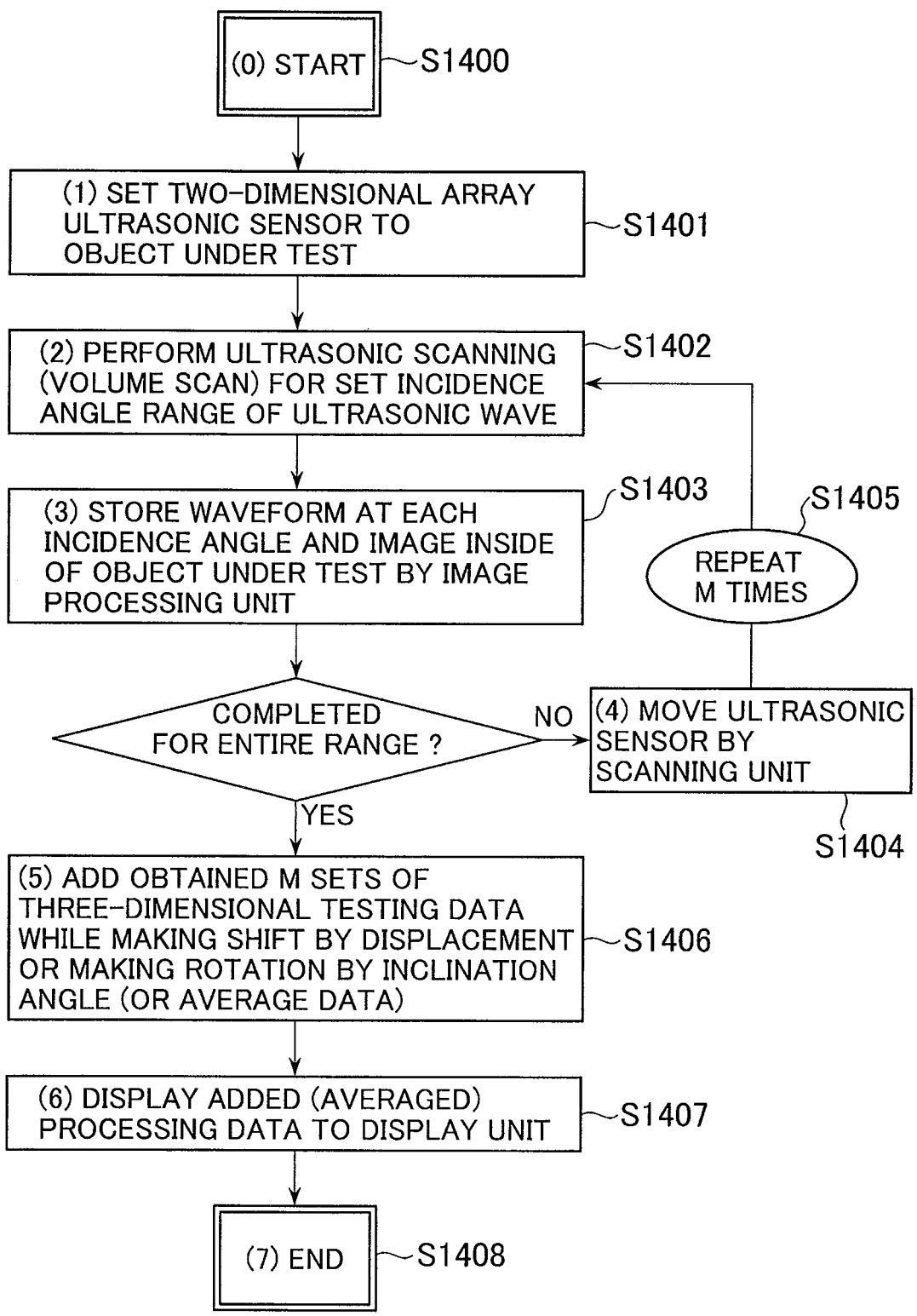
FIG. 34 is a flow chart illustrating detailed processing of three-dimensional ultrasonic imaging in the three-dimensional ultrasonic imaging apparatus according to the sixth embodiment of the present invention.

FIG. 33 illustrates processing of three-dimensional testing data in the three-dimensional ultrasonic imaging apparatus according to the sixth embodiment of the present invention. FIG. 34 is a flow chart illustrating detailed processing of three-dimensional ultrasonic imaging in the three-dimensional ultrasonic imaging apparatus according to the sixth embodiment of the present invention.

The present embodiment shown in FIG. 33 applies an object under test having a curved surface like a circumference of a pipe or having a complicated shape while the fourth embodiment of FIG. 28 and the fifth embodiment of FIG. 31 apply an object under test having a planar shape.

Referring to FIG. 33, with an object under test 1200X having a curved shape, first three-dimensional testing data (1) 1201XA denotes three-dimensional testing data measured at the testing start position 101XA. Similarly, i-th three-dimensional testing data (i) 1201XB and m-th three-dimensional testing data (m) 1201XC are measured at testing positions 101XB and 101XC, respectively. When three-dimensional ultrasonic scanning (volume scan) is performed at each position, a total of m sets of three-dimensional testing data 1201X is obtained. The present embodiment assumes an object under test having a curved shape such as a pipe. Therefore, since the surface on which the array ultrasonic sensor 101X is disposed is almost in parallel with the bottom surface, an echo 103XI from the bottom surface is obtained directly under the set position of the array ultrasonic sensor 101X. If a defect originates from the bottom side, a defect corner echo 1202XA and a defect tip echo 1202XB are observed corresponding to respective defect position 1202X.

The testing process sums up (or averages) these pieces of three-dimensional testing data while making a shift by the number of pixels corresponding to the displacement of the two-dimensional array ultrasonic sensor. The present embodiment differs from the first and second embodiments in that the object under test has a curved surface and therefore that the effect of inclination by this shape needs to be corrected when processing three-dimensional testing data. The present embodiment, therefore, is provided with premeasured data regarding the surface shape of the object under test or with a function to measure the inclination of the two-dimensional array ultrasonic sensor in the displacement detection unit to correct the inclination at the time of summation (or averaging) of three-dimensional testing data. Specifically, the computer shifts three-dimensional testing data by the displacement of the center position of the array ultrasonic sensor from the testing start position, rotates the data by the rotation angle from the testing start position, and performs summation (or averaging) to obtain three-dimensional testing data 1203X.

The computer corrects the inclination of each voxel to adjust mutual positions of voxels through appropriate supplementary processing as preprocessing, and then performs summation (or averaging). With the three-dimensional testing data 1203X, at a defect corner echo 1202XA and a defect tip echo 1202XB, only the signal at a real defect position selectively remains by the superposition of wave fronts of ultrasonic waves three-dimensionally transmitted from various angles. The three-dimensional testing data 1203X is used to check a defect position and evaluate a defect depth. Even for a complicated surface shape, three-dimensional processing data can be created by performing the above-mentioned processing.

Detailed processing of three-dimensional ultrasonic imaging will be described below with reference to FIG. 34.

The testing process performs the steps of: setting a testing range, and a focal depth and an ultrasonic beam angle range of the two-dimensional array ultrasonic sensor, and starting testing (step S1400); setting the two-dimensional ultrasonic sensor to an object under test (S1401); performing three-dimensional ultrasonic scanning (volume scan) (S1402); storing a waveform obtained at each ultrasonic beam angle; and converting the obtained waveforms to three-dimensional testing data in the computer (step S1403).

If testing is not completed for the entire testing range, the testing process moves the two-dimensional array ultrasonic sensor along the surface of the object under test by the scanning unit (step S1404), and repeats m times three-dimensional ultrasonic scanning and conversion to three-dimensional testing data until testing is completed for the entire testing range (step S1405).

When testing is completed for entire testing range, the testing process performs the steps of: shifting each piece of three-dimensional testing data stored in the computer by the displacement of the two-dimensional array ultrasonic sensor from the testing start position, then rotating the data by the inclination angle from the testing start position, and then performing summation (or averaging) (step S1406); displaying the result on the display unit (step S1407); and terminating testing (step S1408).

As mentioned above, three-dimensional ultrasonic imaging according to the present embodiment also comprises the steps of: three-dimensionally scanning the inside of an object under test while varying the beam angle of the ultrasonic wave transmitted from the two-dimensional array ultrasonic sensor; sequentially moving the set position of the two-dimensional array ultrasonic sensor or changing the transmission/reception position of ultrasonic waves; and summing up (or averaging) three-dimensional testing data obtained at each testing position while making a shift by the displacement of the two-dimensional array ultrasonic sensor or by the transmission/reception position to attain three-dimensional imaging. Since three-dimensional processing data can be configured by superimposing ultrasonic waves transmitted from various angles, the effect of ultrasonic focus can be obtained without preparing a number of data processing tables (focal law, delay time). The present embodiment allows high-resolution three-dimensional processing data to be obtained at almost all positions, thus attaining high-accuracy non-destructive testing.

Further, the present embodiment restricts ultrasonic diffusing attenuation which has been a problem of the synthetic aperture method. Specifically, when an object under test is scanned by converging ultrasonic waves from the array ultrasonic sensor, ultrasonic diffusing attenuation can be restricted even with a thick object under test or a long ultrasonic propagation distance. Accordingly, the S/N ratio of three-dimensional testing data can be improved. Similarly, the process of summation (or averaging) of three-dimensional testing data can reduce electrical noise and other random noise. This process also improves the S/N ratio of three-dimensional testing data. The present embodiment enables collective three-dimensional imaging over a wide testing range based on high resolution and high S/N ratio three-dimensional testing data and allows images to be handled as one piece of three-dimensional testing data by using a two-dimensional array ultrasonic sensor. The present embodiment only utilizes one set of data processing table (focal law) and is also applicable to thick objects and high-attenuation materials.

Configuration and operation of a three-dimensional ultrasonic testing apparatus according to a seventh embodiment of the present invention will be described below with reference to FIGS. 35 to 46.

First of all, the configuration of the three-dimensional ultrasonic testing apparatus according to the present embodiment will be described below with reference to FIG. 35.

Figure 35:
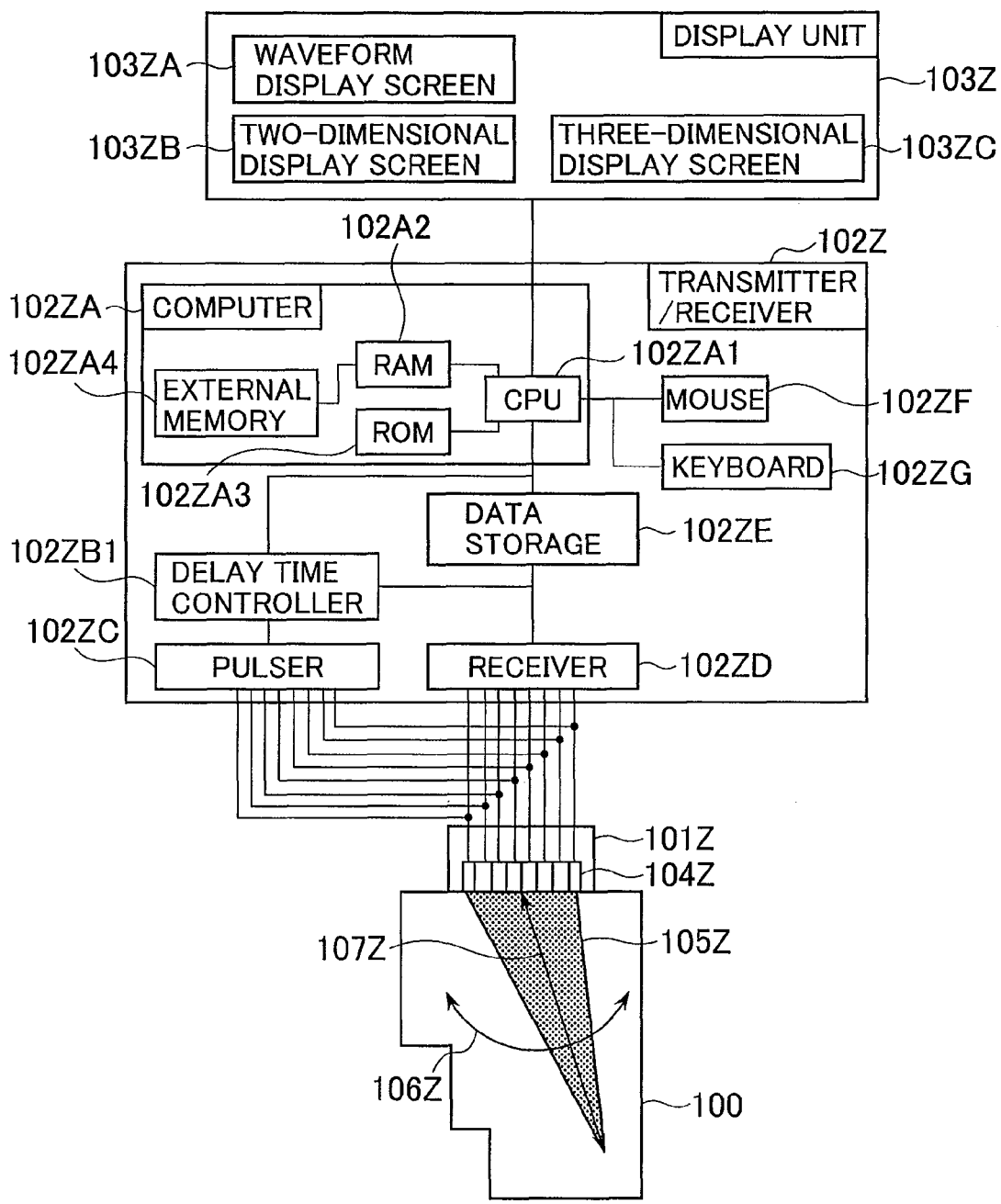
FIG. 35 is a block diagram illustrating a configuration of a three-dimensional ultrasonic testing apparatus according to a seventh embodiment of the present invention.

FIG. 35 is a block diagram illustrating a configuration of the three-dimensional ultrasonic testing apparatus according to the seventh embodiment of the present invention.

The three-dimensional ultrasonic testing apparatus according to the present embodiment is composed of an array ultrasonic sensor 101Z configured to transmit an ultrasonic wave to an object under test 100, a transmitter/receiver 102Z, and a display unit 103Z configured to display receive signals and testing images.

The array ultrasonic sensor 101Z is basically composed of a plurality of piezoelectric elements 104Z, each being able to transmit and receive an ultrasonic wave as shown in FIG. 35. The array ultrasonic sensor 101Z is disposed on a testing surface of the object under test 100. The array ultrasonic sensor 101Z transmits an ultrasonic beam 105Z with a drive signal supplied from the transmitter/receiver 102Z, propagates the ultrasonic beam 105Z in the object under test 100, detects a reflected wave generated by the object under test 100, and feeds a receive signal to the transmitter/receiver 102Z as needed.

The transmitter/receiver 102Z includes a computer 102ZA, a delay time controller 102ZB1, a pulser 102ZC, a receiver 102ZD, and data storage 102ZE to transmit and receive an ultrasonic wave by using the array ultrasonic sensor 101Z. In the transmitter/receiver 102Z, the pulser 102ZC supplies a drive signal to the array ultrasonic sensor 101Z, and the receiver 102ZD processes a receive signal received from the array ultrasonic sensor 101Z.

The computer 102ZA basically includes a central processing unit (CPU) 102ZA1, a random access memory (RAM) 102ZA2, a read-only memory (ROM) 102ZA3, and an external memory 102ZA4. The ROM 102ZA3 contains a program for controlling the CPU 102ZA1 written thereto. The CPU 102ZA1, according to the program, performs operations while reading necessary external data from the data storage 102ZE and exchanging data with the RAM 102ZA2 and the external memory 102ZA4, and outputs processed data to the data storage 102ZE.

The CPU 102ZA1 controls the delay time controller 102ZB, the pulser 102ZC, and the receiver 102ZD to perform necessary operations. The delay time controller 102ZB controls both the timing of drive signal output from the pulser 102ZC and the timing of receive signal input to the receiver 102ZD to attain operations of the array ultrasonic sensor 101Z employing the phased array method.

The array ultrasonic sensor 101Z employing the phased array method controls a focal depth 107Z and a beam angle 106Z of the ultrasonic beam 105Z which are formed by combining ultrasonic waves transmitted from each piezoelectric element of the array ultrasonic sensor 101Z in relation to a delay time, and receives a reflected ultrasonic wave. The receiver 102ZD supplies a receive signal to the data storage 102ZE. The data storage 102ZE processes the supplied receive signal, stores it as storage data, and at the same time feeds it to the computer 102ZA. The computer 102ZA performs the steps of: combining waveforms obtained by the piezoelectric elements in relation to a delay time; performing appropriate interpolation processing of waveforms for each beam angle of each ultrasonic wave to create two-dimensional testing data in units of a two-dimensional square lattice as represented by the pixel format as well as three-dimensional testing data in units of a three-dimensional cubic lattice as represented by the voxel format; imaging these pieces of data; and displaying them on the display unit 103Z.

The display unit 103Z includes a two-dimensional display screen 103ZB for displaying two-dimensional testing data, a three-dimensional display screen 103ZC for displaying three-dimensional testing data, and a waveform display screen 103ZA for displaying a waveform signal of each piezoelectric element. FIG. 35 illustrates one display unit 103Z. However, the waveform display screen 103ZA, the two-dimensional display screen 103ZB, and the three-dimensional display screen 103ZC may be displayed separately by a plurality of display units.

Exemplary display of the three-dimensional display screen 103C in the three-dimensional ultrasonic testing apparatus according to the present embodiment will be described below with reference to FIG. 36.

Figure 36:
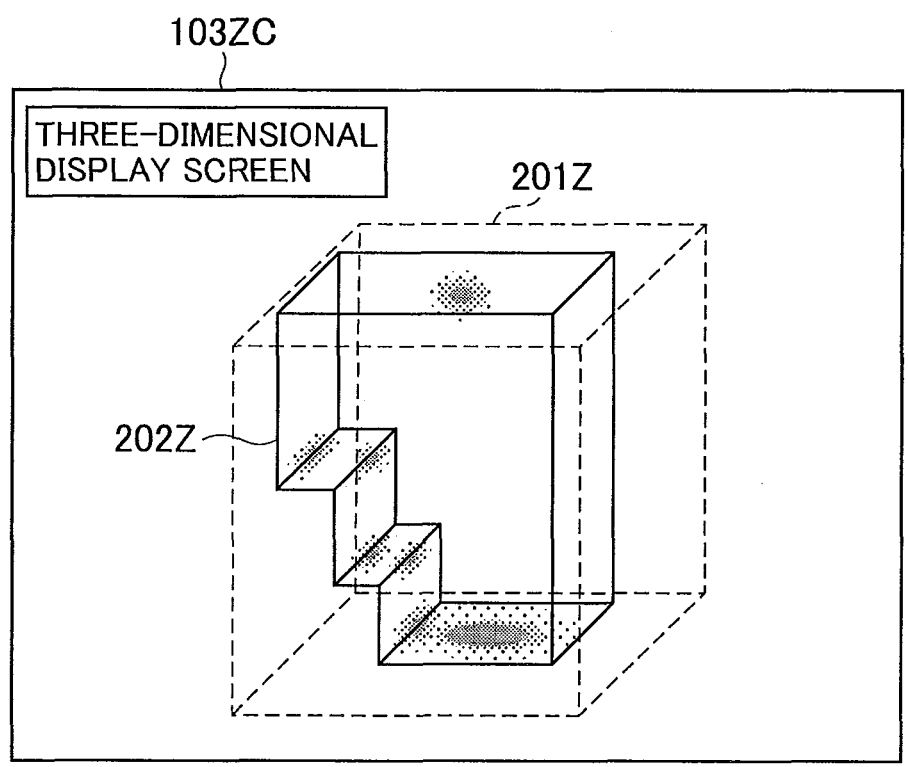
FIG. 36 illustrates an exemplary three-dimensional display screen in the three-dimensional ultrasonic testing apparatus according to the seventh embodiment of the present invention.

FIG. 36 illustrates exemplary display of the three-dimensional display screen in the three-dimensional ultrasonic testing apparatus according to the seventh embodiment of the present invention.

The three-dimensional display screen 103CZ on the display unit 103Z displays three-dimensional testing data 201Z, as shown in FIG. 36. The three-dimensional display screen 103CZ can display the data in a desired display size from a desired viewpoint by an input from a mouse 102ZF or a keyboard 102ZG connected to the computer 102ZA. In this case, an inspector can numerically input a scale of enlargement for changing the display size from the keyboard 102ZG. Although the display color and transparency are given in units of a voxel lattice, they can be changed in relation to reflection intensity input from the mouse 102ZF and the keyboard 102ZG. Since a plurality of display color patterns are provided, an inspector can select one according to his or her application.

These three-dimensional drawing algorithms have been attained, for example, in libraries as represented by OpenGL (a registered trademark) and DirectX (a registered trademark) which are industry-wide standard graphics application programming interfaces (Graphics APIs). If necessary information such as the shape, viewpoint, and display position of an object to be displayed is given by using these Graphics APIs in a program, a three-dimensional shape can be easily drawn with a desired viewpoint, colors, transparency, and size at a desired position on the display unit.

The three-dimensional display screen 103ZC displays three-dimensional shape data 202Z representing the shape of an object under test 100 together with the three-dimensional testing data 201Z thereof. The three-dimensional shape data 202Z is read from the outside of the computer 102ZA. In particular, if CAD data of the object under test 100 exists, this data can be read and displayed. The format of CAD data allows it to be input and output by commercial CAD software. For example, the STL (an abbreviation of Stereo Lithography or Standard Triangulated Language) format is used, which can be read and output by many CAD software products. The STL format is a representation of a surface of an object with a set of a number of triangles. A planar normal vector and coordinate values of three apexes of these triangles are stored in a STL file. Drawing a plurality of straight lines and triangles makes it easier to display three-dimensional shape data 202Z from an STL format file by using Graphics API. Three-dimensional shape data can be displayed only with outlines as shown in FIG. 36, opaquely with outer surfaces filled, or half-transparently. These display modes can be easily attained by changing the transparency value given to drawing functions implemented in Graphics API when drawing triangles. Even if the three-dimensional shape data 202Z overlaps with the three-dimensional testing data 201Z, these display modes make the data legible for an inspector. Further, the three-dimensional shape data 202Z can be shown or hidden as required.

Although not shown, a plurality of pieces of three-dimensional shape data 202Z can be simultaneously displayed on the three-dimensional display screen 103ZC.

A selected three-dimensional shape data 202Z can be displayed from a desired viewpoint, at a desired position, and in a desired size independently from the three-dimensional testing data 201Z by an input from the mouse 102ZF or the keyboard 102ZG connected to the computer 102ZA.

The following describes sizing of a crack present inside an object under test from testing images obtained by the phased array method by using three-dimensional ultrasonic testing according to the present embodiment with reference to FIGS. 37 to 46.

First of all, a three-dimensional scanning method in the three-dimensional ultrasonic testing apparatus according to the present embodiment will be described below with reference to FIGS. 37A to 37D.

FIGS. 37A to 37D illustrate an exemplary three-dimensional scanning method in the three-dimensional ultrasonic testing apparatus according to the seventh embodiment of the present invention.

FIGS. 37A to 37D illustrate sizing of a crack 303Z originating from a portion 303ZD on the bottom surface of a plate 302Z by using the three-dimensional phased array method, one of three-dimensional ultrasonic testing methods.

Figure 37A:
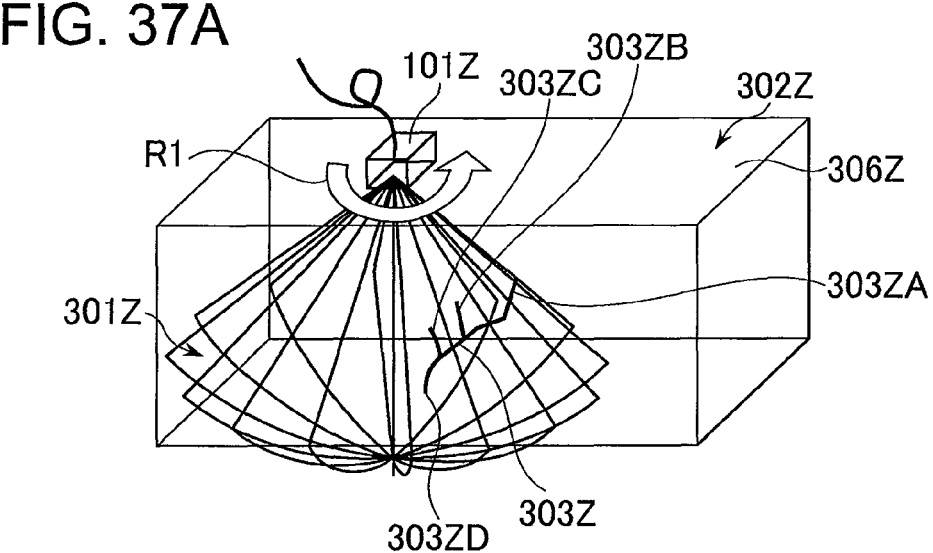
FIGS. 37A to 37D illustrate an exemplary three-dimensional scanning method in the three-dimensional ultrasonic testing apparatus according to the seventh embodiment of the present invention.
Figure 37B:
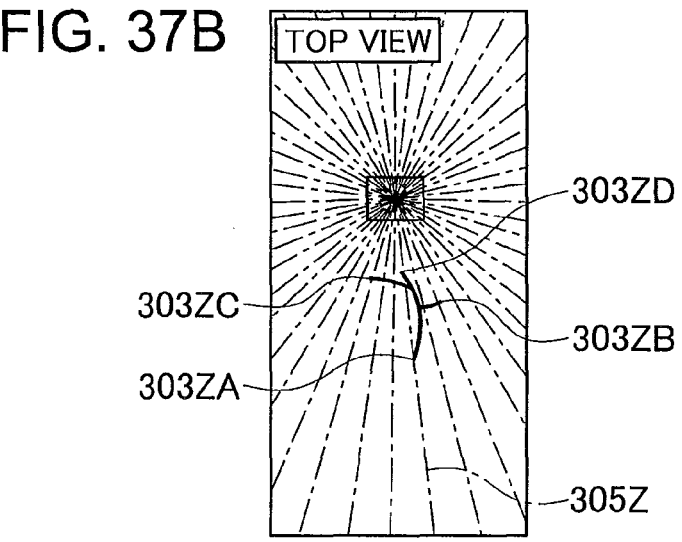
Figure 37D:
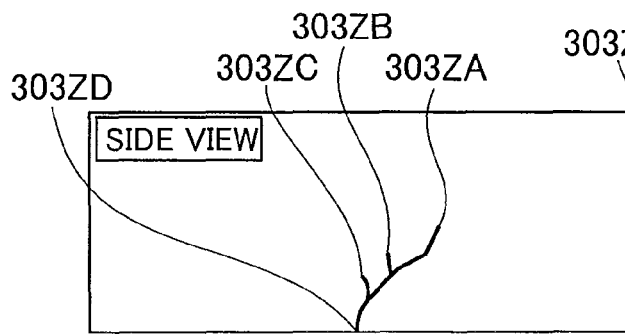
Figure 37C:
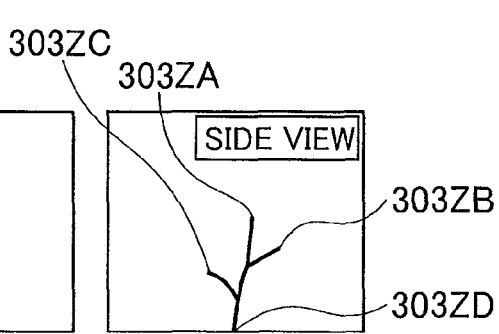

Although metal is mainly assumed as the plate 302Z, this example is applicable to diverse materials such as resin. The crack 303Z branches off and has ends 303ZA, 303ZB, and 303ZC. FIG. 37A is a bird's-eye view of the crack 303Z, FIG. 37B is a top view thereof, and FIGS. 37C and 37D are side views thereof. Although this example assumes that the crack 303Z is like a SCC (stress corrosion crack) which branches off, the crack does not necessarily branch off.

As shown in FIG. 37A, the array ultrasonic sensor 101Z is disposed on a testing surface 306Z preferable to test the crack 303Z through an appropriate couplant (an ultrasonic propagation medium). The array ultrasonic sensor 101Z may be either for transverse wave generation or longitudinal wave generation, and an appropriate wedge is disposed between the array ultrasonic sensor 101Z and the testing surface 306Z. For example, an ultrasonic sensor for longitudinal wave generation is disposed with a wedge to transmit a transverse wave to the plate 302Z.

Although a three-dimensional scanning process can be set in any desired way with a delay time pattern controlled by the delay time controller 102ZB1 (FIG. 35), the following describes a scanning process with which a two-dimensional sectorial plane is rotated by 180 degrees (hereinafter referred to as sectorial rotation scanning process).

The sectorial rotation scanning process rotates a two-dimensional sectorial plane used in the conventional sectorial scanning process around the center axis of the sectorial in appropriate angular steps only by changing the delay time. The sectorial rotation scanning process makes it possible to three-dimensionally scan the inside of an object under test without moving the array ultrasonic sensor 101Z.

FIG. 37A illustrates a state in which a sectorial plane is being rotated in the direction shown by an arrow R1, and a sectorial group 301 is obtained as storage data. FIG. 37B illustrates positions of a plurality of sectorial planes with chain lines when viewed from the top. Although FIG. 37B illustrates 24 sectorial planes in rotational angular steps of 7.5 degrees, FIG. 37A illustrates several out of the 24 sectorial planes in consideration of the legibility. The number of ultrasonic beams 105Z and a focal depth 107Z composing a sectorial, and a rotational angular step of the sectorial are set in consideration of the size of the crack 303Z under assumption and the required spatial resolution.

An exemplary two-dimensional display screen of a testing result obtained by the three-dimensional scanning process in the three-dimensional ultrasonic testing apparatus according to the present embodiment will be described below with reference to FIG. 38.

Figure 38:
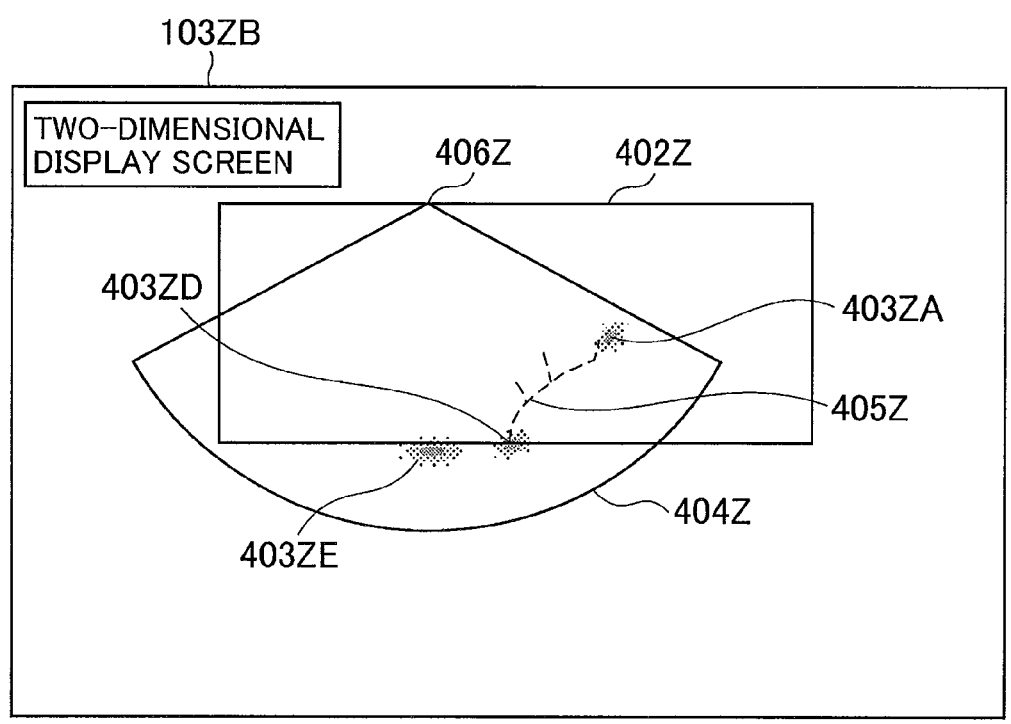
FIG. 38 illustrates an exemplary two-dimensional display screen of a testing result obtained by the three-dimensional scanning method in the three-dimensional ultrasonic testing apparatus according to the seventh embodiment of the present invention.

FIG. 38 illustrates an exemplary two-dimensional display screen of a testing result obtained by the three-dimensional scanning process in the three-dimensional ultrasonic testing apparatus according to the seventh embodiment of the present invention.

Each sectorial plane of the sectorial group 301Z shown in FIG. 37 can be displayed in the two-dimensional display screen 103ZB in any desired way by specifying a sectorial plane. FIG. 38 illustrates an exemplary two-dimensional display screen 103ZB displaying a sectorial plane 404Z at a cross-sectional position 305Z shown in FIG. 37B. Dotted lines 405Z denote lines projected onto the sectorial plane 404Z of the crack 303Z, and are shown to make it easier to understand the present embodiment.

Since the sectorial plane 404Z includes an incidence point 406Z, the originating portion 303ZD of the crack 303Z, and an end portion 303ZA thereof, as shown in FIG. 38, an echo 403ZD caused by the reflection at the originating portion 303ZD and an echo 403ZA caused by the reflection at the end portion 303ZA are shown. Echoes caused by the reflection at other end portions are not shown. A bottom surface echo 403ZE caused by the reflection on the bottom surface of the plate 302Z directly below the incidence point 406Z is shown. Profile lines 402Z shown in FIG. 38 are profile lines of the plate 302Z. These lines are calculated from CAD data of the plate 302Z read from the outside and displayed on the two-dimensional display screen 103ZB together with a testing result.

An exemplary three-dimensional display screen of a testing result obtained by the three-dimensional scanning process in the three-dimensional ultrasonic testing apparatus according to the present embodiment will be described below with reference to FIG. 39.

Figure 39:
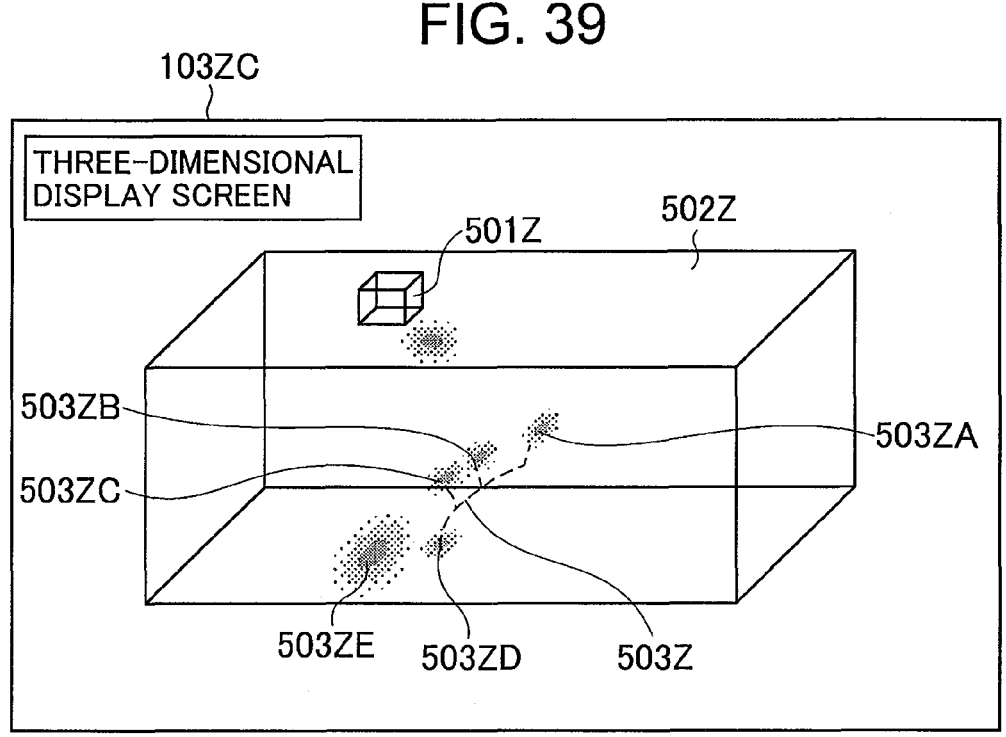
FIG. 39 illustrates an exemplary three-dimensional display screen of a testing result obtained by the three-dimensional scanning method in the three-dimensional ultrasonic testing apparatus according to the seventh embodiment of the present invention.

FIG. 39 illustrates an exemplary three-dimensional display screen of the testing result obtained by the three-dimensional scanning process in the three-dimensional ultrasonic testing apparatus according to the seventh embodiment of the present invention.

FIG. 39 illustrates exemplary three-dimensional testing data, created from the storage data obtained by the sectorial rotation scanning process, displayed on the three-dimensional display screen 103ZC. Dotted lines 505Z denote a three-dimensional shape of the crack 303Z, and are shown to make it easier to understand the present embodiment.

Since the storage data used here is composed of a plurality of sectorial planes including the end portions 303ZA, 303ZB, and 303ZC, and the originating portion 303ZD of the crack 303Z shown in FIG. 37, or a plurality of sectorial planes passing through the vicinity thereof. Therefore, the three-dimensional display screen 103CZ displays echoes 503ZA, 503ZB, 503ZC, and 503ZD caused by ultrasonic waves reflected by the end portions 303ZA, 303ZB, and 303ZC, and the originating portion 303ZD, respectively. Similarly to FIG. 38, the screen 103CZ also displays a bottom surface echo 503ZE. The screen 103CZ further displays the CAD data 501Z of the array ultrasonic sensor 101Z and the CAD data 502Z of the plate 302Z read from the outside together with a testing result.

The two-dimensional phased array method must locate a plurality of echo positions while checking each individual sectorial image as shown in FIG. 38. On the other hand, the three-dimensional phased array method can check a plurality of echoes at one time from the three-dimensional images as shown in FIG. 39, thus allowing testing procedures to be performed efficiently and quickly.

Another three-dimensional scanning process in the three-dimensional ultrasonic testing apparatus according to the present embodiment will be described below with reference to FIG. 40.

Figure 40:
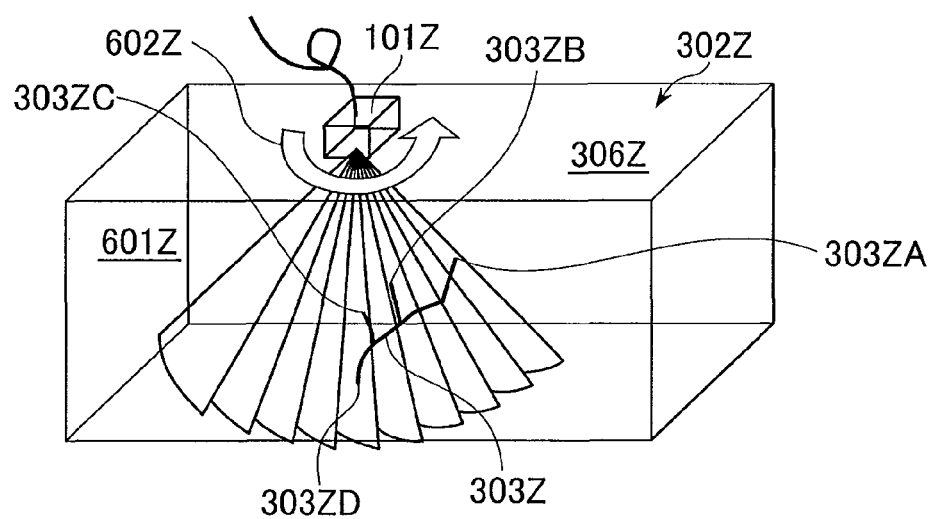
FIG. 40 illustrates another three-dimensional scanning method in the three-dimensional ultrasonic testing apparatus according to the seventh embodiment of the present invention.

FIG. 40 illustrates another three-dimensional scanning process in the three-dimensional ultrasonic testing apparatus according to the seventh embodiment of the present invention.

FIG. 40 illustrates a typical three-dimensional scanning process other than the sectorial rotation scanning process, with which data is gathered by swinging a sectorial plane like a folding fan (hereinafter referred to as sectorial swing scanning). FIG. 40 illustrates a state where the crack 303Z is tested with the sectorial swing scanning process. The array ultrasonic sensor 101Z is disposed in the same way as the above-mentioned sectorial rotation scanning process.

The sectorial swing scanning process rotates a sectorial plane used in the conventional sectorial scanning process in the direction perpendicular thereto centering on the ultrasonic incidence point in appropriate angular steps based on a delay time setup. The sectorial swing scanning process also makes it possible to three-dimensionally scan the inside of an object under test without moving the array ultrasonic sensor 1012.

FIG. 40 illustrates a state where the sectorial plane is swung in the direction shown by an arrow 602Z to obtain a sectorial group 601Z as storage data. The number of ultrasonic beams 105Z and a focal depth 107Z composing a sectorial, and a swing angular step of the sectorial are set in consideration of the size of the crack 303Z under assumption and the required spatial resolution.

A method for sizing a crack by using three-dimensional testing data obtained by the three-dimensional scanning process in the three-dimensional ultrasonic testing apparatus according to the present embodiment will be described below with reference to FIGS. 41 to 46.

Figure 41:
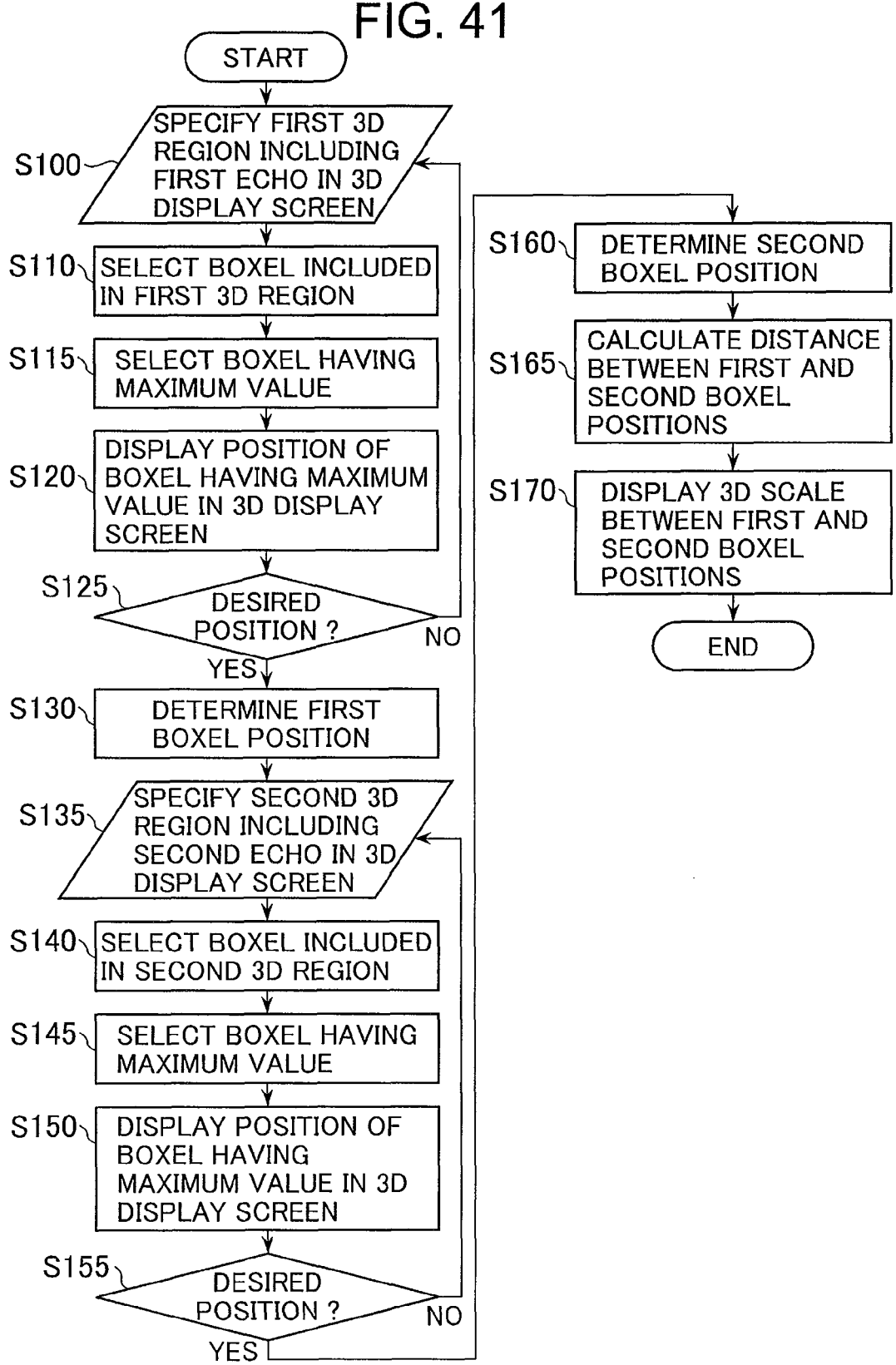
FIG. 41 is a flow chart illustrating detailed processing of a crack sizing method in the three-dimensional ultrasonic testing apparatus according to the seventh embodiment of the present invention.
Figure 42:
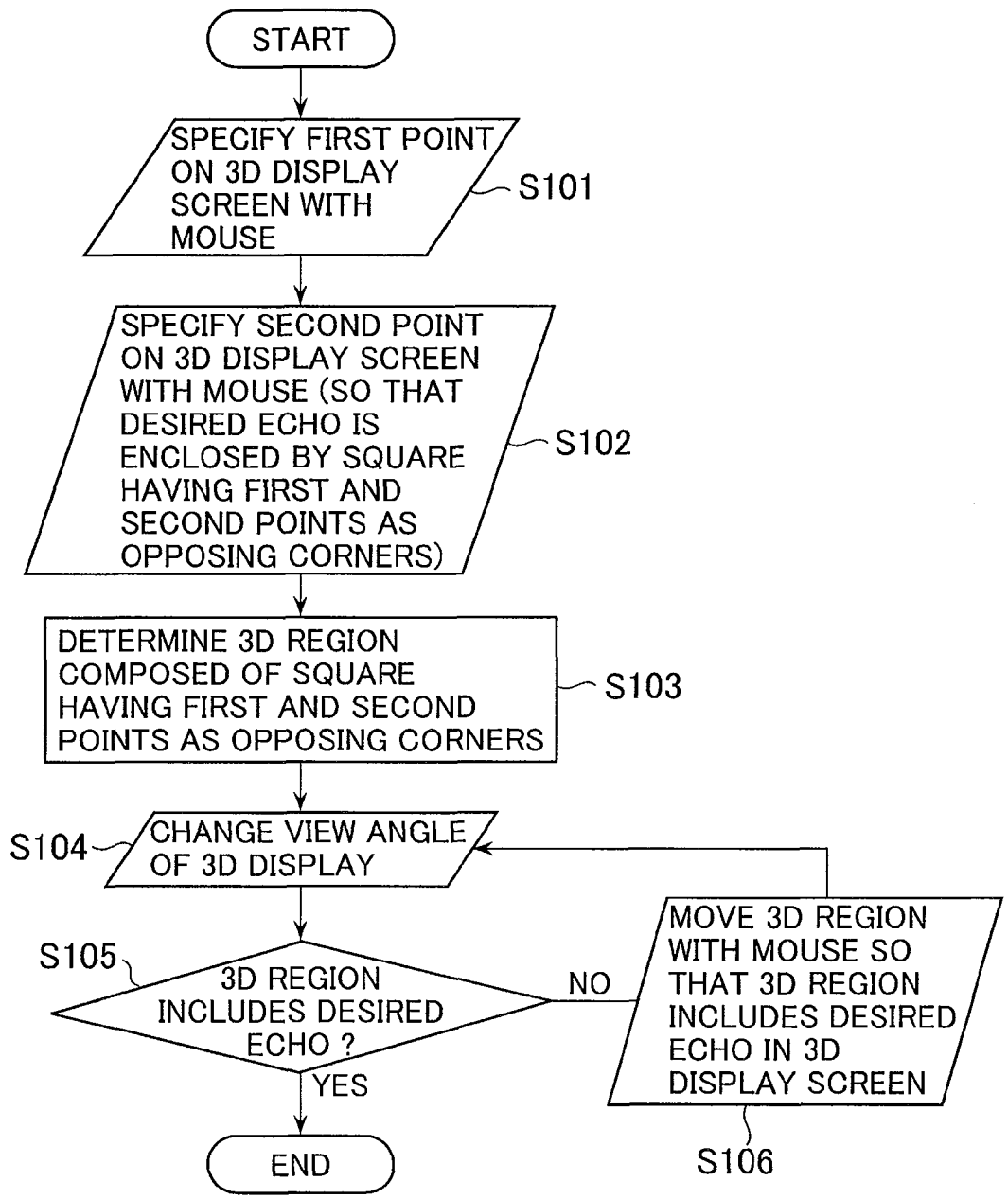
FIG. 42 is a flow chart illustrating detailed processing of the crack sizing method in the three-dimensional ultrasonic testing apparatus according to the seventh embodiment of the present invention.
Figure 43:
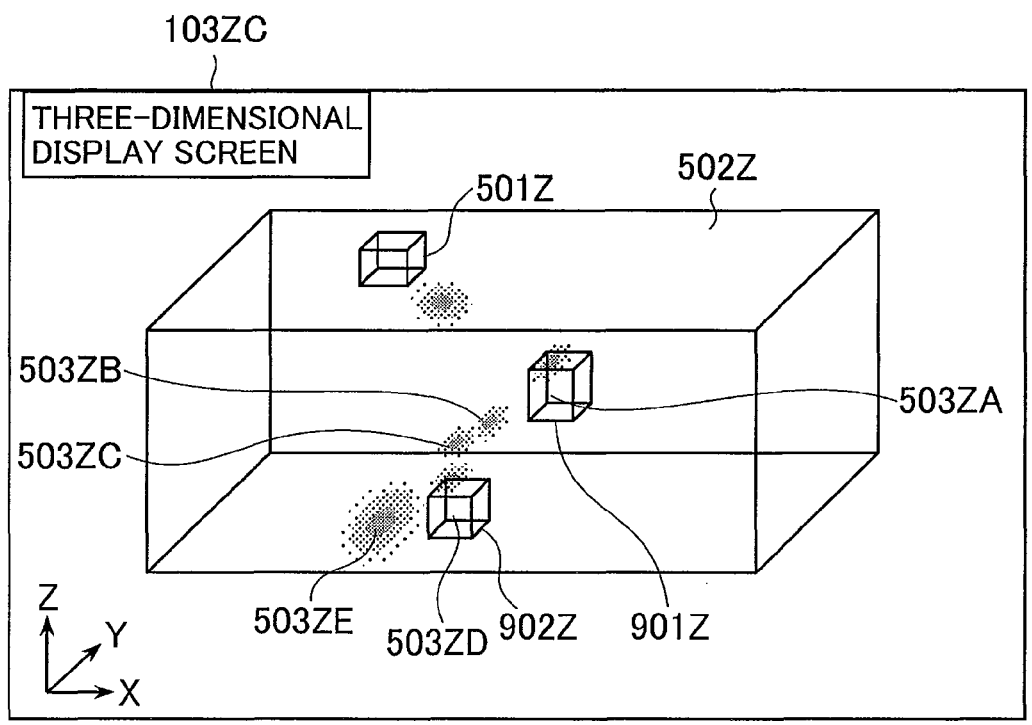
FIG. 43 illustrates a method for selecting a point on the three-dimensional display screen in the three-dimensional ultrasonic testing apparatus according to the seventh embodiment of the present invention.
Figure 44A:
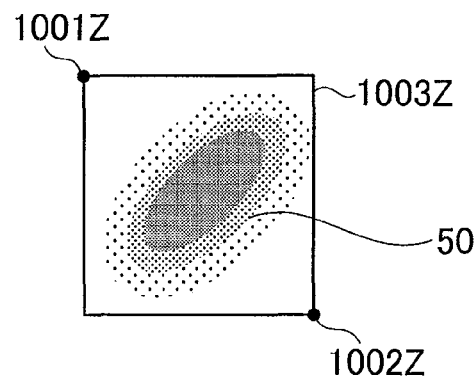
FIG. 44A, 44B illustrate a method for selecting a point having a maximum echo value on the three-dimensional display screen in the three-dimensional ultrasonic testing apparatus according to the seventh embodiment of the present invention.
Figure 44B:
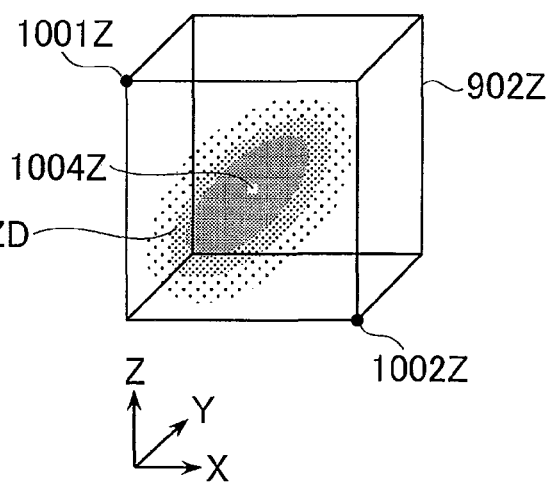
Figure 45:
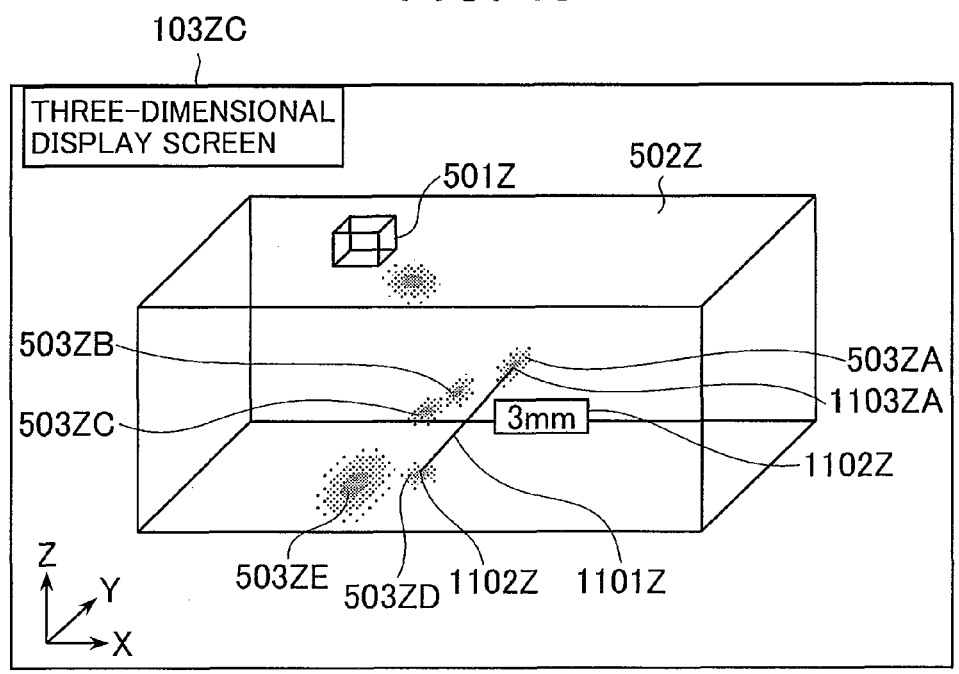
FIG. 45 illustrates exemplary linear display of a three-dimensional scale on the three-dimensional display screen in the three-dimensional ultrasonic testing apparatus according to the seventh embodiment of the present invention.

FIGS. 41 and 42 are flow charts illustrating detailed processing of the crack sizing method in the three-dimensional ultrasonic testing apparatus according to the seventh embodiment of the present invention. FIG. 43 illustrates a method for selecting a point on the three-dimensional display screen in the three-dimensional ultrasonic testing apparatus according to the seventh embodiment of the present invention. FIGS. 44A and 44B illustrate a method for selecting a point having a maximum value of echoes on the three-dimensional display screen in the three-dimensional ultrasonic testing apparatus according to the seventh embodiment of the present invention. FIG. 45 illustrates an exemplary linear three-dimensional scale displayed on the three-dimensional display screen in the three-dimensional ultrasonic testing apparatus according to the seventh embodiment of the present invention.

First of all, in step S100 of FIG. 41, the operator specifies a first cubic region containing a echo caused by the reflection at the crack originating portion D on the three-dimensional display screen.

A method for selecting a point on the three-dimensional display screen in the three-dimensional ultrasonic testing apparatus according to the present embodiment will be described below with reference to FIG. 43.

FIG. 43 illustrates exemplary three-dimensional testing data of the plate 302Z containing the crack 303Z displayed on the three-dimensional display screen 103ZC. Echoes displayed and CAD data are the same as those shown in FIG. 39.

The following describes a process for measuring the distance from the originating portion 303ZD of the crack 303Z to the end portion 303ZA thereof at which the crack 303Z progresses most. A crack distance measurement mode is activated by clicking a button on the three-dimensional display screen 103ZC with a mouse 103ZF.

In step S100 of FIG. 41, the operator specifies a first cubic region 902Z containing an echo 503DZ caused by the reflection at the originating portion 303ZD on the three-dimensional display screen 103ZC.

Detailed processing of step S100 of FIG. 41 will be described with reference to the flow chart of FIG. 42, and FIGS. 44A and 44B.

In step S101 of FIG. 42, the inspector specifies a point 1001Z on the three-dimensional display screen displayed in a certain viewing direction with the mouse 102ZF (FIG. 35), as shown in FIG. 44A. In this case, the position at which the point 1001Z is specified is set in the vicinity of an echo to be selected, that is, an echo 503ZD shown in FIG. 44A.

Similarly, in step S102, the inspector specifies a point 1002Z as a second point with the mouse 102ZF. In this case, the second point is specified so that a square 1003Z having the first and second points as opposing corners contains the echo 503ZD.

When positions of the two points is specified, in step S103, the computer 102ZA (FIG. 35) determines the cubic region 902Z composed of the square 1003Z. However, in this stage, since a spatial position cannot be determined in the direction perpendicular to the viewing direction, it is set at most anterior or posterior position of the three-dimensional testing data or at an intermediate position thereof.

In step S104, the inspector changes the viewing direction with the mouse 102ZF. In a state shown in FIG. 43, three-dimensional shape data 502Z is shown so that the x-z plane comes to the front. This data can be viewed from the right-hand side face. Specifically, the operator can change the viewing direction so that the y-z plane comes to the front by dragging a vertical edge of the three-dimensional shape data 502Z with the mouse 102ZF to rotate the data by 90 degrees around the z axis of the display coordinate system. In this case, instead of the three-dimensional shape data 502Z, the operator can drag three-dimensional testing data 503ZA or 503ZE to rotate the data by 90 degrees around the z axis of the display coordinate system. It is also possible to display a push button set to rotate the data by 90 degrees around the z axis on the three-dimensional display screen 103ZC beforehand, and click this push button with the mouse to change the viewing direction.

In this state, in step S105, the computer 102ZA checks again whether or not the cubic region 902Z contains the echo

503ZD. The operator can move the cubic region 902Z in parallel with the mouse 102ZF independently of the three-dimensional testing data.

In determination in step S105, if the cubic region 902Z does not contain the echo 503ZD, the operator moves the cubic region 902Z with the mouse 102ZF so that the echo 503ZD is contained in the cubic region 902Z (step S106).

In step S104 again, the operator changes the viewing direction of the three-dimensional display to repeat the same check. Normally, when the operator repeats this operation once or twice, the echo 503ZD becomes to be contained in the cubic region 902Z. The first cubic region 902Z is specified with the above operations.

Although a three-dimensional region to be specified is a cube, it may be a rectangular parallelepiped, a sphere, or other three-dimensional region other than a cube.

In step S110 of FIG. 41, the computer 102ZA selects a voxel contained in the first cubic region 902Z.

In step S115, the computer 102ZA selects a voxel having a maximum value out of voxels included in first cubic region 902Z. In step S120, the computer 102ZA displays a voxel 1004Z on the three-dimensional display screen 103ZC in color that allows it to be recognized thereon, as shown in FIG. 44B.

In step S125, the inspector checks whether or not a point is displayed at a desired position, and if not, repeats steps S100 to 115 again.

If a point is displayed at a desired position, in step S130, the computer 102ZA determines this point as a first voxel position.

In steps S135 to S160, the inspector and the computer 102ZA specify a second cubic region 901Z including an echo 503ZA caused by the reflection at the originating portion 303ZA on the three-dimensional display screen 103ZC. A method for specifying the second cubic region 901Z and a method for determining the second voxel position are the same as the method for specifying the first cubic region 902Z and the method for determining the first voxel position, respectively.

In step S165, the computer 102ZA calculates the distance between the first and second voxel positions from coordinates values of the two voxel positions.

In step S170, the computer 102ZA displays a linear three-dimensional scale connecting between the first and second voxel positions on the three-dimensional display screen in color that allows it to be recognized thereon.

Specifically, as shown in FIG. 45, the computer 102ZA displays a linear three-dimensional scale 1101Z connecting between the first and second voxel positions on the three-dimensional display screen 103ZC in color that allows it to be recognized thereon. In this case, a distance L1 between the two points is also displayed on the display unit 1102Z in the vicinity of the three-dimensional scale. (For example, the distance between the two points is displayed as "3 mm" in the figure.)

The inspector can move both end points 1103ZA and 1103ZD of the three-dimensional scale 1101Z in parallel in the direction perpendicular to the viewing direction displayed up to a desired position, by dragging with the mouse 102ZF the two points. Thus, the setup position of the three-dimensional scale 1101Z can be fine-adjusted. The three-dimensional scale 1101Z is also applicable to measurement of distance between other portions by largely moving the point 1103ZA or 1103ZD. When the point 1103ZA or 1103ZD is moved, the straight line connecting the two points changes, and the numerical value at the display unit 1102Z displaying the distance between two points also changes accordingly.

Not only a point corresponding to an echo but also an ultrasonic incidence point or any point defined in CAD data 501Z and 502Z can be used as a point for defining the three-dimensional scale 1101Z. Therefore, it is also possible to measure distance between two points other than ones defined in voxel data.

As mentioned above, three-dimensional drawing processing for this purpose can be easily attained, for example, by utilizing libraries offered by OpenGL and DirectX (typical Graphics APIs) in a program.

As mentioned above, by operating the three-dimensional scale 1101Z on the three-dimensional display screen 103ZC, the inspector can perform sizing on the crack 303Z as well as measure distance between various positions without displaying a cross-section of the three-dimensional testing data. Thus, measurement procedures can be performed easily and efficiently.

Figure 46A:
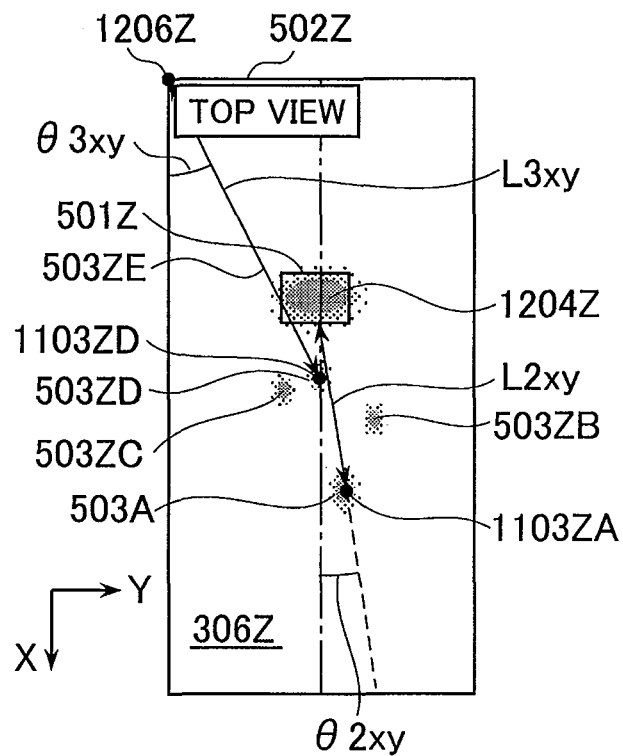
FIG. 46A, 46B illustrate exemplary display of information about positions with reference to other than a crack in the three-dimensional ultrasonic testing apparatus according to the seventh embodiment of the present invention.
Figure 46B:
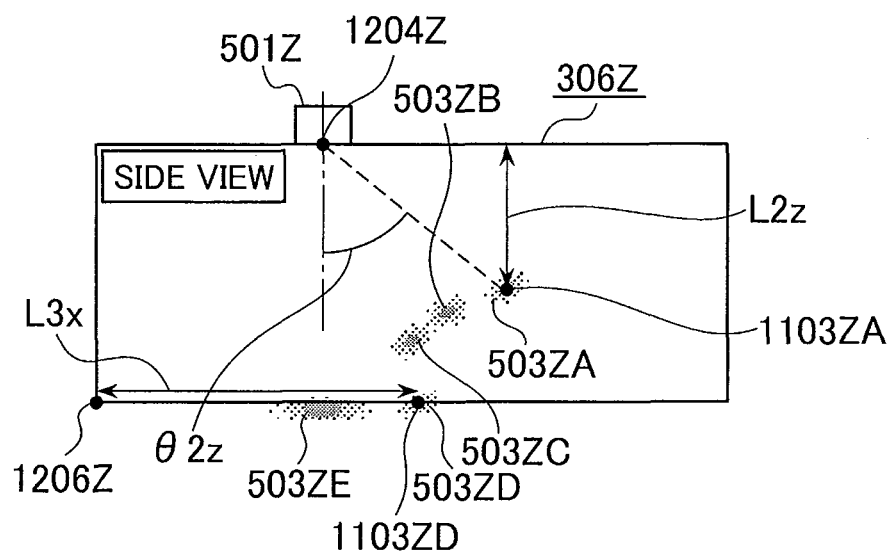

The following describes display of positional information with reference to a non-crack position in the three-dimensional ultrasonic testing apparatus according to the present embodiment referring to FIGS. 46A and 46B.

FIGS. 46A and 46B illustrate exemplary display of positional information with reference to a non-crack position in the three-dimensional ultrasonic testing apparatus according to the seventh embodiment of the present invention. FIG. 46A is a top view of FIG. 45, and FIG. 46B is a side view of FIG. 45.

In the example shown in FIG. 45, both end points 1103ZA and 1103ZD of a crack are specified as two points specified on the three-dimensional display unit, and the three-dimensional scale 1101Z is displayed with reference to these points. One of the two points specified on the three-dimensional display unit can be specified as a non-crack point.

As a first example, positional information with reference to an ultrasonic incidence point may be given as one of the two points specified on the three-dimensional display unit. A case in which the point 1103ZA is specified will be described below.

In this example, an ultrasonic incidence point 1204Z is specified as one of the two points specified on the three-dimensional display unit. Although the ultrasonic incidence point 1204Z can be specified using cube display as described in FIGS. 42 and 44, a push button named "Ultrasonic incidence point" is displayed on the three-dimensional display screen 103ZC and this push button is then clicked with the mouse to specify the ultrasonic incidence point 1204Z.

When two points are specified, a distance L2z from the testing surface 306Z shown in FIG. 46 is calculated and displayed at an appropriate position at an end of the three-dimensional display screen 103ZC. It is needless to say that the distance L2z may be displayed on another screen. This can be easily attained by calculating a distance between a plane defined in the CAD data 502Z of the plate 302Z read from the outside and the point 1103ZA.

Further, when viewed from the direction perpendicular to the testing surface 306Z, a distance L2xy formed by projecting a straight line connecting the ultrasonic incidence point 1204Z and the point 1103ZA onto the testing surface 306Z is calculated. This distance can also be calculated based on planar geometric information defined in the CAD data 502Z of the plate 302Z, and coordinate values of the point 1103ZA and the ultrasonic incidence point 1204Z.

An elevation angle $\theta 2z$ and an azimuthal angle $\theta 2xy$ of the point 1103ZA in a coordinate system having the ultrasonic incidence point 1204Z as an origin are calculated and displayed on the three-dimensional display screen 103ZC. Generally, this coordinates system is such that the normal direction (chain line) of the testing surface 306Z is set as the z axis. Although the x and y axes may be set in any desired way in relation to an object under test, they must be set with reference to an edge or a lateral face of the object under test or other characteristic shape.

Similarly, a distance, an elevation angle, and an azimuthal angle can be obtained for the other end point 1103ZD of the three-dimensional scale 1101Z.

As a second example, positional information with reference to an end point of the three-dimensional scale 1101Z may be given as one of the two points specified on the three-dimensional display unit. A case in which an end point 1206Z of the three-dimensional scale 1101Z is specified will be described below.

As one of the two points specified on the three-dimensional display unit, the end point 1206Z of the CAD data 502Z is specified. Although the end point 1206Z can be specified using cube display as described in FIGS. 42 and 44, a push button named "End point" is displayed on the three-dimensional display screen 103ZC and this push button is clicked with the mouse. Then, when the vicinity of a desired end point is specified in the AD data 502Z shown in FIG. 43 by using cube display, it is also possible to easily specify the end point 1206Z.

When two points are specified, distances $L3xy$ and $L3z$ from the end point 1206Z shown in FIG. 46 are calculated and displayed at an appropriate position at an end of the three-dimensional display screen 103ZC. It is needless to say that the distances $L3xy$ and $L3z$ may be displayed on another screen. This can be easily attained by calculating a distance between a plane defined in the CAD data 502Z of the plate 302Z read from the outside and the point 1103ZD.

An azimuthal angle $\theta 3xy$ of the point 1103ZD in a coordinate system having the end point 1206Z as an origin is calculated and displayed on the three-dimensional display screen 103ZC. The elevation angle in this case is 0 degree.

Further, after the inspector specifies any one end point of the three-dimensional scale 11012, for example, the point 1103ZA, the inspector specifies the end point by using a button on the three-dimensional display screen 103ZC. Then a sectorial plane having the shortest distance to the point 1103ZA (for example, the plane 404Z) out of a plurality of sectorial planes composing measurement data is automatically displayed on the two-dimensional display screen 103ZB.

Another configuration of a three-dimensional ultrasonic testing apparatus used for the present embodiment of the present invention will be described below with reference to FIG. 47.

Figure 47:
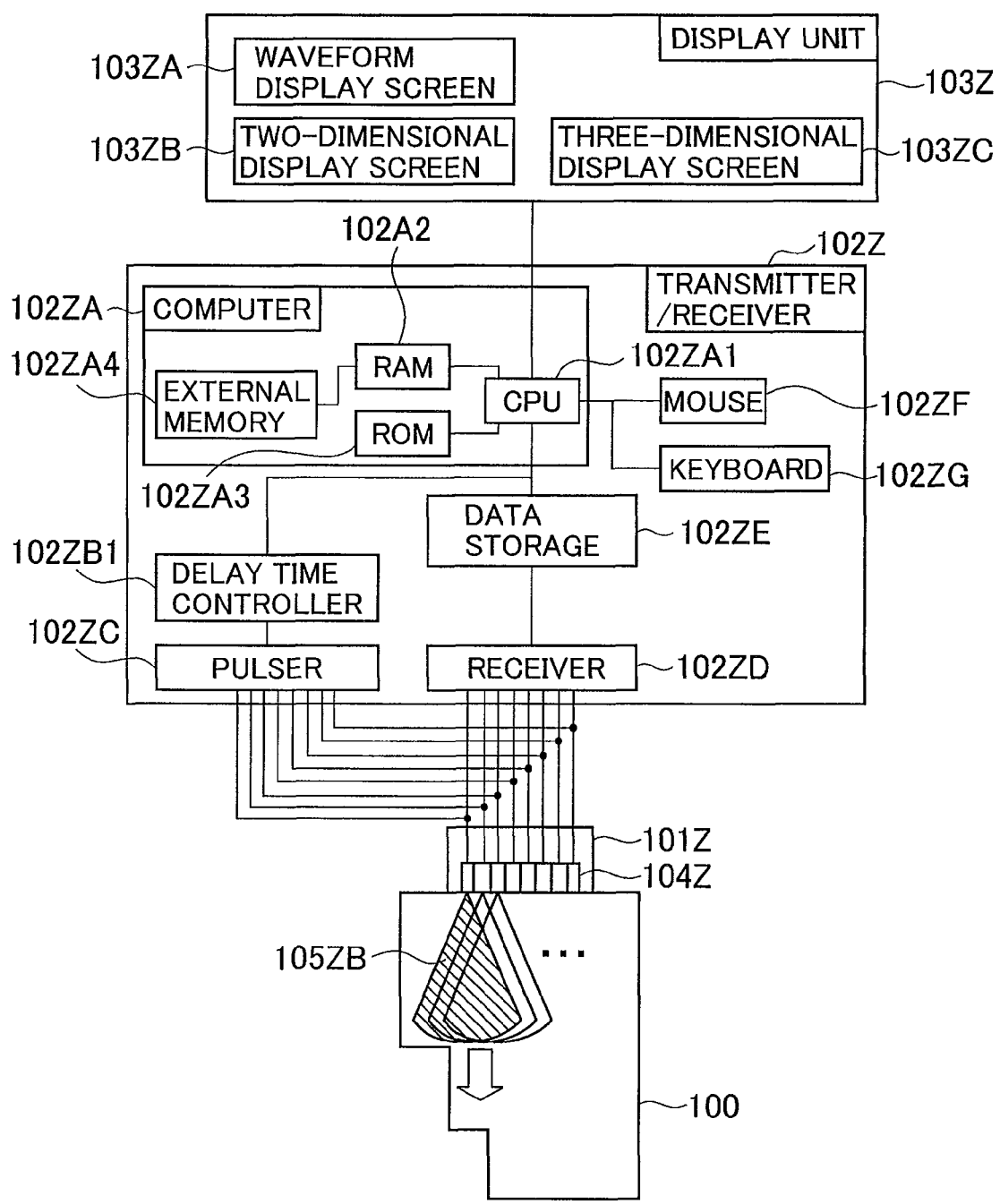
FIG. 47 is a block diagram illustrating another configuration of the three-dimensional ultrasonic testing apparatus used for the seventh embodiment of the present invention.

FIG. 47 is a block diagram illustrating another configuration of the three-dimensional ultrasonic testing apparatus used for the seventh embodiment of the present invention.

Although the three-dimensional ultrasonic testing apparatus shown in FIG. 35 obtains three-dimensional testing data by using the phased array method, the present invention is also applicable to three-dimensional testing data obtained by using a method other than the phased array method, for example, the synthetic aperture method.

FIG. 47 illustrates a configuration of the three-dimensional ultrasonic testing apparatus in a case where three-dimensional testing data is obtained by using the synthetic aperture method.

The three-dimensional ultrasonic testing apparatus according to the present embodiment includes an array ultrasonic sensor 1012 configured to transmit an ultrasonic wave to an object under test 100, a transmitter/receiver 102Z, and a display unit 103Z configured to display a receive signal and a testing image.

The array ultrasonic sensor 101Z is basically composed of a plurality of piezoelectric elements 104Z, each being able to transmit and receive an ultrasonic wave as shown in FIG. 47. The array ultrasonic sensor 101Z is disposed on a testing surface of the object under test 100. The array ultrasonic sensor 101Z transmits an ultrasonic beam 105ZB with a drive signal supplied from the transmitter/receiver 102Z, propagates the ultrasonic beam 105ZB in the object under test 100, detects a reflected wave appearing thereon, and feeds a receive signal to the transmitter/receiver 102Z.

The respective piezoelectric elements 104Z of the array ultrasonic sensor 101Z are sequentially driven at a necessary timing by a drive signal supplied from a drive signal controller 102ZB2 through a pulser 102ZC. The plurality of piezoelectric elements 104Z two-dimensionally receive a reflected wave of the ultrasonic wave generated therefrom. A receive signal is fed to a receiver 102ZD of the transmitter/receiver 102Z. Specifically, the respective piezoelectric elements 104Z of the array ultrasonic sensor 101Z receive reflected waves whose number is equal to the total number of the piezoelectric elements 104Z.

The signal fed to the receiver 102ZD is sequentially stored in data storage 102ZE as storage data. Based on the storage data, the computer 102ZA performs three-dimensional imaging of waveforms obtained by the piezoelectric elements 104Z by using the synthetic aperture method, and displays imaging results on the display unit 103Z.

The computer 102ZA basically includes a CPU 102ZA1, a RAM 102ZA2, a ROM 102ZA3, and an external memory 102ZA4. The ROM 102ZA3 has a program for controlling the CPU 102ZA1 written thereto. The CPU 102ZA1, according to the program, performs operations while reading necessary external data from the data storage 102ZE and exchanging data with the RAM 102ZA2, and outputs processed data to the data storage 102ZE as required.

A method for displaying and processing three-dimensional testing data 201Z generated by the synthetic aperture method by the computer 102ZA together with three-dimensional shape data 202Z, and a method for sizing a crack inside an object under test from a testing image are the same as those described in the above-mentioned first embodiment. Therefore, descriptions of these methods are omitted here.

As mentioned above, by operating the three-dimensional scale on the three-dimensional display screen, the inspector can size the crack as well as measure a distance between various positions without interruptively displaying the three-dimensional testing data. Thus, measurement procedures can be performed easily and efficiently.

What is claimed is:

1. A three-dimensional ultrasonic imaging apparatus comprising:
a two-dimensional array ultrasonic sensor composed of a plurality of piezoelectric elements;
pulsers configured to transmit a transmit signal to each piezoelectric element of the array ultrasonic sensor;
receivers configured to receive a receive signal;
delay control means configured to perform time control for the transmit and receive signals by varying a delay time for each piezoelectric element;
data storage means configured to store ultrasonic waveforms as waveform data transmitted and received by the array ultrasonic sensor;

sensor moving means configured to feed the array ultrasonic sensor, and scanning control means configured to control the sensor moving means;

displacement detection means configured to measure the displacement of the array ultrasonic sensor;

a computer configured to convert the stored waveform data to a plurality of pieces of three-dimensional testing data having a voxel format, and combine the plurality of pieces of three-dimensional testing data while making a shift by the displacement of the array ultrasonic sensor measured by the displacement detection means; and display means configured to display the combined testing data, wherein the display means includes data processing switching means configured to switch between testing data obtained by ordinary testing and testing data obtained by combining processing;

wherein, in ordinary testing, a maximum value out of testing data sequentially obtained by moving the array ultrasonic sensor is handled as testing data.

* * * * *